US009848058B2

(12) United States Patent
Johnson et al.

(10) Patent No.: US 9,848,058 B2
(45) Date of Patent: Dec. 19, 2017

(54) MEDICAL DATA TRANSPORT OVER WIRELESS LIFE CRITICAL NETWORK EMPLOYING DYNAMIC COMMUNICATION LINK MAPPING

(75) Inventors: David C. Johnson, Inver Grove Heights, MN (US); Jim Sievert, Shoreview, MN (US); Kenneth Hoyme, Plymouth, MN (US); John Lalonde, Lake Elmo, MN (US); William Mass, Renton, WA (US); David V. Duccini, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1857 days.

(21) Appl. No.: 12/228,915

(22) Filed: Aug. 18, 2008

(65) Prior Publication Data

US 2009/0063187 A1   Mar. 5, 2009

Related U.S. Application Data

(63) Continuation-in-part of application No. 12/151,869, filed on May 9, 2008, now Pat. No. 7,978,062, and a
(Continued)

(51) Int. Cl.
*G06Q 50/00* (2012.01)
*H04L 29/08* (2006.01)
(Continued)

(52) U.S. Cl.
CPC ............ *H04L 67/30* (2013.01); *A61B 5/0022* (2013.01); *A61B 5/411* (2013.01);
(Continued)

(58) Field of Classification Search
CPC .............................. G06Q 50/22; G06Q 50/24
(Continued)

(56) References Cited

U.S. PATENT DOCUMENTS 4,211,235 A   7/1980   Keller et al.
5,012,411 A   4/1991   Policastro et al.
(Continued)

FOREIGN PATENT DOCUMENTS

EP   1681803   7/2006
JP   08329374   12/1996
(Continued)

OTHER PUBLICATIONS

U.S. Appl. No. 12/151,869, filed May 9, 2008, LaLonde et al.
(Continued)

*Primary Examiner* — Lena Najarian
(74) *Attorney, Agent, or Firm* — Pauly, DeVries Smith & Deffner LLC

(57) ABSTRACT

A portable source medical device determines communication links of a network presently available to effect communications with a target component when the source medical device is at each of a multiplicity of geographical locations. A profile is generated comprising information about each available communication link and attributes associated with each available communication link for each geographical location. When the source medical device is at a particular geographical location, a profile associated with the particular geographical location is accessed and a network connection is established between the source medical device and the target component using a communication link associated with the particular profile. Medical information is transferred between the source medical device and the target component via the communication link associated with the particular profile.

25 Claims, 11 Drawing Sheets

Related U.S. Application Data continuation-in-part of application No. 12/151,780, filed on May 9, 2008, now Pat. No. 8,515,547, and a continuation-in-part of application No. 12/151,910, filed on May 9, 2008, now Pat. No. 8,395,498, and a continuation-in-part of application No. 12/151,796, filed on May 9, 2008, now abandoned.

(60) Provisional application No. 60/967,060, filed on Aug. 31, 2007, provisional application No. 60/967,061, filed on Aug. 31, 2007, provisional application No. 60/967,062, filed on Aug. 31, 2007, provisional application No. 60/967,063, filed on Aug. 31, 2007.

(51) Int. Cl.

| | | |
|---|---|---|
| *A61B 5/00* | (2006.01) | |
| *A61N 1/372* | (2006.01) | |
| *G06F 19/00* | (2011.01) | |
| *G06Q 50/22* | (2012.01) | |
| *H04L 12/701* | (2013.01) | |
| *H04L 12/725* | (2013.01) | |
| *H04W 4/02* | (2009.01) | |
| *H04W 4/20* | (2009.01) | |
| *H04W 48/18* | (2009.01) | |
| *A61B 5/0205* | (2006.01) | |
| *A61B 5/022* | (2006.01) | |
| *A61B 5/024* | (2006.01) | |
| *A61B 5/0402* | (2006.01) | |
| *A61B 5/083* | (2006.01) | |
| *A61B 5/11* | (2006.01) | |
| *A61B 5/145* | (2006.01) | |
| *H04W 4/00* | (2009.01) | |

(52) U.S. Cl.
CPC ....... *A61N 1/37282* (2013.01); *G06F 19/327* (2013.01); *G06F 19/3418* (2013.01); *G06Q 50/22* (2013.01); *H04L 45/00* (2013.01); *H04L 45/308* (2013.01); *H04L 67/18* (2013.01); *H04L 67/322* (2013.01); *H04W 4/02* (2013.01); *H04W 4/20* (2013.01); *H04W 48/18* (2013.01); *A61B 5/022* (2013.01); *A61B 5/024* (2013.01); *A61B 5/02055* (2013.01); *A61B 5/0402* (2013.01); *A61B 5/0836* (2013.01); *A61B 5/11* (2013.01); *A61B 5/145* (2013.01); *A61B 5/7232* (2013.01); *A61B 2560/045* (2013.01); *G06F 19/3412* (2013.01); *H04L 67/12* (2013.01); *H04W 4/001* (2013.01)

(58) Field of Classification Search
USPC .......................................................... 705/2, 3
See application file for complete search history.

(56) References Cited

U.S. PATENT DOCUMENTS

| | | |
|---|---|---|
| 5,033,286 A | 7/1991 | Guardiani |
| 5,047,930 A | 9/1991 | Martens et al. |
| 5,113,869 A | 5/1992 | Nappholz et al. |
| 5,293,642 A | 3/1994 | Lo |
| 5,336,245 A | 8/1994 | Adams et al. |
| 5,339,824 A | 8/1994 | Engira |
| 5,383,915 A | 1/1995 | Adams |
| 5,400,246 A | 3/1995 | Wilson et al. |
| 5,438,983 A | 8/1995 | Falcone |
| 5,462,051 A | 10/1995 | Oka et al. |
| 5,464,012 A | 11/1995 | Falcone |
| 5,522,396 A | 6/1996 | Langer et al. |
| 5,579,775 A | 12/1996 | Dempsey et al. |
| 5,620,472 A | 4/1997 | Rahbari |
| 5,634,468 A | 6/1997 | Platt et al. |
| 5,674,249 A | 10/1997 | de Coriolis et al. |
| 5,720,770 A | 2/1998 | Nappholz |
| 5,720,771 A | 2/1998 | Snell |
| 5,749,907 A | 5/1998 | Mann |
| 5,752,976 A | 5/1998 | Duffin et al. |
| 5,759,199 A | 6/1998 | Snell |
| 5,827,180 A | 10/1998 | Goodman |
| 5,867,821 A | 2/1999 | Ballantyne et al. |
| 5,873,040 A | 2/1999 | Dunn et al. |
| 5,880,867 A | 3/1999 | Ronald |
| 5,891,178 A | 4/1999 | Mann et al. |
| 5,899,855 A | 5/1999 | Brown |
| 5,904,708 A | 5/1999 | Goedeke |
| 5,959,529 A | 9/1999 | Kail |
| 6,050,940 A | 4/2000 | Braun et al. |
| 6,083,248 A | 7/2000 | Thompson |
| 6,088,594 A | 7/2000 | Kingdon et al. |
| 6,093,146 A | 7/2000 | Filangeri |
| 6,095,985 A | 8/2000 | Raymond et al. |
| 6,161,095 A | 12/2000 | Brown |
| 6,221,011 B1 | 4/2001 | Bardy |
| 6,225,901 B1 | 5/2001 | Kail, IV |
| 6,270,457 B1 | 8/2001 | Bardy |
| 6,277,072 B1 | 8/2001 | Bardy |
| 6,280,380 B1 | 8/2001 | Bardy |
| 6,282,441 B1 | 8/2001 | Raymond et al. |
| 6,287,252 B1 | 9/2001 | Lugo |
| 6,292,687 B1 * | 9/2001 | Lowell et al. ................ 600/515 |
| 6,312,378 B1 | 11/2001 | Bardy |
| 6,325,756 B1 | 12/2001 | Webb et al. |
| 6,330,426 B2 | 12/2001 | Brown et al. |
| 6,336,903 B1 | 1/2002 | Bardy |
| 6,353,761 B1 | 3/2002 | Conley et al. |
| 6,358,203 B2 | 3/2002 | Bardy |
| 6,363,282 B1 | 3/2002 | Nichols et al. |
| 6,368,284 B1 | 4/2002 | Bardy |
| 6,377,843 B1 | 4/2002 | Naydenov et al. |
| 6,396,416 B1 | 5/2002 | Kuusela et al. |
| 6,398,727 B1 | 6/2002 | Bui et al. |
| 6,398,728 B1 | 6/2002 | Bardy |
| 6,402,691 B1 | 6/2002 | Peddicord et al. |
| 6,405,083 B1 | 6/2002 | Rockwell et al. |
| 6,406,426 B1 | 6/2002 | Reuss et al. |
| 6,411,840 B1 | 6/2002 | Bardy |
| 6,413,213 B1 | 7/2002 | Essenpreis et al. |
| 6,418,346 B1 | 7/2002 | Nelson et al. |
| 6,428,475 B1 | 8/2002 | Shen |
| 6,434,429 B1 | 8/2002 | Kraus et al. |
| 6,440,066 B1 | 8/2002 | Bardy |
| 6,442,432 B2 | 8/2002 | Lee |
| 6,450,953 B1 | 9/2002 | Place et al. |
| 6,453,200 B1 | 9/2002 | Koslar |
| 6,456,256 B1 | 9/2002 | Amundson et al. |
| 6,466,819 B1 | 10/2002 | Weiss |
| 6,470,215 B1 | 10/2002 | Kraus et al. |
| 6,477,363 B1 | 11/2002 | Ayoub et al. |
| 6,477,424 B1 | 11/2002 | Thompson et al. |
| 6,480,745 B2 | 11/2002 | Nelson et al. |
| 6,485,418 B2 | 11/2002 | Yasushi et al. |
| 6,497,655 B1 | 12/2002 | Linberg et al. |
| 6,512,944 B1 | 1/2003 | Kovtun et al. |
| 6,544,171 B2 | 4/2003 | Beetz et al. |
| 6,544,173 B2 | 4/2003 | West et al. |
| 6,553,262 B1 | 4/2003 | Lang et al. |
| 6,556,871 B2 | 4/2003 | Schmitt et al. |
| 6,558,320 B1 | 5/2003 | Causey, III et al. |
| 6,561,851 B2 | 5/2003 | Florescu |
| 6,564,104 B2 * | 5/2003 | Nelson et al. ................ 607/60 |
| 6,564,108 B1 | 5/2003 | Makar et al. |
| 6,569,095 B2 | 5/2003 | Eggers |
| 6,574,509 B1 | 6/2003 | Kraus et al. |
| 6,574,510 B2 | 6/2003 | Von Arx et al. |
| 6,574,742 B1 | 6/2003 | Jamroga et al. |
| 6,577,899 B2 | 6/2003 | Lebel et al. |
| 6,584,356 B2 | 6/2003 | Wassmund et al. |
| 6,591,242 B1 | 7/2003 | Karp et al. |
| 6,599,250 B2 | 7/2003 | Webb et al. |
| 6,602,191 B2 | 8/2003 | Quy |

(56) References Cited

U.S. PATENT DOCUMENTS

| | | |
|---|---|---|
| 6,609,023 B1 | 8/2003 | Fischell et al. |
| 6,609,115 B1 | 8/2003 | Mehring |
| 6,611,206 B2 | 8/2003 | Eshelman et al. |
| 6,614,406 B2 | 9/2003 | Amundson et al. |
| 6,622,043 B1 | 9/2003 | Kraus et al. |
| 6,622,044 B2 | 9/2003 | Bange et al. |
| 6,622,050 B2 | 9/2003 | Thompson |
| 6,650,939 B2 | 11/2003 | Taepke, II et al. |
| 6,664,893 B1 | 12/2003 | Eveland et al. |
| 6,665,385 B2 | 12/2003 | Rogers et al. |
| 6,665,565 B1 | 12/2003 | Stomberg et al. |
| 6,675,045 B2 | 1/2004 | Mass et al. |
| 6,694,177 B2 | 2/2004 | Eggers et al. |
| 6,701,183 B2 | 3/2004 | Baker et al. |
| 6,708,065 B2 | 3/2004 | Von Arx et al. |
| 6,712,762 B1 | 3/2004 | Lichter et al. |
| 6,720,887 B1 | 4/2004 | Zunti |
| D490,525 S | 5/2004 | Stein et al. |
| 6,731,311 B2 | 5/2004 | Bufe et al. |
| 6,735,479 B2 | 5/2004 | Fabian et al. |
| 6,735,551 B2 | 5/2004 | Voegeli et al. |
| 6,747,556 B2 | 6/2004 | Medema et al. |
| 6,749,566 B2 | 6/2004 | Russ |
| 6,758,812 B2 | 7/2004 | Lang |
| 6,763,269 B2 | 7/2004 | Cox |
| 6,766,201 B2 | 7/2004 | Von Arx et al. |
| 6,773,396 B2 | 8/2004 | Flach et al. |
| 6,781,544 B2 | 8/2004 | Saliga et al. |
| 6,783,492 B2 | 8/2004 | Dominguez et al. |
| 6,785,573 B2 | 8/2004 | Kovtun et al. |
| 6,792,321 B2 | 9/2004 | Sepe, Jr. |
| 6,801,137 B2 | 10/2004 | Eggers |
| 6,801,802 B2 | 10/2004 | Sitzman et al. |
| 6,804,557 B1 | 10/2004 | Kroll |
| 6,804,558 B2 | 10/2004 | Haller et al. |
| 6,804,559 B1 | 10/2004 | Kraus et al. |
| 6,809,701 B2 | 10/2004 | Amundson et al. |
| 6,820,057 B1 | 11/2004 | Loch et al. |
| 6,840,904 B2 | 1/2005 | Goldberg |
| 6,850,252 B1 | 2/2005 | Hoffberg |
| 6,878,112 B2 | 4/2005 | Linberg et al. |
| 6,885,288 B2 | 4/2005 | Pincus |
| 6,889,086 B2 | 5/2005 | Mass et al. |
| 6,893,395 B1 | 5/2005 | Kraus et al. |
| 6,903,657 B2 | 6/2005 | Kwoen |
| 6,915,265 B1 | 7/2005 | Johnson |
| 6,936,007 B2 | 8/2005 | Quy |
| 6,940,403 B2 | 9/2005 | Kail, IV |
| 6,941,168 B2 | 9/2005 | Girouard |
| 6,954,673 B2 | 10/2005 | Von Arx et al. |
| 6,957,102 B2 | 10/2005 | Silver et al. |
| 6,957,107 B2 | 10/2005 | Rogers et al. |
| 6,958,705 B2 | 10/2005 | Lebel |
| 6,961,621 B2 | 11/2005 | Krishnan et al. |
| 6,963,907 B1 | 11/2005 | McBride et al. |
| 6,970,737 B1 | 11/2005 | Brodnick et al. |
| 6,976,958 B2 | 12/2005 | Quy |
| 6,978,169 B1 | 12/2005 | Guerra |
| 6,978,182 B2 | 12/2005 | Mazar et al. |
| 6,980,112 B2 | 12/2005 | Nee |
| 6,985,771 B2 | 1/2006 | Fischell et al. |
| 6,988,989 B2 | 1/2006 | Weiner et al. |
| 6,993,393 B2 | 1/2006 | Von Arx et al. |
| 7,002,468 B2 | 2/2006 | Eveland et al. |
| 7,009,511 B2 | 3/2006 | Mazar et al. |
| 7,016,739 B2 | 3/2006 | Bange et al. |
| 7,043,305 B2 | 5/2006 | KenKnight et al. |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,883 B2 | 6/2006 | Schmidt et al. |
| 7,070,562 B2 | 7/2006 | Bardy |
| 7,072,718 B2 | 7/2006 | Von Arx et al. |
| 7,079,035 B2 | 7/2006 | Bock et al. |
| 7,096,067 B2 | 8/2006 | Linberg |
| 7,096,068 B2 | 8/2006 | Mass et al. |
| 7,098,861 B2 | 8/2006 | Theobold et al. |
| 7,099,715 B2 | 8/2006 | Korzinov et al. |
| 7,104,955 B2 | 9/2006 | Bardy |
| 7,117,031 B2 | 10/2006 | Lohman et al. |
| 7,120,488 B2 | 10/2006 | Nova et al. |
| 7,123,950 B2 | 10/2006 | Mannheimer |
| 7,127,300 B2 | 10/2006 | Mazar et al. |
| 7,130,396 B2 | 10/2006 | Rogers et al. |
| 7,134,996 B2 | 11/2006 | Bardy |
| 7,149,570 B2 | 12/2006 | Ellscheid et al. |
| 7,149,773 B2 | 12/2006 | Haller et al. |
| 7,151,435 B2 | 12/2006 | Brackett et al. |
| 7,155,290 B2 | 12/2006 | Von Arx et al. |
| 7,156,808 B2 | 1/2007 | Quy |
| 7,156,809 B2 | 1/2007 | Quy |
| 7,181,017 B1 | 2/2007 | Nagel |
| 7,181,505 B2 | 2/2007 | Haller et al. |
| 7,194,300 B2 | 3/2007 | Korzinov |
| 7,203,545 B2 | 4/2007 | Schmitt et al. |
| 7,209,790 B2 | 4/2007 | Thompson et al. |
| 7,212,849 B2 | 5/2007 | Zhang et al. |
| 7,212,850 B2 | 5/2007 | Prystowsky |
| 7,218,969 B2 | 5/2007 | Vallapureddy et al. |
| 7,240,833 B2 | 7/2007 | Zarembo |
| 7,257,447 B2 | 8/2007 | Cates et al. |
| 7,270,633 B1 | 9/2007 | Goscha et al. |
| 7,273,454 B2 | 9/2007 | Raymond et al. |
| 7,283,864 B2 | 10/2007 | Thomas et al. |
| 7,286,872 B2 | 10/2007 | Kramer et al. |
| 7,289,761 B2 | 10/2007 | Mazar |
| 7,292,139 B2 | 11/2007 | Mazar et al. |
| 7,313,441 B2 | 12/2007 | Mass et al. |
| 7,316,648 B2 | 1/2008 | Kelly et al. |
| 7,319,903 B2 | 1/2008 | Bange et al. |
| 7,324,850 B2 | 1/2008 | Persen et al. |
| 7,353,063 B2 | 4/2008 | Simms, Jr. |
| 7,359,753 B2 | 4/2008 | Bange et al. |
| 7,363,080 B2 | 4/2008 | Stubbs et al. |
| 7,373,200 B2 | 5/2008 | Stubbs et al. |
| 7,378,955 B2 | 5/2008 | Mazar et al. |
| 7,383,087 B2 | 6/2008 | Hoyme et al. |
| 7,383,088 B2 | 6/2008 | Spinelli et al. |
| 7,389,146 B2 | 6/2008 | Hanson et al. |
| 7,392,086 B2 | 6/2008 | Sathaye |
| 7,392,092 B2 | 6/2008 | Li et al. |
| 7,395,117 B2 | 7/2008 | Mazar et al. |
| 7,418,298 B2 | 8/2008 | Shiroff et al. |
| 7,429,920 B2 | 9/2008 | Smythe et al. |
| 7,440,805 B2 | 10/2008 | Holmquist et al. |
| 7,460,910 B2 | 12/2008 | Webb |
| 7,460,912 B2 | 12/2008 | Hoyme et al. |
| 7,460,914 B2 | 12/2008 | Mandrusov et al. |
| 7,483,744 B2 | 1/2009 | Stubbs et al. |
| 7,483,752 B2 | 1/2009 | Von Arx et al. |
| 7,483,956 B2 | 1/2009 | Denney et al. |
| 7,515,963 B2 | 4/2009 | Axelrod et al. |
| 7,529,921 B2 | 5/2009 | Stein et al. |
| 7,536,557 B2 | 5/2009 | Murakami et al. |
| 7,551,965 B2 | 6/2009 | Bange et al. |
| 7,587,368 B2 | 9/2009 | Felsher |
| 7,610,065 B2 | 10/2009 | Vallapureddy et al. |
| 7,613,521 B2 | 11/2009 | Mass et al. |
| 7,621,906 B2 | 11/2009 | Pastore et al. |
| 7,623,922 B2 | 11/2009 | Bange et al. |
| 7,630,773 B2 | 12/2009 | Seeberger et al. |
| 7,664,548 B2 | 2/2010 | Amurthur et al. |
| 7,710,648 B2 | 5/2010 | Chestak et al. |
| 7,738,964 B2 | 6/2010 | Von Arx et al. |
| 7,751,801 B2 | 7/2010 | Torvinen |
| 7,751,901 B2 | 7/2010 | Mazar et al. |
| 7,752,059 B2 | 7/2010 | Sweeney |
| 7,756,573 B2 | 7/2010 | Shen et al. |
| 7,769,454 B2 | 8/2010 | Parkinson et al. |
| 7,769,456 B2 | 8/2010 | Bange et al. |
| 7,787,953 B2 | 8/2010 | Vallapureddy et al. |
| 7,801,612 B2 | 9/2010 | Johnson et al. |
| 7,801,620 B2 | 9/2010 | Freeberg |
| 7,805,199 B2 | 9/2010 | KenKnight et al. |

(56) References Cited

U.S. PATENT DOCUMENTS

| | | |
|---|---|---|
| 7,826,897 B2 | 11/2010 | Stubbs et al. |
| 7,830,381 B2 | 11/2010 | Lundstrom et al. |
| 7,844,337 B2 | 11/2010 | Hoyme et al. |
| 7,865,242 B2 | 1/2011 | Diebold et al. |
| 7,889,069 B2 | 2/2011 | Fifolt et al. |
| 7,941,207 B2 | 5/2011 | Korzinov |
| 7,955,258 B2 | 6/2011 | Goscha et al. |
| 7,967,751 B2 | 6/2011 | Goscha et al. |
| 7,978,062 B2 | 7/2011 | LaLonde et al. |
| 8,014,863 B2 | 9/2011 | Zhang et al. |
| 8,027,632 B2 | 9/2011 | Mazar |
| 8,027,727 B2 | 9/2011 | Freeberg |
| 8,041,032 B2 | 10/2011 | Katoozi et al. |
| 8,073,008 B2 | 12/2011 | Mehta et al. |
| 8,108,034 B2 | 1/2012 | Patangay et al. |
| 8,185,204 B2 | 5/2012 | Bange et al. |
| 8,211,033 B2 | 7/2012 | Siejko et al. |
| 8,246,563 B2 | 8/2012 | Wariar |
| 8,271,093 B2 | 9/2012 | Von Arx et al. |
| 8,290,129 B2 | 10/2012 | Rogers et al. |
| 8,290,589 B2 | 10/2012 | Bange et al. |
| 8,319,631 B2 | 11/2012 | Sievert et al. |
| 8,352,040 B2 | 1/2013 | Von Arx et al. |
| 8,373,556 B2 | 2/2013 | LaLonde et al. |
| 8,374,693 B2 | 2/2013 | Chavan et al. |
| 8,380,166 B2 | 2/2013 | Diebold et al. |
| 8,395,498 B2 | 3/2013 | Gaskill et al. |
| 8,423,149 B2 | 4/2013 | Hennig |
| 8,425,414 B2 | 4/2013 | Eveland |
| 8,462,678 B2 | 6/2013 | Splinter et al. |
| 8,489,197 B2 | 7/2013 | Schmitt et al. |
| 8,515,547 B2 | 8/2013 | Mass et al. |
| 8,587,427 B2 | 11/2013 | LaLonde et al. |
| 8,588,912 B2 | 11/2013 | Hoyme et al. |
| 8,638,221 B2 | 1/2014 | Sievert et al. |
| 8,706,251 B2 | 4/2014 | Von Arx et al. |
| 8,781,847 B2 | 7/2014 | Simms et al. |
| 8,812,841 B2 | 8/2014 | Sievert et al. |
| 8,818,522 B2 | 8/2014 | Mass et al. |
| 8,970,392 B2 | 3/2015 | Lalonde et al. |
| 9,269,251 B2 | 2/2016 | Lalonde et al. |
| 9,313,192 B2 | 4/2016 | Sievert et al. |
| 9,552,722 B2 | 1/2017 | Sievert et al. |
| 2002/0010679 A1 | 1/2002 | Felsher |
| 2002/0052539 A1 | 5/2002 | Haller |
| 2002/0055917 A1 | 5/2002 | Muraca |
| 2002/0072783 A1 | 6/2002 | Goedeke et al. |
| 2002/0082480 A1 | 6/2002 | Riff |
| 2002/0082665 A1 | 6/2002 | Haller et al. |
| 2002/0095196 A1 | 7/2002 | Linberg |
| 2002/0138768 A1 | 9/2002 | Murakami et al. |
| 2003/0025602 A1 | 2/2003 | Medema et al. |
| 2003/0078631 A1 | 4/2003 | Nelson et al. |
| 2003/0144711 A1 | 7/2003 | Pless et al. |
| 2004/0006265 A1 | 1/2004 | Alhussiny |
| 2004/0038706 A1* | 2/2004 | Wasser .................... 455/551 |
| 2004/0048601 A1 | 3/2004 | Lee et al. |
| 2004/0117308 A1 | 6/2004 | Bouknight |
| 2004/0122488 A1 | 6/2004 | Mazar et al. |
| 2004/0128161 A1 | 7/2004 | Mazar et al. |
| 2004/0167465 A1 | 8/2004 | Mihai et al. |
| 2004/0170154 A1 | 9/2004 | Carter et al. |
| 2004/0230246 A1 | 11/2004 | Stein et al. |
| 2004/0230247 A1 | 11/2004 | Stein et al. |
| 2004/0233930 A1 | 11/2004 | Colby, Jr. |
| 2004/0260189 A1 | 12/2004 | Eggers et al. |
| 2005/0021370 A1 | 1/2005 | Riff et al. |
| 2005/0032511 A1 | 2/2005 | Malone et al. |
| 2005/0033124 A1* | 2/2005 | Kelly et al. .................... 600/300 |
| 2005/0071199 A1 | 3/2005 | Riff |
| 2005/0091338 A1 | 4/2005 | De la Huerga |
| 2005/0113885 A1 | 5/2005 | Haubrich et al. |
| 2005/0114711 A1 | 5/2005 | Hesselink |
| 2005/0120082 A1 | 6/2005 | Hesselink |
| 2005/0124866 A1 | 6/2005 | Elaz et al. |
| 2005/0125258 A1 | 6/2005 | Yellin |
| 2005/0135288 A1 | 6/2005 | Al-Ali et al. |
| 2005/0144186 A1 | 6/2005 | Hesselink |
| 2005/0144195 A1 | 6/2005 | Hesselink |
| 2005/0144200 A1 | 6/2005 | Hesselink |
| 2005/0149481 A1 | 7/2005 | Hesselink |
| 2005/0192649 A1 | 9/2005 | Shehadeh et al. |
| 2005/0192836 A1 | 9/2005 | Rossinni et al. |
| 2005/0192837 A1 | 9/2005 | Fears et al. |
| 2005/0192838 A1 | 9/2005 | Jones et al. |
| 2005/0206518 A1 | 9/2005 | Welch et al. |
| 2005/0241026 A1 | 10/2005 | Esler et al. |
| 2005/0245995 A1 | 11/2005 | Diebold |
| 2005/0251227 A1 | 11/2005 | Khoo et al. |
| 2005/0282494 A1 | 12/2005 | Kossi |
| 2005/0288808 A1 | 12/2005 | Lopez et al. |
| 2006/0020314 A1 | 1/2006 | Bodner |
| 2006/0020960 A1 | 1/2006 | Relan |
| 2006/0045112 A1 | 3/2006 | Laiho et al. |
| 2006/0064133 A1 | 3/2006 | Von Arx et al. |
| 2006/0064142 A1 | 3/2006 | Chavan et al. |
| 2006/0089856 A1 | 4/2006 | Kadhiresan et al. |
| 2006/0136717 A1 | 6/2006 | Buer et al. |
| 2006/0142820 A1 | 6/2006 | Von Arx et al. |
| 2006/0154642 A1 | 7/2006 | Scannell, Jr. |
| 2006/0161213 A1 | 7/2006 | Patel |
| 2006/0173985 A1 | 8/2006 | Moore |
| 2006/0200007 A1 | 9/2006 | Brockway et al. |
| 2006/0206246 A1 | 9/2006 | Walker |
| 2006/0218054 A1 | 9/2006 | Postelnik et al. |
| 2006/0253300 A1 | 11/2006 | Somberg et al. |
| 2006/0253301 A1 | 11/2006 | Simms et al. |
| 2006/0253894 A1 | 11/2006 | Bookman |
| 2006/0265740 A1 | 11/2006 | Clark |
| 2007/0027723 A1 | 2/2007 | Bardy |
| 2007/0036771 A1 | 2/2007 | Wagner et al. |
| 2007/0061266 A1 | 3/2007 | Moore |
| 2007/0083246 A1 | 4/2007 | Mazar et al. |
| 2007/0100384 A1 | 5/2007 | Fischell et al. |
| 2007/0106129 A1 | 5/2007 | Srivathsa et al. |
| 2007/0106536 A1 | 5/2007 | Moore |
| 2007/0106537 A1 | 5/2007 | Moore |
| 2007/0106750 A1 | 5/2007 | Moore |
| 2007/0106751 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0118188 A1 | 5/2007 | Von Arx et al. |
| 2007/0123946 A1 | 5/2007 | Masoud |
| 2007/0135855 A1 | 6/2007 | Foshee et al. |
| 2007/0136098 A1 | 6/2007 | Smythe et al. |
| 2007/0138253 A1 | 6/2007 | Libin |
| 2007/0142727 A1 | 6/2007 | Zhang et al. |
| 2007/0156054 A1 | 7/2007 | Korzinov et al. |
| 2007/0157298 A1 | 7/2007 | Dingwall |
| 2007/0168222 A1 | 7/2007 | Hoyme et al. |
| 2007/0168461 A1 | 7/2007 | Moore |
| 2007/0179349 A1 | 8/2007 | Hoyme et al. |
| 2007/0180047 A1 | 8/2007 | Dong et al. |
| 2007/0192140 A1 | 8/2007 | Gropper |
| 2007/0203754 A1 | 8/2007 | Harrington |
| 2007/0206615 A1 | 9/2007 | Plamondon et al. |
| 2007/0210923 A1 | 9/2007 | Butler |
| 2007/0226013 A1 | 9/2007 | Elletson et al. |
| 2007/0260293 A1 | 11/2007 | Carpenter et al. |
| 2007/0263873 A1 | 11/2007 | Qi |
| 2007/0265533 A1 | 11/2007 | Tran |
| 2007/0273504 A1 | 11/2007 | Tran |
| 2007/0276270 A1 | 11/2007 | Tran |
| 2007/0293776 A1 | 12/2007 | Korzinov et al. |
| 2007/0299317 A1 | 12/2007 | Hoyme et al. |
| 2008/0001735 A1 | 1/2008 | Tran |
| 2008/0004904 A1 | 1/2008 | Tran |
| 2008/0021521 A1 | 1/2008 | Shah et al. |
| 2008/0021523 A1 | 1/2008 | Cates et al. |
| 2008/0021730 A1 | 1/2008 | Holla |
| 2008/0021741 A1 | 1/2008 | Holla |

(56) References Cited

U.S. PATENT DOCUMENTS

| | | |
|---|---|---|
| 2008/0021834 A1 | 1/2008 | Holla |
| 2008/0027499 A1 | 1/2008 | Srivathsa et al. |
| 2008/0040151 A1 | 2/2008 | Moore |
| 2008/0058881 A1 | 3/2008 | Wagner et al. |
| 2008/0061961 A1 | 3/2008 | John |
| 2008/0071183 A1 | 3/2008 | Thomas et al. |
| 2008/0071314 A1 | 3/2008 | John |
| 2008/0097551 A1 | 4/2008 | Dicks et al. |
| 2008/0140163 A1 | 6/2008 | Keacher |
| 2008/0154099 A1 | 6/2008 | Aspel |
| 2008/0157928 A1 | 7/2008 | Butler |
| 2008/0164975 A1 | 7/2008 | Butler |
| 2008/0164977 A1 | 7/2008 | Butler |
| 2008/0180249 A1 | 7/2008 | Butler |
| 2008/0186137 A1 | 8/2008 | Butler |
| 2008/0186138 A1 | 8/2008 | Butler |
| 2008/0186139 A1 | 8/2008 | Butler |
| 2008/0186180 A1 | 8/2008 | Butler |
| 2008/0209513 A1 | 8/2008 | Graves et al. |
| 2008/0211630 A1 | 9/2008 | Butler |
| 2008/0222711 A1 | 9/2008 | Michaelis |
| 2008/0252459 A1 | 10/2008 | Butler |
| 2008/0294019 A1 | 11/2008 | Tran |
| 2008/0306872 A1 | 12/2008 | Felsher |
| 2009/0019552 A1 | 1/2009 | McLaughlin |
| 2009/0024416 A1 | 1/2009 | McLaughlin |
| 2009/0058635 A1 | 3/2009 | LaLonde |
| 2009/0063187 A1 | 3/2009 | Johnson et al. |
| 2009/0063193 A1 | 3/2009 | Barton et al. |
| 2009/0099866 A1 | 4/2009 | Newman |
| 2009/0146822 A1 | 6/2009 | Soliman |
| 2009/0158274 A1 | 6/2009 | Roberts |
| 2009/0222898 A1 | 9/2009 | Veidung |
| 2009/0231125 A1 | 9/2009 | Baldus et al. |
| 2009/0240120 A1 | 9/2009 | Mensinger et al. |
| 2009/0240526 A1 | 9/2009 | Vesto et al. |
| 2009/0292340 A1 | 11/2009 | Mass et al. |
| 2009/0320029 A1 | 12/2009 | Kottomtharayil |
| 2010/0144316 A1 | 6/2010 | Piercy et al. |
| 2010/0225468 A1 | 9/2010 | Sievert et al. |
| 2010/0228977 A1 | 9/2010 | Sievert et al. |
| 2010/0250697 A1 | 9/2010 | Hansen et al. |
| 2011/0152970 A1 | 6/2011 | Jollota et al. |
| 2011/0202371 A1 | 8/2011 | Darguesse et al. |
| 2012/0068847 A1 | 3/2012 | Pirzada |
| 2013/0133011 A1 | 5/2013 | Chhaochharia et al. |
| 2013/0154851 A1 | 6/2013 | Gaskill et al. |
| 2013/0262311 A1 | 10/2013 | Buhrmann et al. |
| 2013/0310896 A1 | 11/2013 | Mass |
| 2014/0111353 A1 | 4/2014 | Sievert et al. |
| 2014/0337922 A1 | 11/2014 | Sievert |
| 2015/0206408 A1 | 7/2015 | Lalonde |

FOREIGN PATENT DOCUMENTS

| | | |
|---|---|---|
| JP | 2003047599 | 2/2003 |
| JP | 2005080175 | 3/2005 |
| JP | 2007200276 | 8/2007 |
| WO | WO 97/36443 | 10/1997 |
| WO | WO03077994 | 9/2003 |
| WO | WO 03/100647 | 12/2003 |
| WO | WO 2004/109992 | 12/2004 |
| WO | WO2006010166 | 1/2006 |
| WO | WO2009032134 | 3/2009 |

OTHER PUBLICATIONS

Savci et al., "MICS Transceivers: Regulatory Standards and Applications", IEEE Proceedings, Apr. 8, 2005. pp. 179-182.
Valdastri et al., "An implantable ZigBee ready telemetric platform for in vivo monitoring of physiological parameters," Sensors and Actuators A, vol. 142, 2008, pp. 369-378.
U.S. Appl. No. 12/694,817, filed Jan. 27, 2010, Sievert et al.
U.S. Appl. No. 14/694,826, filed Jan. 27, 2010, Sievert et al.
Biotronic Technical Manual for Philos DR-T, DDDR Dual Chamber Pulse Generator with Home Monitor, 2004, 32 pages.
Medtronic Analyzer Reference Guide for Medtronic Carelink Analyzer, Model 2290 Analyzer for Medtronic and Vitatron Devices, 2008, 106 pages.
Medtronic Programmer Reference Guide for Medtronic Carelink Programmer, Model 2090 Programmer for Medtronic and Vitatron Devices, 2008, 112 pages.
International Search Report and Written Opinion dated Apr. 9, 2009 from International Application No. PCT/US2008/010162, 24 pages.
International Preliminary Report on Patentability dated Mar. 1, 2010 from International Application No. PCT/US2008/010162, 13 pages.
Office Action dated Oct. 5, 2010 from U.S. Appl. No. 12/151,869, 6 pages.
Office Action Response submitted Oct. 7, 2010 to office action dated Oct. 5, 2010 from U.S. Appl. No. 12/151,869, 9 pages.
International Search Report and Written Opinion from International Application No. PCT/US2010/026076 dated Oct. 11, 2010, 17 pages.
Margolis et al., Latitude Active Monitoring alerts physician of silent AF episode, Latitude Patient Management Case Study, Boston Scientific Corporation, 2006, 2 pages.
Office Action dated Feb. 11, 2011 for U.S. Appl. No. 12/151,780, 15 pages.
Office Action Response dated Apr. 27, 2011 for U.S. Appl. No. 12/151,780, 16 pages.
Office Action dated Apr. 18, 2011 for U.S. Appl. No. 12/151,796, 20 pages.
Notice of Allowance dated Mar. 4, 2011 from U.S. Appl. No. 12/151,869, 5 pages.
File History for U.S. Appl. No. 12/151,780.
File History for U.S. Appl. No. 12/151,796.
File History for U.S. Appl. No. 12/151,869.
File History for U.S. Appl. No. 13/181,176.
File History for U.S. Appl. No. 12/151,910.
File History for EP App. No. 08795636.3.
Office Action dated Mar. 21, 2012 for Japanese Application No. 2010-522944, 15 pages.
File History for European Application No. 08795636.3 as retrieved from the European Patent Office Electronic Filing System on May 10, 2012, 91 pages.
File History for U.S. Appl. No. 12/694,817.
File History for European Application No. 08795636.3 as retrieved from the European Patent Office Electronic Filing System on Jun. 15, 2012, 92 pages.
JP Office Action Response dated Jun. 20, 2012 for Japanese Application No. 2010-522944, 24 pages.
File History for U.S. Appl. No. 12/694,826.
Klemm, Fabius et al., "Alleviating effects of mobility on TCP performance in ad hoc networks using signal strength based link management", Lecture notes in Computer Science, vol. 2775, 2003, pp. 611-624.
"JP Office Action translation and pending claims", for Japanese Application No. 2011553082, mailed Dec 18, 2012 (7 pages).
"File History for U.S. Appl. No. 13/758,489".
"File History for U.S. Appl. No. 14/071,893".
"Partial File History for U.S. Appl. No. 12/694,817".
"File History for U.S. Appl. No. 13/684,893".
"Final Office Action", for U.S. Appl. No. 14/071,893, mailed Mar. 13, 2014 (9 pages).
"Notice of Allowance", for U.S. Appl. No. 12/694,817 mailed Apr. 11, 2014 (16 pages).
"Notice of Allowance", for U.S. Appl. No. 13/955,746, mailed Apr. 22, 2014 (49 pages).
"Non-Final Office Action", for U.S. Appl. No. 13/774,328, mailed Aug. 7, 2014 (18 pages).
"Notice of Allowance", for U.S. Appl. No. 14/071,893, mailed Aug. 28, 2014 (5 pages).
Invitation to Pay Additional Fees dated Jul. 12, 2010 from PCT Application No. PCT/US2010/026076, 6 pages.
"Final Office Action," for U.S. Appl. No. 14/139,569, dated Feb. 24, 2016 (24 pages).

(56) References Cited

OTHER PUBLICATIONS

"Final Office Action," for U.S. Appl. No. 13/774,328, dated on Dec. 4, 2014 (77 pages).
"Non-Final Office Action," for U.S. Appl. No. 14/139,569 dated Sep. 9, 2015 (66 pages).
"Non-Final Office Action," for U.S. Appl. No. 14/576,997, dated May 22, 2015 (30 pages).
"Appeal Brief," for U.S. Appl. No. 14/139,569, filed on May 24, 2016 (28 pages).
"Response to Non-Final Office Action," for U.S. Appl. No. 14/139,569 filed on Dec. 9, 2015 (14 pages).

* cited by examiner

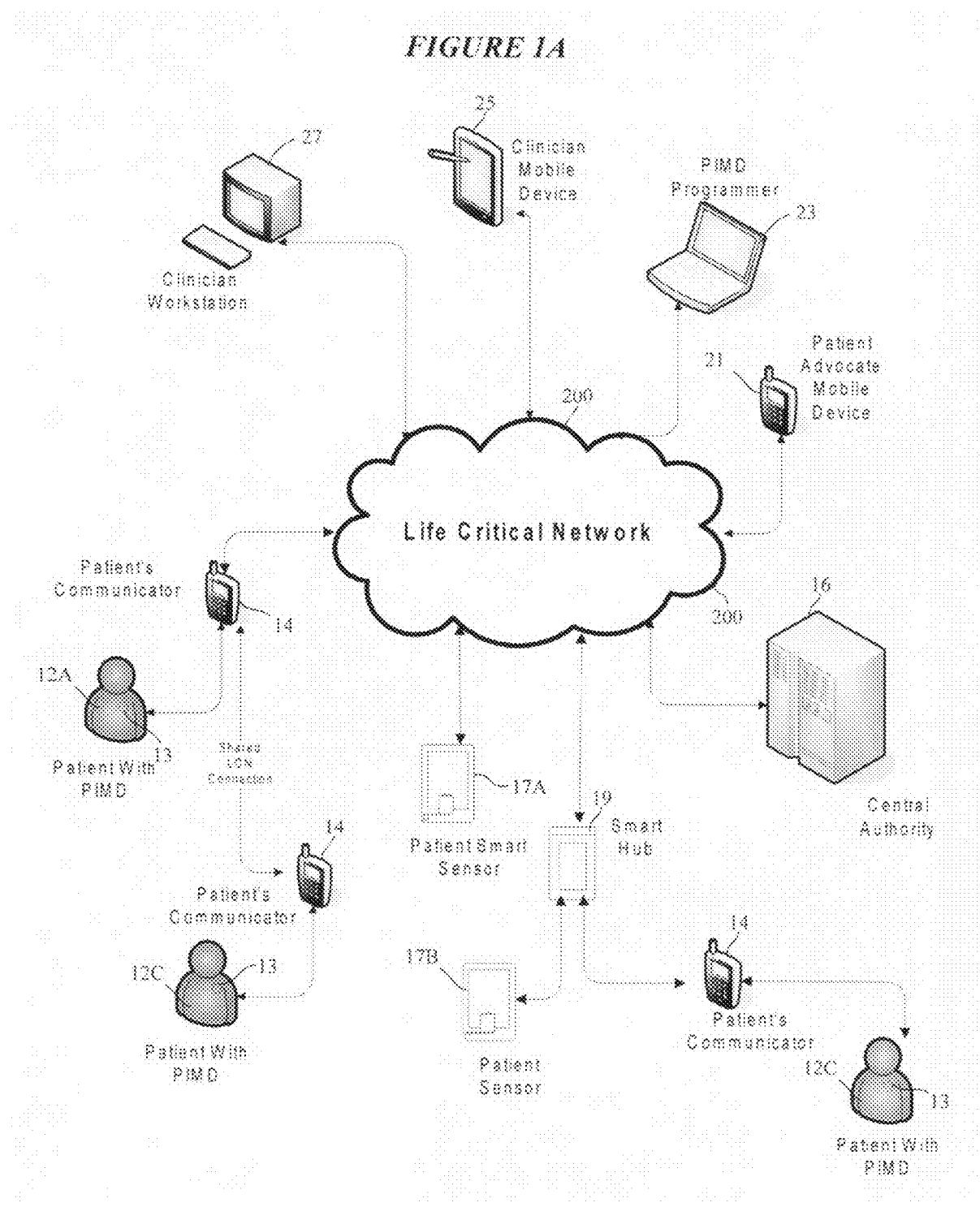

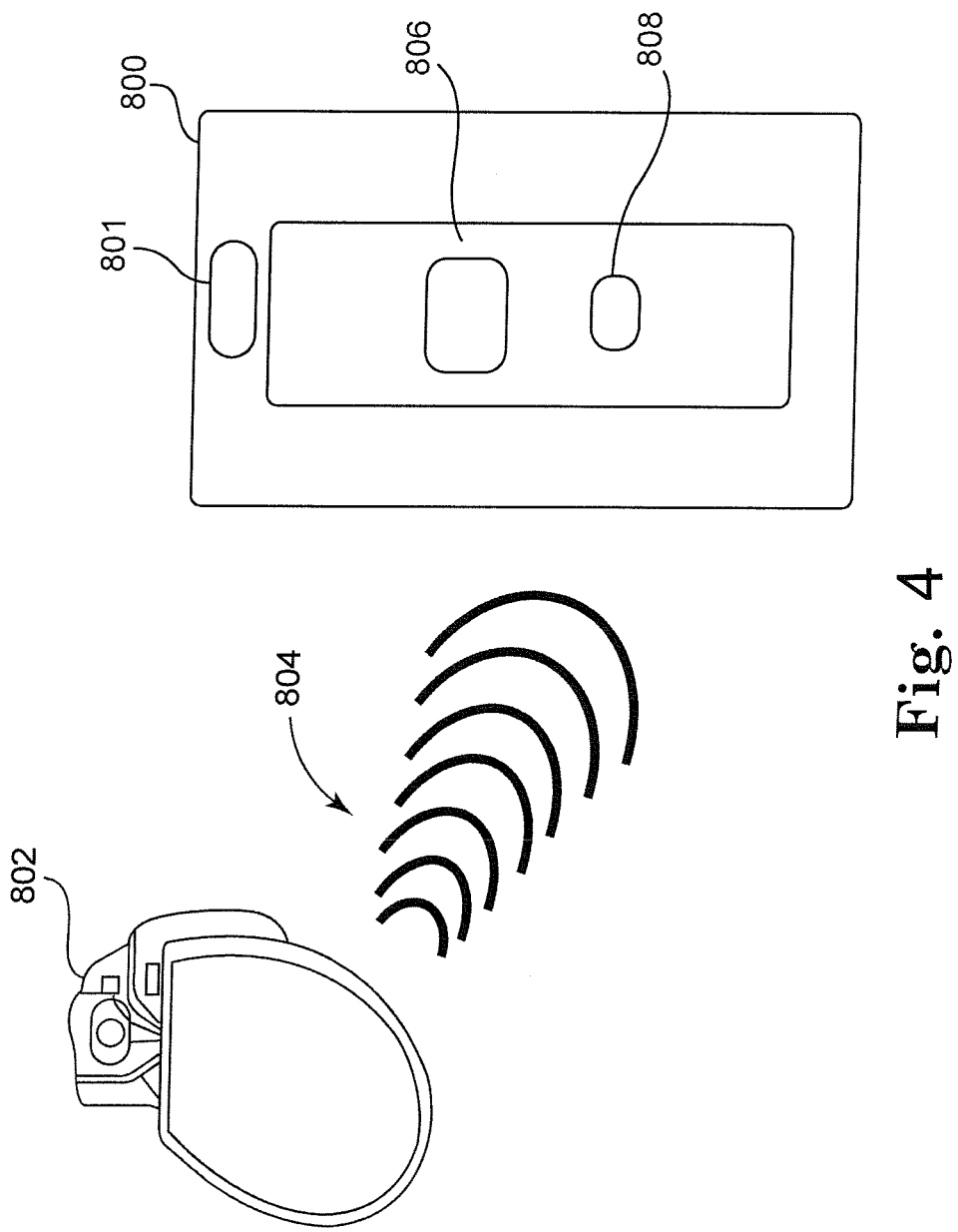

MEDICAL DATA TRANSPORT OVER WIRELESS LIFE CRITICAL NETWORK EMPLOYING DYNAMIC COMMUNICATION LINK MAPPING

RELATED APPLICATIONS

This application claims the benefit of Provisional Patent Application Ser. Nos. 60/967,060, 60/967,061, 60/967,062, and 60/967,063 filed on Aug. 31, 2007 and is a Continuation-In-Part of U.S. Ser. No. 12/151,869, filed May 9, 2008, now U.S. Pat. No. 7,978,062; U.S. Ser. No. 12/151,780, filed May 9, 2008, now U.S. Pat. No. 8,515,547 now U.S. Publication No. 2009/0062887; U.S. Ser. No. 12/151,910, filed May 9, 2008, now U.S. Pat. No. 8,395,498 now U.S. Serial No. 2009/0058636; and U.S. Ser. No. 12/151,796, filed May 9, 2008, now abandoned now U.S. Publication No. 2009/0063193, all of which are hereby incorporated herein by reference in their entireties.

FIELD OF THE INVENTION

The present invention relates generally to systems, devices, and methods for transporting medical information over a wireless network.

BACKGROUND

Implantable pulse generators (IPGs) are medical devices commonly used to treat irregular heartbeats, known as arrhythmias. Cardiac pacemakers, for example, are designed to manage bradycardia, an abnormally slow or irregular heartbeat. Left untreated, bradycardia can cause symptoms such as fatigue, dizziness, and fainting. Cardiac resynchronizers are a particular class of pacemaker that provide cardiac resynchronization therapy, such a bi-ventricular pacing, for patients suffering from heart failure. Implantable cardioverter defibrillators (ICDs), by way of further example, are designed to treat tachycardia, heart rhythms that are abnormally fast and life threatening. Some forms of tachycardia can result in sudden cardiac death, if left untreated.

Pacemakers and ICDs are increasingly being equipped with an on-board, volatile memory in which telemetered signals can be stored for later retrieval and analysis. The telemetered signals provide various types of patient device information, such as atrial electrical activity, ventricular electrical activity, time of day, activity level, cardiac output, oxygen level, cardiovascular pressure measures, pulmonary measures, and any interventions made on a per heartbeat or binned average basis. In addition, a growing class of cardiac medical devices, including implantable heart failure monitors, implantable event monitors, cardiovascular monitors, and therapy devices, are being used to provide similar stored device information. These devices are typically designed to store approximately thirty minutes of heartbeat data. Telemetered signals are also stored in a broader class of monitors and therapeutic devices for other areas of medicine, including metabolism, endocrinology, hematology, neurology, muscular, gastrointestinal, genital-urology, ocular, auditory, and the like.

Information stored in an implantable medical device is typically retrieved using a proprietary interrogator or programmer, often during a clinic visit or following a device event. The volume of data retrieved from a single device interrogation procedure can be large and proper interpretation and analysis can require significant physician time and detailed subspecialty knowledge, particularly by cardiologists and cardiac electrophysiologists. Present approaches to data interpretation and understanding, and practical limitations on time and physician availability, make such analyses impracticable.

Conventional systems for collecting and analyzing pacemaker and ICD telemetered signals in a clinical or office setting can be used to retrieve data, such as patient electrocardiogram and any measured physiological conditions, collected by the IPG for recordation, display and printing. The retrieved data may be displayed in chronological order and analyzed by a physician. Conventional systems often lack remote communications facilities and must be operated with the patient present. These systems present a limited analysis of the collected data based on a single device interrogation and lack the capability to recognize trends in the data spanning multiple episodes over time or relative to a disease specific peer group.

SUMMARY OF THE INVENTION

The present invention is directed to systems, devices, and methods for transporting medical information over a network. Embodiments of the present invention are directed to methods of transporting medical information across a network configured to service a multiplicity of geographical locations. Methods of the invention involve querying the network by a portable source medical device that is movable relative to the geographical locations, and determining communication links of the network presently available to effect communications between the source medical device and a target component when the source medical device is at each of the geographical locations. A profile is generated comprising information about each of the available communication links and attributes associated with each of the available communication links for each of the geographical locations. Each of the profiles is stored in the source medical device. Methods of the invention involve accessing, when the source medical device is at a particular geographical location, a particular profile stored in the source medical device that is associated with the particular geographical location, establishing a network connection between the source medical device and the target component using a communication link associated with the particular profile, and transferring medical information between the source medical device and the target component via the communication link associated with the particular profile.

System embodiments of the present invention provide for transporting medical information across a network configured to service a multiplicity of geographical locations. System embodiments of the invention include a source medical device configured for portability relative to the geographical locations. The source medical device comprises or is coupled to a mapping agent and a profile library. The mapping agent includes a processor configured to execute program instructions for querying the network and determining communication links of the network presently available to effect communications between the source medical device and a target component when the source medical device is at each of the geographical locations. The processor is configured to execute program instructions for generating a profile comprising information about each of the available communication links and attributes associated with each of the available communication links for each of the geographical locations, and to store each of the profiles in the profile library. The processor is configured to execute program instructions for accessing, when the source medical device is at a particular geographical location of the plurality of geographical locations, a particular profile stored in the source medical device that is associated with the particular geographical location, establishing a network connection between the source medical device and the target component using a communication link associated with the particular profile, and transferring medical information between the source medical device and the target component via the communication link associated with the particular profile.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1A is a system diagram of a life critical network implementation in accordance with embodiments of the present invention;

FIG. 4 illustrates a PPC having a reduced feature set and a relatively small form factor in accordance with embodiments of the present invention;

Figure 1B:
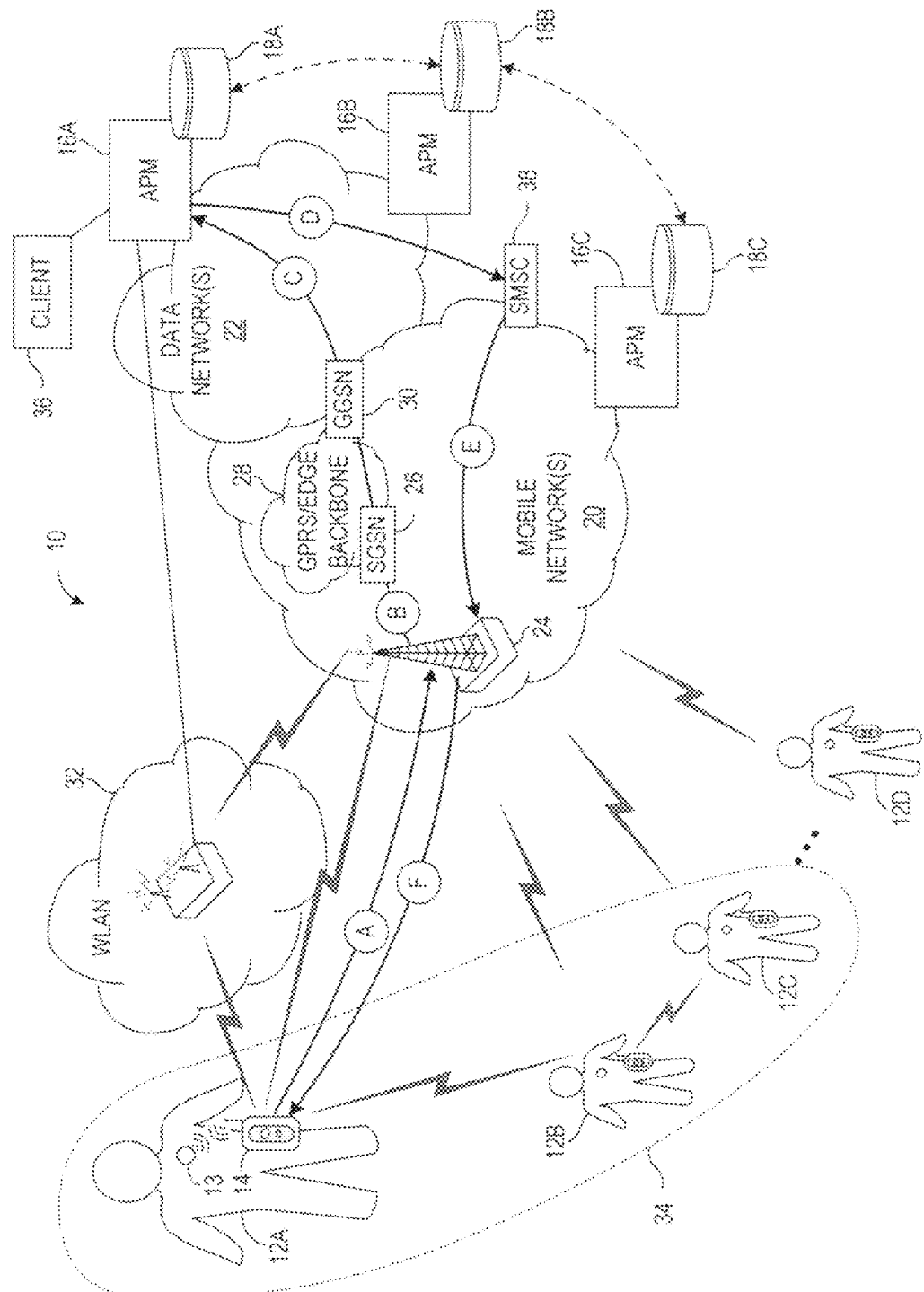
FIG. 1B illustrates an exemplary automated or advanced patient management or monitoring (APM) environment supported within a life critical network in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such a device or system need not include all of the features described herein, but may be implemented to include selected features that provide for useful structures, systems, and/or functionality.

A life critical network of the present invention is preferably configured as a robust network supported by existing mobile and data networks, and exhibiting heightened communication attributes such as guaranteed delivery, high quality of service (QoS), and tight security. A life critical network implemented in accordance with the present invention provides for the acquisition of physiologic and contextual data acquired for any number of patients that are each carrying a portable communications device, referred to herein interchangeably as a portable patient communicator (PPC) or patient communicator (PC).

Acquisition of physiologic data by a remote server of the life critical network for individual patients may advantageously occur on an unscheduled basis, such as in response to predefined events (e.g., tachycardia events) or in response to patient initiated interrogations. In this regard, a life critical network may acquire patient data for any number of patients that carry a PPC on an event-driven basis, in contrast to a time-scheduled basis.

Remote server acquisition of patient physiologic data may occur while the patient is ambulatory, such as during daily routines at the home or office, or when traveling locally, nationally or worldwide. Physiologic data for patients may be acquired by a wide variety of sensors, including external and internal sensors. For example, an implantable medical device, such as a pacemaker or ICD, may acquire physiologic data and transmit such data to the PPC.

Data acquired by the PPC may be transmitted to a remote server of the life critical network in real-time, such as by use of a real-time data streaming protocol. Store-and-forward data transfer protocols may also be employed, such as for less critical data or when a real-time data transfer connection is not available. Incremental data transfers may also be performed to reduce the volume of data transferred from the PPC to the remote server. A life critical network of the present invention provides connectivity between a patient's PPC and remote server that can be dynamically adjusted to meet the needs of the patient, physician, emergency services, and system/technical personnel.

Real-time transfer of patient physiologic data may be triggered by real-time clinical events detected by a sensor or implantable medical device provided with the patient. Data transfers may also be triggered in accordance with query/response protocols. Clinical alerts for high risk patients may be communicated through the life critical network in real-time. Physiologic monitoring for remote triage may be implemented in real-time through the life critical network.

Examples of patient data that may be transferred from the PPC to the remote server include electrograms (EGMs), clinical event data, episode counters, alerts, device or sensor settings, battery status, lead measurements, and patient activity level, among other types of data. Data transferred from the PPC to the remote server may be integrated at a web site supported by the remote server and displayed at a remote location (e.g., physician's office).

Notification of data delivery and/or alerts from the PPC to the patient's physician, an EMT or patient advocate, for example, may be implemented by a telephone call from the life critical networks service, a fax, email or SMS message, among other modes of communication. Other forms of patient/server interaction facilitated by the life critical network include medication management and remote interrogation or programming of the sensor or implantable medical device.

A PPC implemented in accordance with the present invention facilitates acquisition of patient sensor or implantable medical device data by a remote system for ambulatory patients. A PPC of the present invention is preferably configured to communicate wirelessly over existing mobile and data networks, and to effect local wireless communication with one or more internal and/or external physiologic sensors, ambient and/or contextual sensors, implantable medical devices, and/or other external systems or devices.

A PPC of the present invention may be implemented to provide a wide spectrum of capabilities and functionality. For example, the PPC may be configured to provide only a limited number of features, such as in the case of a PPC having a reduced feature set. By way of further example, a PPC may be implemented to provide a variety of features and capabilities that enable a wide range of functionality.

A PPC implemented in accordance with embodiments of the present invention may be dynamically configurable via interaction with a remote server of a patient management system and/or an implantable medical device or system. Dynamically altering the configuration of a PPC serves to enhance cooperative operation between the PPC, implantable medical device/sensor, and networked patient management system, an embodiment of which is referred to herein as an advanced patient management system or server. Illustrative examples of an APM system include a remote patient monitoring system and a patient monitoring system that need not be remote relative to the patient's location. Dynamically altering the configuration of a PPC may also serve to conserve power of the implantable medical device or sensor(s) that are communicatively coupled to the PPC.

A life critical network coupling a patient implantable medical device (PIMD) with an APM server via a PPC provides the opportunity for increased interaction between the patient and various network components and services. Mobile cellular connectivity of the portable communication device facilitates a variety of interactions between the patient and the APM system, between the patient and the PIMD-PPC pair, and/or between the patient or PIMD-PPC pair and other services accessible via the mobile cellular network.

Exemplary services that may be provided through use of the PIMD-PPC pair involve medication management for the patient, medication schedule compliance tracking, exercise schedule compliance tracking, and/or periodic physiological test compliance tracking, compliance tracking of prescribed external therapies (e.g., patient use of CPAP or oxygen therapies), prescription refills, and/or information relayed to the patient's physician, patient advocate or APM server if patient activity, exercise or physiological tests indicate a change that needs attention.

The PPC and/or server may generate reminders to the patient to perform some action, such as taking medication, perform a home-based diagnostic test, exercise, or use an external therapy device. The patient reminders may be based on a particular time schedule or may be event-driven based on the physiological condition of the patient. A physician monitoring the patient may prescribe the regimen of exercise (e.g., exercise frequency or duration), and other types of activities, including those listed above, for example, and the patient reminders may be based on patient compliance with the prescribed regimen.

The functionality provided by reminder schedules, medication schedule or activity tracking may provide incentives for a patient to stay communicatively coupled to the network, allowing for a higher level of care.

The ability of the PIMD-PPC pair to provide event-driven updates, real-time waveform viewing and nearly instantaneous command access to the PIMD for modifying device parameters facilitates remote interrogation, testing, and PIMD programming through the life critical network.

Embodiments of the invention contemplate the involvement of application-specific network solutions, as well as exploiting existing and future network technologies. Patients are equipped with a PPC capable of carrying out wireless communications over existing data networks. Device and network attributes can also be modified and/or controlled to provide a "life critical network" by which the communication of vital patient information can approach guaranteed, secure delivery.

It may be unnecessary, impractical or otherwise undesirable to restrict patients to physical areas where equipment is located to facilitate information communication with patient management services. In many cases, the patient's condition or health does not restrict the patient from normal daily activities, or at least from activities that would separate the patient from fixed equipment used to communicate with patient management services. Solutions provided by the invention advance patient mobility by enabling wireless communication of data, commands and/or other information between patient devices and patient management systems. By furnishing the patient with such mobile communication equipment, communication can be effected periodically or semi-continuously, at any needed time or place.

FIG. 1A is a system diagram of a life critical network implementation in accordance with embodiments of the present invention. The network implementation shown in FIG. 1A includes multiple components linked together to provide a specialized network that guarantees secure and timely delivery of data that are transmitted over one or more networks and attempts to meet specific context sensitive criteria on delivery of that data.

The life critical network (LCN) 200 essentially provides a private network that is configured to operate on top of existing mobile and fixed facility networks. The LCN 200 utilizes a secured architecture providing for authentication and management of those components that are allowed access to the network 200. Such components or nodes include, for example, portable patient communicators 14, patient sensors 17A-17B, PIMD programmer systems 23, clinician mobile devices 25, clinician workstations 27, patient advocate mobile devices 21, and smart hubs 19, among others.

The LCN 200 preferably follows cryptographic best practices with regard to confidentiality, integrity, and availability. Given the computational-versus-power requirements, the LCN system 200 can minimize the number of asymmetric cryptographic operations in favor of a symmetric algorithm based on various factors, including a known shared-secret generated or installed at time of manufacture, and a dynamically shifting key based on a seed fed to a pseudo random number generator (e.g., such as model, serial number, and network time).

The LCN system 200 preferably leverages the physical network as a virtualized transport, essentially treating any underlying protocol as potentially unsecured, and thus not relying on any native security mechanisms inherent in any given protocol with regard to the encryption and integrity of its data. The LCN system 200 preferably supports both stateful and stateless connections in order to facilitate asynchronous communication where network bandwidth does not support real-time communication.

The LCN 200, as shown in the embodiment of FIG. 1A, employs a central authority 16 to manage access to the network infrastructure. This involves cryptographically validating and authenticating content from a potential node prior to allowing access, and performing other control aspects of policing the network infrastructure. The LCN 200 preferably supports the concept of classification of nodes on the network 200 into a specific hierarchy of access abilities. The various entities requesting access to the LCN 200 are granted different access rights based on their classification. For example, a low-urgency sensor device 17A-17B may not be given access to high-speed connectivity if it is classified in a lower urgency or priority tier. A patient implantable medical device programming system 23 may be granted priority access to a higher speed connectivity capability due to its more demanding need for timely interconnection to the infrastructure. This classification and prioritization is preferably dynamically managed via the central authority 16.

One aspect of creating and maintaining an LCN 200 in accordance with the present invention is the ability to dynamically map the available connectivity options between nodes in the network 200. This process is an important capability to providing the optimum resources for the network infrastructure as well as defining various profiles for communication.

The process of mapping the environment at the source end of the network 200 begins by the source agent performing a series of queries and/or connection attempts via various methods to build potential temporal and spatial profiles. In various embodiments, the device performing the mapping may employ multiple forms of both wired and wireless communications. The communication mechanisms may include, but are not limited to, the following: RF Wireless Transceivers (WiFiMax, IEEE 802.11a/b/g/n, etc.); Cellular Network Transceivers (GSM, EDGE, GPRS, CDMA, etc.); Bluetooth (high or low power methods); Zigbee (IEEE 802.15.4); Wired Ethernet (IEEE 802.3); Plain Old Telephone System (POTS)/Public Switched Telephone Network (PSTN); Emergency Systems (e.g., 911, WPS); TDD, SMS, MMS, EMS, and VOIP, among others.

The mapping determines the most efficient and most reliable connection options that are present in the current location of the source device. Because network connections are not always stable, the mapping process attempts to survey all of the currently available connection options. A profile maintains these options and lists various attributes of the connectivity methods found. These attributes could, for example, include the following: signal type; signal strength; provider name; preferred network provider information; encryption options available; and compression options available, among others.

Once the environment has been mapped, the measured results are then prioritized into a list of connection options of the highest bandwidth, with the most robust and secure option first on the list and then descending towards less secure and robust options. Not all options are available or viable in a specific environment. As a result, the list is populated with only those connections that meet the required connectivity requirements.

The mapping agent has the capability for creating and managing multiple profiles per user per device. The ability to create different profiles based on the patient location allows the LCN nodes the ability to have multiple sets of connection options that are dynamically selected based on the location of the patient. The decision to create a new profile can be autonomously decided by the source user device due to the device sensing a new location/environment for a specified timeframe or via direct interaction with the user. Many types of environments may exist for the user—at the users residences (e.g., home, office, hospital, etc), at a mobile location (e.g., transit options including car, rail, planes, marine, etc.).

The LCN system 200 may employ a peer-to-peer or ad hoc network profile, where devices brought within range of one another may elect to leverage a profile of the other device in order to pass information up to the system, in particular sensors may utilize a node hopping approach. The condition where there are no viable connectivity options available is realistic, so in this case the source device preferably has means (electronic or non-electronic) of conveying some aspect of the lack of connectivity to the user directly. This may be via various physical means including but not limited to vibration, lighting an indicator, audio outputs, etc.

The connection between LCN nodes, once established, is used to transfer data securely between a source and a target. In various embodiments, the source end represents a medical device that is used to communicate data and diagnostic information from other medical devices in a patient's environment. These data may originate from medical devices taking the form of implantable medical devices (ICD, CRT-D, pacemakers, nerve stimulators, drug delivery devices and pumps, etc.), or sensor devices both external to the patient (e.g., a weight scale or a blood pressure monitor) and implantable sensors (e.g., pressure sensors, blood chemistry, temperature, etc.).

These data components have varying attributes associated with them, specifically, the basic attributes of size and context. However, there also is a concept of urgency/priority. The source component can provide this urgency/priority as a guide for determining how data is transmitted via the LCN 200. For example, if the data retrieved was of high urgency and criticality, the source component could use a higher performing transmission capability of the LCN 200 to ensure that the urgent content is sent to the target in the most efficient way. This concept would also be used as part of the prioritization as to how the LCN profile would be traversed.

The target component commonly is a computer system that provides the ability to store the retrieved content sent from the source. The use of the LCN 200 enables two-way communication between the source and target nodes. The data content being sent from the target to the source can have many contexts. Specifically, the data could contain configuration information for a node or software updates, as well as any system connectivity updates (e.g., protocol updates, network infrastructure updates, approved provider lists, etc.)

Alternative methods for data transmission over the LCN 200 may involve data parsing based on criticality of data or multicasting data via several channels at once. According to some embodiments, the source nodes in the LCN system 200 may choose to parse data into various categories based on urgency and use different methods based on the categorization. An example of this capability involves a required data upload for a medical device where the raw medical device data is sent via fast communication channels, and statistical information may be sent along a slower, less urgent communication channel. This capability allows the source node the ability to tailor use of the LCN infrastructure 200 due to business needs, while still maintaining the critical aspects of the medical device content.

According to other embodiments, there may be conditions where urgent content needs to be sent to a target and the sending node sends the content across multiple communication methods to assure that the data is received by the target node. This allows the target to receive the data from multiple methods and reconstruct the message if partial messages are received.

Figure 1C:
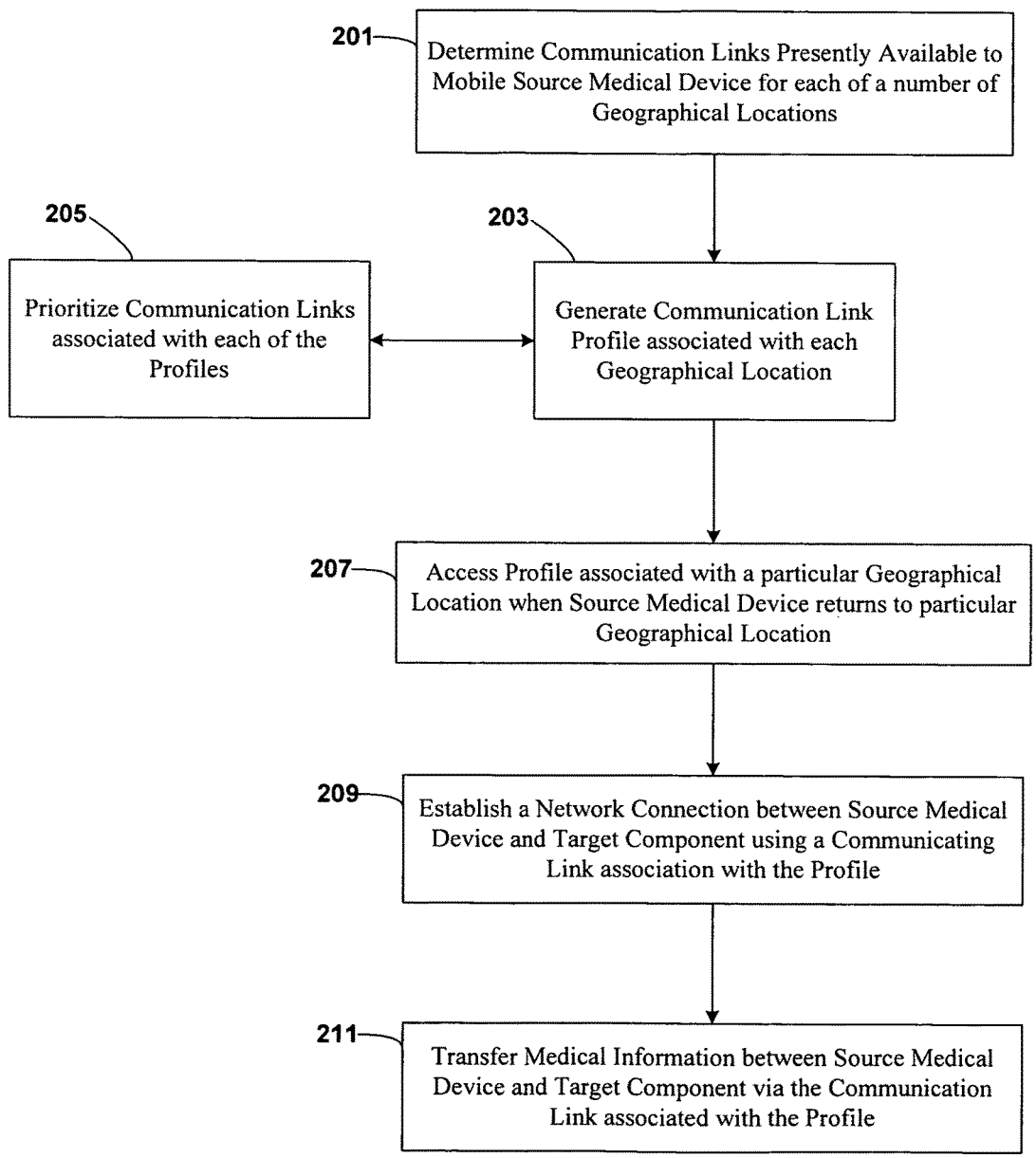
FIG. 1C is a flow diagram illustrating various processes of a dynamic communication link mapping methodology for optimizing connectivity between source medical devices and a target component in accordance with embodiments of the present invention.

Turning to FIG. 1C, there is shown a flow diagram illustrating various processes of a dynamic communication link mapping methodology for controlling connectivity between portable and stationary source medical devices and a target component in accordance with embodiments of the present invention. A challenge presented by implementing a network topology concerns the cost of making and using network connections (of various types) to facilitate communication of medical information between a mobile source medical device and a target component, such as a central authority that provides access to a patient management server system.

It is appreciated by those skilled in the art that the cost of "discovering" available network communication mechanisms (both wireless and wired) by a source device is greater than the cost of "using" a network connection. This cost can be characterized in terms of data transmission, time of transmission, battery consumption, processor usage, etc. In the context of a mobile source medical device, such as a PPC, numerous discovery operations would have to be performed as the patient with the mobile source medical device moves about town or the country, for example. It can be appreciated that, as the patient/source medical device moves about geographically, wireless and wired network services change. Also, network connections can unpredictably change in terms of quality, guarantee of service, and bandwidth, for example.

These and other scenarios necessitate repeated and expensive discovery operations in order to maintain network connectivity and a desired level of service between a mobile source medical device and a target component. A dynamic communication link mapping methodology for controlling connectivity between portable and stationary source medical devices and a target component in accordance with embodiments of the present invention provides for a substantial reduction in the occurrence and aforementioned cost of discovery operations performed by such source medical devices.

According to the embodiment shown in FIG. 1C, queries are made by a source medical device to determine 201 communication links of the network that are presently available to effect communications between the source medical device and a target component when the source medical device is at each of the geographical locations. Generally, the source medical device is a portable or mobile medical device, but may also be a stationary device or system.

A profile is generated 203 that includes information about each of the available communication links and various attributes associated with each of the available communication links for each of the geographical locations. Generating the profiles 203 may also involve a prioritization methodology, by which the available communication links associated with each of the profiles are prioritized 205 in a desired manner. The generated and prioritized profiles are stored in the source medical device.

The embodiment shown in FIG. 1C further involves accessing 207, when the source medical device is at a particular geographical location, a particular profile stored in the source medical device that is associated with the particular geographical location. A network connection is established 209 between the source medical device and the target component using a communication link associated with the particular profile. Medical information is transferred 211 between the source medical device and the target component via the communication link associated with the particular profile.

According to various embodiments, the communication link associated with the particular profile that is used to establish the connection with the network is selected based on the prioritization 205 of the communication links. Prioritization of the communication links may be based at least in part on one or more factors concerning the communication link, such as bandwidth, integrity, and security. Other factors upon which prioritization of the communication links may be based include quality of service and level of guaranteed delivery. Prioritization of the communication links may based at least in part on factors such as cost, profile of a user of the source medical device, and particulars of a service agreement that defines financial and usage terms as between the user of the source medical device and a central authority of the network. Other prioritization factors include priority or urgency of the medical information (e.g., criticality of the information or patient condition). Still other factors upon which prioritization of the communication links may be based include type of source medical device, such as type of implantable cardiac rhythm management device, physiologic sensor, or patient sensor. It is understood that any one or combination of these and other factors may be used to facilitate prioritization of the communication links presently available to a source medical device.

In other embodiments, capabilities of one or both of the communication link and target component services may be selectively enabled and disabled based on various factors. Such factors may include a profile of a user of the source medical device and particulars of a service agreement that defines financial and usage terms as between the user of the source medical device and a central authority of the network. Enablement, disablement, and/or adjustment of capabilities of one or both of the communication link and target component services is preferably effected by the central authority (e.g., a processor(s) of the central authority executing program instructions to effect changes in capabilities and/or services).

According to some embodiments, the target component comprises a central authority of the network. The central authority is typically configured to coordinate establishment of a communication path via nodes of the network having attributes indicated by the particular profile. Preferably, the profiles are generated by the source medical device. In some embodiments, the profile is generated at least in part by the target component, such as the central authority. For example, the central authority could generate a default profile, such as a profile that encompasses business rules (e.g., one particular connection mechanism may be cheaper than another).

As is shown in block 207 of FIG. 1C, a profile associated with a particular geographical location is accessed when a source medical device returns to the particular geographical location. Determining the geographical location of the source medical device may be accomplished using known network implemented locating mechanisms (e.g., cellular tower-based triangulation, GPS, manual user entry, IP address (Geolocation), NITZ, cell tower identification). Determining the geographical location of the source medical device may be accomplished using a mechanism other than a network implemented locating mechanism, such as by use of a GPS sensor, which may be a separate device or a sensor integral to the source medical device.

It is noted that most routing protocols include the notion of a timer that ticks down (expires) after which a refresh occurs. A profile based on geo-location can be used to aid with "hinting" to the type, number, and potential quality of network paths. For example, it can be "noticed" when the source medical device is moved closer to a couple of towers and other signaling sources, such as when the patient is in town on a Sunday. This kind of information can be observed and provide feedback to network selection and transmission timing opportunities for potentially for large-bandwidth important (but generally not critical) information upload. Most of this cost metric would be dependent on sample frequency and available profile memory.

Figure 1D:
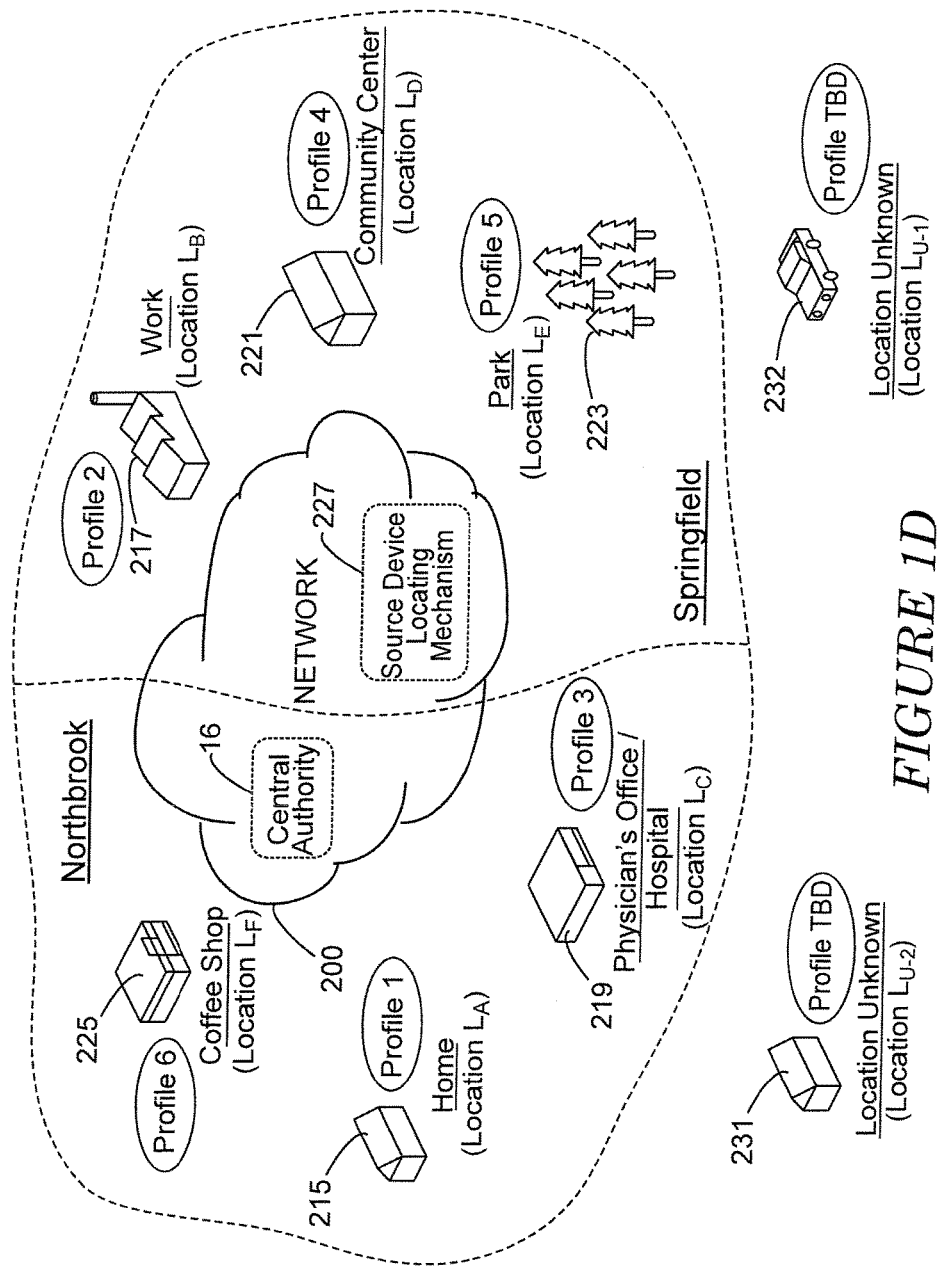
FIG. 1D is a system diagram of the life critical network that supports a dynamic communication link mapping methodology in accordance with embodiments of the present invention.

FIG. 1D is a system diagram of the life critical network 200 that supports a dynamic communication link mapping methodology in accordance with embodiments of the present invention. In FIG. 1D, a geographic region is shown that includes two cities, Northbrook and Springfield. A patient, in this illustrative example, lives in Northbrook (home 215), works in Springfield (work 217), and visits several destinations on a regular basis both in Northbrook and Springfield (doctor's office/clinic 219; community center 221; park 223; and coffee shop 225). The patient is also shown visiting a new location (a new restaurant 231) in another city and taking a road trip in a car 232. The known locations are designated in FIG. 1D as locations $L_A$ through $L_F$, and the two unknown locations are designated as locations $L_{U-1}$ and $L_{U-2}$.

In accordance with the processes shown in FIG. 1C and as discussed above, a profile for the available communication links at each of locations $L_A$ through $L_F$ is originally established when the patient first visits these locations. These profiles (profiles 1-6 corresponding to locations $L_A$ through $L_F$) are stored in the patient's portable source device. A source device locating mechanism 227 of the network locates the geographic location of the patient. Alternatively, or in cooperation with source device locating mechanism 227, the location of the patient's portable source device may be determined using a GPS sensor, which may be integral or coupled to the patient's portable source device. When the patient returns to each of locations $L_A$ through $L_F$, as determined by the locating mechanism 227 (or GPS sensor), the pre-established profile (e.g., profile 1-6) associated with the patient's present location is used by the source medical device to establish connectivity with the network 200 and the target component (e.g., patient management server system).

Profiles (indicated as TBD) for previously unknown locations $L_{U-1}$ and $L_{U-2}$ are generated in a manner described in FIG. 1C. Once generated, the profiles for locations $L_{U-1}$ and $L_{U-2}$ are stored in the source medical device. The stored profiles associated with each of the locations $L_{U-1}$ and $L_{U-2}$ are used by the source medical device to establish connectivity with the network 200 and the target component when the patient returns to locations $L_{U-1}$ and $L_{U-2}$, as determined by the locating mechanism 227 or other locating mechanism.

It is noted that profiles associated with known destinations/locations may be updated to ensure that connectivity information for a given location remains current. This may entail automatic initiation of a discovery procedure by the source medical device in accordance with a pre-established schedule (e.g., once per week or month) or upon detection of an appreciable reduction in successful network connections being made using higher priority connection options.

Communication link profiles may be generated for regular destinations/locations visited by a patient in a number of ways. The patient may actuate a button on the source medical device when the patient is at a regular destination, which manually establishes this location as one that the patient regularly visits. The geographic location and the profile generated for this location resulting from patient actuation of an appropriate button are stored in the source medical device.

Profiles may also be established automatically by the source medical device or the central authority 16. According to one approach, the source medical device employs a timer to determine the how long the patient remains within a relatively small geographical location (e.g., a community center 221 or coffee shop 225). Patient dwell time can be measured, and if the dwell time exceeds a threshold (e.g., >1 hour) on a repeated basis, then this location may automatically be designated a "regular destination." The geographical location and the profile generated for this location as determined/created automatically are stored in the source medical device.

Table 1 below illustrates a profile library that includes a number of communication link profiles associated with several different geographical locations depicted in FIG. 1D (Home location $L_A$ and Work location $L_B$, in particular). This library is preferably stored in non-volatile memory of the source medical device.

Each of the locations has associated profiles, identified by profile number. Each of the profiles is associated with a multiplicity of connection options (indicated as $C_1$-$C_N$). Typical connections include: RF Wireless Transceivers (Wi-FiMax, IEEE 802.11a/b/g/n, etc.); Cellular Network Transceivers (GSM, EDGE, GPRS, CDMA, etc.); Bluetooth (high or low power methods); Zigbee (IEEE 802.15.4); Wired Ethernet (IEEE 802.3); Plain Old Telephone System (POTS)/Public Switched Telephone Network(PSTN); Emergency Systems (e.g., 911, WPS); TDD, SMS, MMS, EMS, and VOIP, among others.

Each of the connection options is associated with a multiplicity of attributes (indicated as $A_X$ for each connection option $C_Y$). Typical connection attributes include, for example, quality of service (QoS); bandwidth; integrity or robustness; security; level of guaranteed delivery; cost; and attributes that can limit features and access, such as by enabling and disabling communication link and/or target component services. It will be understood that communication link profiles may include information other than that shown in Table 1 and may be organized in a variety of ways differing from that shown in Table 1 below.

TABLE 1

| Location | Profile Number | Connection Option | Attributes |
|---|---|---|---|
| $L_A$ (Home) | Profile $1_{LA}$ | $C_{1\text{-}P1}$ | $A_1\text{-}C_1$ |
|  |  |  | $A_2\text{-}C_1$ |
|  |  |  | . |
|  |  |  | . |
|  |  |  | . |
|  |  |  | $A_N\text{-}C_1$ |
|  |  | $C_{2\text{-}P1}$ | $A_1\text{-}C_2$ |
|  |  |  | $A_2\text{-}C_2$ |
|  |  |  | . |
|  |  |  | . |
|  |  |  | . |
|  |  |  | $A_N\text{-}C_2$ |
|  |  | . |  |
|  |  | . |  |
|  |  | . |  |
|  |  | $C_{N\text{-}P1}$ | $A_1\text{-}C_3$ |
|  |  |  | $A_2\text{-}C_3$ |
|  |  |  | . |
|  |  |  | . |
|  |  |  | . |
|  |  |  | $A_N\text{-}C_3$ |
|  | Profile $2_{LA}$ | $C_{1\text{-}P2}$ | $A_1\text{-}C_1$ |
|  |  |  | $A_2\text{-}C_1$ |
|  |  |  | . |
|  |  |  | . |
|  |  |  | . |
|  |  |  | $A_N\text{-}C_1$ |
|  |  | . |  |
|  |  | . |  |
|  |  | . |  |
|  |  | $C_{N\text{-}P2}$ | $A_1\text{-}C_N$ |
|  |  |  | $A_2\text{-}C_N$ |
|  |  |  | . |
|  |  |  | . |
|  |  |  | . |
|  |  |  | $A_N\text{-}C_N$ |
|  | . |  |  |
|  | . |  |  |
|  | . |  |  |
|  | Profile $N_{LA}$ |  |  |
|  | . |  |  |
|  | . |  |  |
|  | . |  |  |
| $L_B$ (Work) | Profile $1_{LB}$ | $C_{1\text{-}P1}$ | $A_1\text{-}C_1$ |
|  |  |  | $A_2\text{-}C_1$ |
|  |  |  | . |
|  |  |  | . |
|  |  |  | . |
|  |  |  | $A_N\text{-}C_1$ |
|  |  | . |  |
|  |  | . |  |
|  |  | . |  |
|  |  | $C_{N\text{-}P1}$ | $A_1\text{-}C_N$ |
|  |  |  | $A_2\text{-}C_N$ |
|  |  |  | . |
|  |  |  | . |
|  |  |  | . |
|  |  |  | $A_N\text{-}C_N$ |
|  |  | $C_{1\text{-}PN}$ | $A_1\text{-}C_1$ |
|  |  |  | $A_2\text{-}C_1$ |
|  |  |  | . |
|  | . |  | . |
|  | Profile $N_{LB}$ |  | . |
|  |  |  | $A_N\text{-}C_1$ |
|  |  |  | . |
|  |  |  | . |

TABLE 1-continued

| Location | Profile Number | Connection Option | Attributes |
|---|---|---|---|
|  |  | $C_{N\text{-}PN}$ | $A_1\text{-}C_N$ |
|  |  |  | $A_2\text{-}C_N$ |
|  |  |  | . |
|  |  |  | . |
|  |  |  | $A_N\text{-}C_N$ |
| . |  |  |  |
| . |  |  |  |
| $L_N$ (Location N) | . | . | . |
|  | . | . | . |
|  | . | . | . |

Figure 1E:
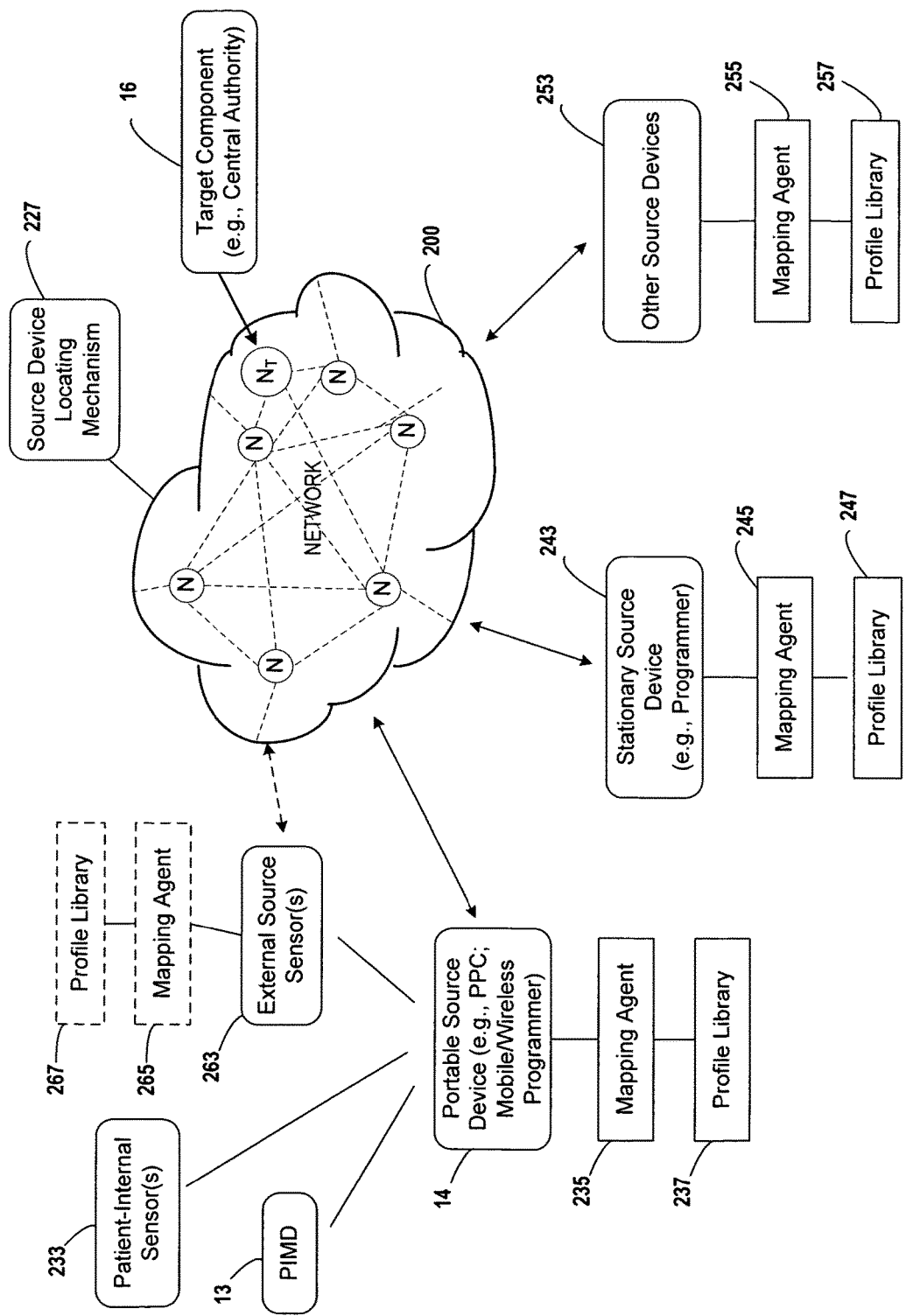
FIG. 1E shows aspects of source medical devices that respectively communicate with a target component via a life critical network that supports a dynamic communication link mapping methodology in accordance with embodiments of the present invention.

FIG. 1E shows aspects of source medical devices that respectively communicate with a target component via a life critical network that supports a dynamic communication link mapping methodology in accordance with embodiments of the present invention.

A portable source device 14 is shown communicatively coupled to a network 200 which includes a multiplicity of nodes N and a target node NT that represents a target component 16, such as a central authority or patient management server system. The portable source device 14 is coupled to, and preferably incorporates, a mapping agent 235 and a profile library 237. The mapping agent 235 preferably employs a processor configured to execute program instructions for discovering available communication links of the network 200 and obtain connection information, including connection options and connection attributes, from the discovery operation. The mapping agent 235 preferably employs a processor configured to execute program instructions for creating profiles containing information about each of the available communication links and various attributes associated with each of the available communication links for each of the geographical locations. This information is stored in the profile library 237, such as in a format depicted in Table 1 above.

FIG. 1E further shows a stationary source device 243 and other source devices 253 (mobile or stationary), each of which is coupled to, or incorporates, a mapping agent 245, 255 and a profile library 247, 257, which operate in a manner discussed above. Certain external source sensor 263 may have dedicated or shared mapping agents 265 and profile libraries 267 (e.g., weight scale, blood chemistry sensor, blood pressure monitor). Other external source sensors 263 may be configured to share the mapping agent and profile library resources of the portable source device 14.

The portable source device 14 is shown communicatively coupled to a PIMD 13, one or more patient-internal sensors 233, and one or more external source sensors 263. In the configuration shown in FIG. 1E, these devices 14, 13, 233, 263 may each utilize the mapping agent 235 and profile library 237 of the portable source device 14. In this case, the profile library 237 will include information similar to that shown in Table 1. Because different types of devices and information derived from same share common mapping agent and profile library resources, each of these devices/data streams are preferably identified by source and status. For example, the PIMD 13 and data acquired by same will enjoy a higher status relative to an external sensor 263, such as a blood pressure sensor. This difference in status results in different connection options and attributes for each of the disparate devices. This information is maintained in the profile library 237 so that the transport of data obtained by each of these devices is properly managed.

Embodiments of a dynamic communication link mapping methodology of the present invention may be employed to facilitate enhanced communication of medical information in the context of automated patient management. Automated patient management involves numerous activities, including remote patient monitoring and/or management and automatic diagnosis of the device and/or patient health. FIG. 1B illustrates an exemplary automated or APM environment 10 supported by the present invention. Each patient 12A, 12B, 12C, 12D involved with the APM environment is associated with one or more data sources or medical devices 13 (hereinafter medical devices) associated with that patient. These medical devices 13 include, for example, medical therapy devices that deliver or provide therapy to the patient 12A, medical sensors that sense physiological data in relation to the patient 12A, and measurement devices that measure environmental parameters occurring independent of the patient 12A.

Each patient medical device 13 can generate one or more types of patient data and can incorporate one or more components for delivering therapy, sensing physiological data and measuring environmental parameters. Representative medical devices include patient implantable medical devices (PIMDs) such as pacemakers, implantable cardiac defibrillators, drug pumps, neuro-stimulators and the like. External medical devices may also be paired with the PPC, such as automatic external defibrillators (AEDs). The medical devices may also include implantable or external sensors. Implantable sensors include, for example, heart and respiratory monitors, implantable diagnostic multi-sensor non-therapeutic devices, etc. External sensors may include Holter monitors, weight scales, blood pressure cuffs, temperature sensors (e.g., digital thermometers and cutaneous temperature sensors), ECG and/or heart rate sensor, gas sensors for sensing oxygen and carbon dioxide concentration via a respiratory mask, such as a CPAP mask, drug dispensers or pill counters, etc. Other types of medical, sensing, and measuring devices, both implantable and external (e.g., drug delivery devices), are possible.

Each patient 12A, 12B, 12C, 12D involved with the APM environment is also associated with at least one PPC 14 (e.g., "source medical device" as shown in FIGS. 1A and 1E) capable of wirelessly communicating information with an APM system represented by one or more APM servers 16A, 16B, 16C (e.g., "target components" as depicted in FIGS. 1A and 1E). Each APM server may include a database 18A, 18B, 18C to store information such as patient data, device/sensor configuration and diagnostic data, PIMD and PPC power status and usage data, LCN connection data, and the like. The APM server arrangement may be implemented in a single server/database 16A/18A, or may include multiple servers and databases as depicted in FIG. 1B. Further, the APM server arrangement may include multiple servers and associated databases operating substantially independently. In such a case, information may be exchanged between any of the APM servers through information requests and responses. Alternatively multiple servers and databases may operate as a distributed server/database system to collectively serve as a single APM system.

Each PPC 14 is uniquely assigned to a particular patient 12A, preferably through a process generally referred to herein as "pairing" in accordance with various embodiments. As used herein, pairing generally refers to the unique association created between the patient's PPC 14 and the medical device(s) 13 associated with that patient. When information is to be transmitted between the medical devices 13 and an APM server 16A, the PPC 14 paired with a respective medical device(s) 13 serves to wirelessly communicate the information over one or more networks. In one embodiment, the PPC 14 communicates by way of a mobile network(s) 20, such as a cellular network. A cellular network generally refers to a radio network made up of numerous cells generally defined by a transmitter or "base station." Each base station provides coverage for an area defining its respective cell, and the collective cell structure thus provides radio coverage over a wider area. The mobile network(s) 20 may represent any one or more known or future wireless networking technologies, such as the Global System for Mobile Communications (GSM), Universal Mobile Telecommunications System (UMTS), Personal Communications Service (PCS), Time Division Multiple Access (TDMA), Code Division Multiple Access (CDMA), Wideband CDMA (WCDMA), or other mobile network transmission technologies.

In one embodiment of the invention, the PPC 14 communicates wirelessly via a GSM network. Data may be communicated via a General Packet Radio System (GPRS) mobile communications network, where GPRS refers to a packet-switched service for GSM that mirrors the Internet model and enables seamless transition towards advanced generation networks. GSM/GPRS networks have further evolved to provide increased data transfer rates over the network. For example, one embodiment of the invention exploits the Enhanced Data rates for GSM Evolution (EDGE), which is also known as Enhanced GPRS (EGPRS). EDGE is a digital mobile technology that allows for increased data transmission rates and reliability, and is essentially a "bolt on" enhancement to second generation GSM and GPRS networks. Further enhancements to EDGE networks, such as "EDGE Evolution," provides even further increases in data rates, error correction and signal quality.

Data communicated between the PPC 14 and the mobile network(s) 20 is ultimately communicated with the APM server 16A. As previously indicated, the APM server 16A may or may not be associated with one or more other discrete or distributed server/database systems 16B/18B, 16C/18C, etc. One or more data networks 22 may cooperatively operate with the mobile network(s) 20 to facilitate data transfers to and from the relevant APM server 16A. For example, the illustrated data network 22 may represent the Internet, which interfaces to the illustrated EDGE or other mobile network 20 to serve landline APM server systems.

The patient communication 14 communicates with a component of a cellular infrastructure. For example, the PPC 14 may communicate with a base station 24 via an air interface. The base station 24 represents a component of the wireless network access infrastructure that terminates the air interface over which subscriber traffic is communicated to and from the PPC 14. A Base Station Controller (BSC) (not shown) is a switching module that provides, among other things, handoff functions, and controls power levels in each base station. The BSC controls the interface between a Mobile Switching Center (MSC) (not shown) and base station 24 in a GSM/GPRS or EDGE mobile network 20, and thus controls one or more base stations 24 in the set-up functions, signaling, and in the use of radio channels.

A BSC also controls the interface between the Serving GPRS Support Node (SGSN) 26 and the base station 24 in such a mobile network 20. The SGSN 26 serves a GPRS or EDGE-equipped mobile by sending or receiving packets via the base station 24 at the mobile interface of the GPRS/

EDGE backbone network 28. The SGSN 26 can manage the delivery of data packets to and from the PPC 14 within its service area, and performs packet routing and transfer, mobility management, logical link management, authentication, billing functions, etc. In the exemplary GPRS/EDGE embodiment shown in FIG. 1B, the location register of the SGSN 26 can store location information such as the current cell and Visiting Location Register (not shown) associated with the PPC 14, as well as user profiles such as the International Mobile Subscriber Identity Number (IMSI) of all users registered with this SGSN 26.

Another network element introduced in the GPRS/EDGE context is the Gateway GPRS Support Node (GGSN) 30, which acts as a gateway between the GPRS/EDGE backbone network 28 and a data network(s) 22. For example, the GGSN 30 may serve as a gateway between the GPRS/EDGE backbone network 28 and the Internet, or other data networks such as an Internet Protocol (IP) Multimedia Core associated with IP multimedia subsystems (IMS). The GGSN 30 allows mobile devices such as the PPC 14 to access the data network 22 or specified private IP networks. The connection between the GGSN 30 and the data network 22 is generally enabled through a standard protocol, such as the Internet Protocol (IP).

In the illustrated example involving an EDGE or other GSM-based network, data from the medical device 13 is transmitted "A," received by the base station 24, and forwarded "B" to the SGSN 26 and GGSN 30 for delivery "C" via the data network 22 to the targeted APM server 16A. The PPC 14 may first communicate via a proximity network(s) 32 such as a wireless local area network (WLAN). For example, where the PPC 14 is within a transmission range of a WLAN (e.g., IEEE 802.11b/g network), the PPC 14 can be configured to automatically or manually connect to the WLAN 32. Other proximity networks 32 can also be employed, such as Bluetooth, Zigbee and/or WIMAX. Such proximity networks can address connectivity issues with the mobile network 20, such as within a building where reception can be less than optimal.

In certain configurations, networks are described herein in terms of node networks, although arrangement of the networks as mesh networks is equally applicable to some aspects of the life critical network.

Another embodiment involves ad hoc peer-to-peer (P2P) networking, an example of which is depicted by the peer association 34. A peer-to-peer network does not involve traditional clients or servers, but rather the PPCs 14 serve as nodes functioning as both client and servers to other nodes. In this manner, a PPC 14 can use another patient's 12B, 12C PPC as a relay to the WLAN 32 or mobile network(s) 20. Additional aspects of P2P networking, aspects of which may be utilized in conjunction with the embodiments discussed herein are described in commonly owned U.S. patent application Ser. No. 11/248,879, filed Oct. 11, 2005, which is incorporated herein by reference.

The data originating at the PPC 14 may be stored and/or analyzed at the APM server 16A, which may be further coupled to one or more client stations 36 to perform input and output functions. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The mobile network 20 can further facilitate data or command transfer from the APM server 16A to the PPC 14. Data can be transferred in reverse sequence ("C," "B," "A"). Other channels may additionally or alternatively be used. For example, one embodiment involves sending commands from the APM server 16A to the PPC 14 using messaging services supported by the mobile network 20 and data network 22 infrastructures. These messaging services include, for example, Short Message Service (SMS), Enhanced Messaging Service (EMS), Multimedia Messaging Service (MMS), etc. These messaging technologies represent "store-and-forward" message services. For example, the APM server 16A may send "D" an SMS message that is received by an SMS Center (SMSC) 38 that provides the store-and-forward functionality, and is responsible for delivering "E" the message(s) to the base station 24 for ultimate delivery "F" to the address of the targeted PPC 14. The SMSC 38 stores the message until the PPC 14 is available, at which time it forwards the message, removes it from the SMSC 38, and notifies the APM server 16A that the message has been forwarded. Issuing commands from the APM server 16A to the PPC 14 using SMS is described more fully below.

MMS, also based on the store-and-forward service model, is similar to SMS in the manner that messages are communicated. However, unlike SMS, MMS is not limited to text messages. The destination address used in an MMS message may be the recipient's public number such as the Mobile Station Integrated Services Digital Network Number (MSISDN), or may be an e-mail address. Therefore, to minimize the chance of the PPC 14 receiving an SMS from an inadvertent source, a lengthy or otherwise unique e-mail address can be contrived and used as the destination address at the PPC 14. To minimize the risk of misdirected messages, messaging techniques such as those described herein may be combined with cryptographic authentication mechanisms to ensure that the PPC doesn't attempt to process and an erroneous message.

It may be desirable, for example, to use a store-and-forward data transfer protocol for less critical data and/or for performing incremental data transfers to/from a server. Use of a store-and-forward transfer protocol may be performed to reduce the volume of data transferred from the PPC to the remote server, yet provide sufficient connectivity between a patient's PPC and remote server.

For example, particular blocks of medical device data of interest may be selectably transferred from the medical device 13 to the PPC 14 in response to command signals generated by the remote server, PPC 14 or medical device 13. Generation of these command signals may result from programmed instructions residing in a memory of the PPC 14 or the medical device, execution of which may be triggered by the PPC 14, medical device or remote server. The programmed instructions may be modified by the physician, typically via the remote server or by an interface to the PPC 14 or medical device.

The physician may be interested in receiving arrhythmia (e.g., atrial or ventricular tachyarrhythmia) related data whenever such event occurs, for example. This selected sub-set of data is tagged for transfer to the PPC 14 in accordance with the physician's request. Depending on the severity of the event type, the physician may have requested that the event data be automatically transferred to the remote server via the PPC 14 immediately when the event occurs, or, for less serious events, be transferred the next time the PPC 14 connects with the remote server. The PPC 14, prior to establishing communications with the medical device, may be programmed to connect with the remote server and determine if and what specific information is to be acquired from the medical device. This inquiry by the PPC 14 may be performed immediately prior to connecting with the medical device or at some other time (e.g., at off-peak hours or during "cheap" connection times).

The PPC 14 may be programmed to require particular information from the medical device and/or remote server. Various implementations allow the PPC 14 to acquire particular information when needed. For example, the PPC 14 may initiate a real-time interrogation of the medical device, such as by commanding the medical device to wake-up (if applicable) and transmit (or acquire the requested information for transmission) to the PPC 14. The PPC 14 may be programmed to establish communications with the medical device in accordance with a pre-programmed schedule (which may be alterable by the remote server, medical device, or medical device programmer/interrogation device). Alternatively or in addition, connectivity between the medical device and the PPC 14 may be established in response to a remote command, such as a command generated in response to patient-actuated button on the PPC 14.

The remote server may be programmed to require particular information from the medical device and/or PPC 14. Various implementations allow the remote server to acquire particular information when needed. For example, the remote server may initiate a real-time interrogation of the medical device via the PPC 14, such as by commanding the PPC 14 to wake-up the medical device (if applicable) and transmit or acquire the required information for transmission to the remote server via the PPC 14. This scenario is generally reserved for important data, as commanded medical device wake-up and data transfer operations expend energy stores of the medical device. For less important data requests, the remote server may transmit a data acquisition command to the PPC 14 that is to be executed the next time the PPC 14 communicates with the medical device. In this scenario, an unscheduled or commanded wake-up and/or data transmission operation can be avoided. A tiered connection strategy may be employed to effect communications between the remote server, medical device, and PPC 14 that is dependent on a number of factors, including severity of a patient event, power consumption, status of communication link(s) (e.g., availability, quality of service, cost of service), physician/remote server needs, among others. The tiered connection strategy may be dictated or augmented by communication link profiles generated and stored in the PPC 14 in a manner previously discussed.

Upon detection of a physiologic or other event (e.g., arrhythmic episode), selected blocks of data about the event may be selected for transfer to the PPC 14. The selected data blocks typically include data acquired by the medical device during the event, and may be specified to include data temporally surrounding the event that is stored in the medical device's memory (e.g., data stored in a circular buffer representing data acquired n seconds before the event and m seconds after). Histogram, event counter, alerts, and related data may also be transferred in connection with the detected event.

With a constant or quasi-constant "live" connection with the remote server, it is possible to determine what event data for a given patient is presently stored on the server so that collection of duplicative data from the PPC 14 and/or medical device is reduced or eliminated. For example, a patient's implanted medical device (e.g., CRM device) may be interrogated at a clinic by use of a programmer. Prior to transferring data from the implanted medical device, a cross-check can be made between the remote server (via the programmer connected thereto) and the implanted medical device to determine whether data residing in the implanted medical device's memory had previously been transferred to the remote server using the PPC 14. If so, the duplicative data need not be re-transferred to the programmer, thereby conserving implanted medical device energy that would otherwise be expended to transmit the redundant data.

It should be recognized that the present invention may utilize mobile networks 20 other than GSM-based systems. For example, the Universal Mobile Telecommunications System (UMTS) is a 3G mobile technology that may in the future, and in some instances currently, replace GSM/GPRS network infrastructures. UMTS has a different air interface than GSM that can be connected to different backbone networks such as the Internet, ISDN, GSM or other UMTS networks. The PPC 14 can be configured to communicate via a UMTS network or any other existing or future network.

Figure 2A:
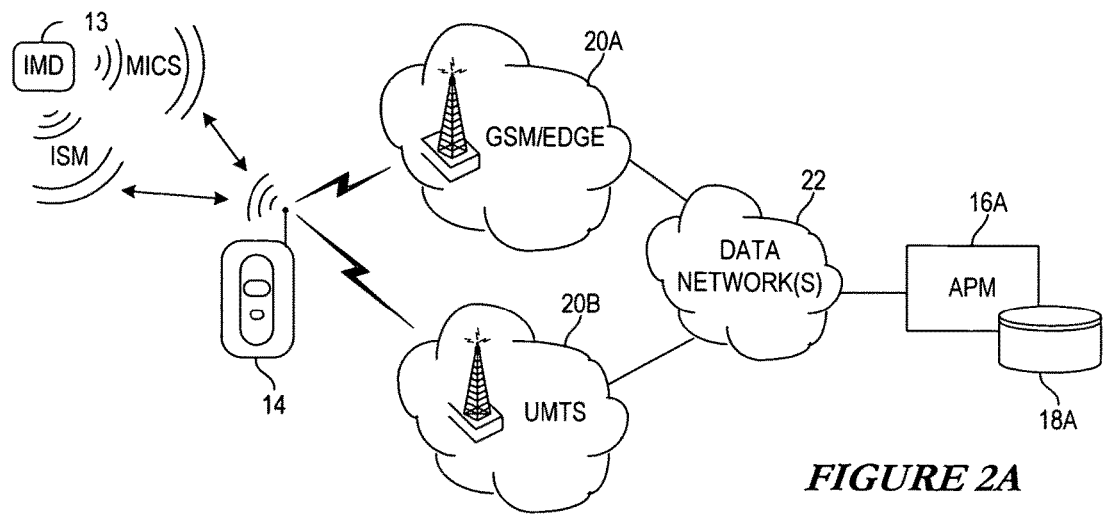
FIG. 2A illustrates a patient implantable medical device configured to operate in various frequency bands or channels for communicating with a portable patient communicator in the context of a life critical network in accordance with embodiments of the present invention.

In one embodiment the system is configured to operate on multiple mobile networks. For example, the air interface of UMTS is not compatible with GSM. As depicted in FIG. 2A, the PPC 14 can be configured as a dual-mode device capable of switching between, for example, an EDGE network 20A and a UMTS network 20B. If a patient equipped with a PPC 14 travels to an area without a first network coverage, the PPC 14 can switch to a second network. The PPC 14 can be configured to switch between a greater number of network infrastructures as well.

In the illustrated embodiment of FIG. 2A, the PPC 14 may ordinarily communicate data with the APM server 16A via a GSM/EDGE network 20A. If the patient moves to an area having only UMTS coverage, the PPC 14 can switch to the UMTS network 20B. In other embodiments network compatibility can be handled at the network level based on, for example, what is contained in the data communicated between the PPC 14 and the APM server 16A. Determination of which network is available can be accomplished in various manners, including determining what country or region the PPC 14 is in based upon the base station signal.

Multiple communication channels may also be provided between the medical device and the PPC. A patient implantable medical device is represented by PIMD 13 in FIG. 2A, which may communicate with the PPC 14 via various communication channels. The PIMD 13 or other medical device may communicate using the Medical Implant Communication Service (MICS), which is a reserved frequency band between 402-405 MHz. Other frequency bands may alternatively be used, such as the Industrial, Scientific and Medical (ISM) radio band, the Short Range Devices (SRD) radio band or others.

FIG. 2A illustrates that the PIMD 13 may be configured to operate in the ISM or MICS frequency bands, or in other channels. While the PIMD 13 may be originally configured for transmission via a single band (e.g., MICS or ISM), other embodiments enable the PIMD 13 to be configured to an appropriate transmission channel. Examples include providing a configurable transceiver module, or providing multiple transceiver modules respectively associated with each of the ISM or MICS (and/or other) frequency bands. The desired band may be designated through remote commands from the APM server 16A or elsewhere. The PIMD 13 may also be configured to automatically switch between communication channels in response to a triggering event. For example, communication between an PIMD 13 and the PPC 14 may switch from MICS to ISM if the MICS transceiver circuitry fails, thereby providing redundancy. The PPC 14 may be configurable in a like manner. For example it may automatically recognize the frequency of the signal and implement the appropriate ISM, MICS, or other circuitry.

The PIMDs 13 acquire the data that is ultimately communicated to the APM server 16A. This data varies depending on the type of medical device involved. In the case of PIMDs, examples of the acquired and communicated data include electrograms (EGM), events, episode counters, alerts, device settings, battery status, lead measurements, patient activity level, and the like. Data may be provided to comply with electronic medical record (EMR) standards. Collected data may be transferred all at once, or incrementally. Requests for data may also include data accumulated over time, such as certain data occurring on a daily, weekly, monthly, or other duration basis. The APM server 16A may selectively request, by way of the PPC 14, particular portions of the data stored in the PIMD or other medical device 13.

The PPC 14 is capable of communicating with the APM server 16A at any time a connection can be made, and thus provides an "always available" functionality. In addition to scheduled data transfers, this "always available" functionality supports event-driven data transfers that are provided in response to an event. Such events may be based on data analysis results, date, time of day, monitored conditions, etc. For example, if a particular patient-related health event occurs, relevant data can be immediately transmitted to the APM server 16A via the PPC 14. Communication of data between the various components may be customized for enhanced operation. Systems and methods involving customized data collection for a medical device which may be useful in combination with the embodiments described herein are provided in commonly owned U.S. Patent Publication No. 20070299317, which is incorporated herein by reference.

Other examples relate to medical device 13 diagnostic or operating conditions. One example is a low PIMD battery condition, which can be sent upon its recognition. Another example is an early memory overwrite warning where a notification can be transmitted when the PIMD memory is at a particular capacity level (e.g., 90%). Yet another example is emergency ambulatory communication of critical patient data. The notification can be used to trigger an interrogation of the PIMD 13 to retrieve the stored data.

Embodiments of the invention also support determining what source device or system interrogated the PIMD 13 or other medical device. For example, the PIMD 13 can be configured to determine whether a programmer or the PPC 14 interrogated the PIMD 13. The medical device 13 can also be configured to record status of data transmissions, including a status indicator(s) indicating whether certain data has already been recorded at the APM server 16A. Status may further include whether a core memory dump has been performed, or a safety core post-process.

In one embodiment the PPC 14 receives and/or transmits device-independent data. Consequently the PPC 14 can operate with different types or models of PIMDs 13 or other medical devices. This can be accomplished by configuring the PPC 14 to the particular type of medical device 13 to which the PPC 14 is, or will be, paired. When interrogating the medical device 13, the PPC 14 can send or forward generic commands such as "send episodes 1-3." This could be in the form of, for example, a style sheet. Alternatively, the PPC 14 can convert data from any type/model of medical device 13 to a common data structure. Data can also be compressed, either in the medical device 13 or the PPC 14, or both.

Life Critical Network

Figure 2B:
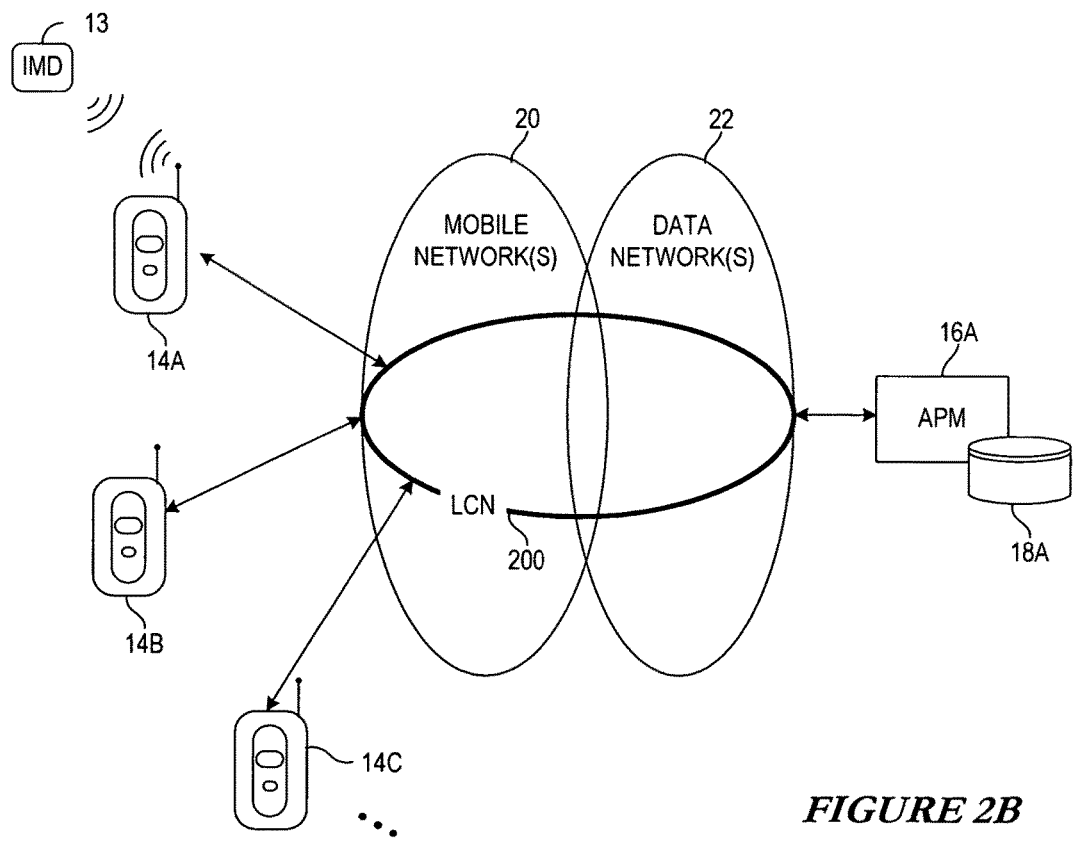
FIG. 2B illustrates a multiplicity of patient implantable medical devices that communicate via a life critical network comprising one or more mobile and data networks in accordance with embodiments of the present invention.

One aspect of the invention involves providing a robust network exhibiting heightened communication attributes such as guaranteed or near-guaranteed delivery, increased quality of service (QoS), tight security, etc. A network exhibiting such attributes according to embodiments of the present invention is referred to herein as a life critical network, as is discussed hereinabove. FIG. 2B illustrates a PIMD 13 and its corresponding PPC 14A. Any number of additional patients, and respective PPCs 14B, 14C may also be part of the LCN 200. Each of the PPCs 14A-14C is preferably configured to implement a dynamic communication link mapping methodology of the present invention.

As previously discussed, the LCN 200 essentially represents a private network supported by public network infrastructure. The LCN 200 is configured to operate on top of the existing mobile networks 20 and data networks 22. One feature of the LCN 200 is privacy, in that only devices intended for inclusion in the LCN are allowed. Access control can be accomplished through authentication, which refer to procedures established to verify that the device requesting access to the LCN 200 is the device that it purports to be. For example, a unique identifier(s) from the PIMD 13 may be used as a key to authenticate the device for use on the LCN 200. A more secure process involves specific keys and certificates programmed into the PIMD that allow the PIMD to authenticate messages from the server. The PIMD may use its ability to authenticate the server as a way to authenticate the PPC. A useful authentication method is the "challenge/response" approach described below.

Authentication can be further bolstered in various ways, including encrypting the identifier, or subjecting the identifier to a cryptographic hash function. A cryptographic hash function generally uses a character string or message of any length as input, and in response generates a fixed-length string output often referred to as a digital fingerprint. The unique identifier of the PIMD 13 could be used as the input. Alternatively, the PIMD 13 identifier can be concatenated with a unique identifier of the PPC 14, such as the Mobile Station Integrated Services Digital Network (MSISDN) number (i.e., the "phone number" or other address of the mobile PPC 14) for use with authentication processes. A cryptographic hash function may optionally be applied to the conjoined result and used for access control. These and/or other security measures are employed in various embodiments of the invention.

Authorization processes may also be used at the PPC 14 and/or APM server 16A. Authorization in this sense generally refers to functionality at the relevant device or system that protects the device from communicating unless it is granted authority to do so. Authentication and/or authorization may use unique identifiers or certificates and cryptographic keys to determine whether device functionality (authorization) or network access (authentication) is allowed. For example, in one embodiment, the unique identifier(s) from the PIMD 13 may be used as a key to authorize communication functionality on the PPC 14.

Components of the life critical network may incorporate various methodologies for providing secure and reliable communication, including features described in one or more of the following references: U.S. Patent Publication Nos. 20070100396, 20070118188, 20070083246, and U.S. Pat. Nos. 7,218,969; 7,203,545; 7,801,620; 7,805,199; 7,218, 969; 7,751,901; 8,041,032 and 8,027,727 all of which are incorporated herein by reference.

The LCN 200 can provide virtual connections routed through public networks 20, 22 to separate the traffic of the intended and unintended communication nodes over the underlying networks. Firewalls may also be used, which provides a barrier between the LCN 200 and the public networks 20, 22. These firewalls can restrict the number of open ports, specify what type of packets are passed through, and specify which protocols can pass. Information communicated via these restricted channels can further be encrypted, which involves encoding the data into a form that only the other intended nodes of the LCN 200 can decode. Because the PPC is exposed on the cellular network, a firewall is used to prevent unauthorized access attempts.

Embodiments of the LCN 200 aim to operate as a guaranteed delivery system or a near- or quasi-guaranteed delivery system. For some data and commands between the PIMD 13 and the APM server 16A, timely delivery may be crucial. To approach guaranteed delivery, the LCN 200 implements mechanisms to ensure high quality of service (QoS) transmission. QoS involves various aspects of the connection, such as the time to provide service, echo, loss, reliability, etc.

In addition to guaranteed delivery of data, there may be a need for guaranteed throughput for some data, such as real-time EGM or other monitored cardiac signals. For example, data can be streamed from the PIMD 13 to the APM server 16A via the PPC 14. Streaming data over the LCN 200 can be accomplished in any known manner. Protocols such as the real-time streaming protocol (RTSP), real-time transport control protocol (RTCP) and real-time transport protocol (RTP) enable time-sensitive data to be streamed over data networks. RTP and RTCP are built on the user datagram protocol (UDP), where the data is sent in a connectionless manner in a series of data packets.

Connection-oriented protocols such as the Transmission Control Protocol (TCP) may also be used, as it utilizes acknowledgements to guarantee delivery. While TCP may experience some loss and retransmission delays, some data loss may be tolerable depending on the data being streamed. For example, non-critical, substantially real-time EGM signals may sufficiently provide a clinician with the needed information, notwithstanding some relatively insignificant data loss or latency. Heightened QoS is also implemented on the mobile telecommunication network portion of the LCN 200.

The type of connection and manner of data transmission as between a remote server of the LCN 200, such as server 18A of the APM server 16A, and the PPC 14 may vary depending on a number of factors that may be considered when implementing a dynamic communication link mapping methodology of the present invention. Such factors include the criticality of the data (e.g., type and criticality of physiological or other patient related data acquired from the patient's medical device, patient sensor or information manually input to the PPC 14 by the patient; nature of a software/firmware update for the medical device or PPC 14; scheduled standard interrogation data vs. patient event/episodic or device diagnostic data; distress of the patient, such as an emergency vs. non-emergency situation; whether data is to be pushed or pulled; geographical location of the patient/PPC 14; available communications infrastructure, whether domestic or international, etc.).

In one approach, the PIMD 13 determines the criticality of the data based on the patient condition or event detected by the PIMD 13. A look-up table of patient condition/event severity versus criticality level may be established for a particular PIMD 13. For example, a look-up table stored in the memory of an ICD may categorize ventricular fibrillation as the most critical level (L1), followed by ventricular tachycardia-1 (L2), ventricular tachycardia-2 (L3), premature ventricular contractions (L4), pacemaker-mediated tachycardia (L5), atrial fibrillation (L6), atrial tachycardia (L7), supra-ventricular tachycardia (L8), premature atrial contractions (L9), etc. Each patient condition/event can have a corresponding criticality level, it being understood that two or more conditions/events can have the same criticality level. In response to one of these or other triggering events, the PIMD 13 preferably transmits criticality level data, along with other data, to the PPC 14.

The connection attributes by which the PPC 14 connects with, and communicates over, the LCN 200 may be based, at least in part, on the criticality level data received from the PIMD 13. For example, the PPC 14 may be programmed to establish a real-time, high QoS connection for high criticality levels, while lower criticality levels may only require a standard QoS connection. The PPC 14 may progress sequentially through a prioritized list of connection types/attributes associated with a given criticality level, until the connection is established. For high criticality levels, for example, the prioritized list may be organized so that the PPC 14 progresses sequentially from most desirable to least desirable connection type/attributes. For low criticality levels, the prioritized list may be organized so that the PPC 14 progresses sequentially from least expensive (e.g., night or off-peak hours) to most expensive connection type/attributes.

It is noted that, in the case of a high criticality level scenario, the PPC 14 may not be able to connect with the LCN 200 (e.g., PPC 14 is in an underground area of the hospital). In such a case, the PPC 14 may include a visual indicator that illuminates, flashes or provides a message prompting the patient (or caregiver) to move to another location so that the PPC 14 can establish a connection. The PPC 14 may also or alternatively produce an aural and/or tactile (e.g., vibratory) output to prompt the patient (or caregiver) to move to another location so that the PPC 14 can establish a connection.

According to another approach, the PPC 14 determines the criticality of the data based on the patient condition or event detected by the PIMD 13. A look-up table of patient condition/event severity versus criticality level may be established for a particular PIMD 13 and stored in a memory of the PPC 14. As in the case of the immediately preceding example, the connection attributes by which the PPC 14 connects with, and communicates over, the LCN 200 may be based, at least in part, on the criticality level data determined by the PPC 14. In addition to PIMD data, it may be desirable for one or both of the PIMD 13 and PPC 14 to use sensor data (implanted or external) to determine or modify the patient's criticality level.

In one embodiment, the particular QoS or other network attributes can change relative to the patient status. For example, data originating from scheduled status transmissions can be communicated using a standard QoS. The QoS of transmitted data can rise as the relative criticality of the data or underlying condition rises. Critical data such as that triggered by a serious cardiac anomaly can be communicated to the APM server 16A, a hospital, an ambulance or other relevant destination using the highest QoS. It may be necessary or desirable to prioritize APM server response/resources based on patient status and/or condition. Criticality of patient condition may be used as a parameter by the APM server to determine which patients to triage first.

The criticality of a patient condition may change after an initial QoS has been determined. For example, an initial QoS or other network attribute may be initially established based on detection of atrial fibrillation. The QoS or other network attribute may adjust in real-time during and/or after the atrial fibrillation episode depending on a change in the patient's status. The QoS or other network attribute may be increased/adjusted if the atrial fibrillation accelerates or if it induces ventricular arrhythmia, for example. Conversely, the QoS or other network attribute may be reduced/adjusted if the atrial fibrillation lessens in severity or terminates either spontaneously or via atrial therapy delivered by an implanted CRM device, for example. This sliding scale of patient status-to-QoS provides the appropriate delivery guarantees based on the particular circumstances.

Various QoS attributes can be controlled in order to provide an appropriate connection for transmitting medical data over the LCN 200. Various QoS attributes may be modified to change connection attributes based on the criticality of the medical data to be transported over the LCN 200. Such QoS attributes may include traffic influencing parameters, such as latency, jitter, packet loss, bandwidth, and response time; management of finite resources, such as rate control, queuing and scheduling, congestion management, admission control, routing control, traffic protection; and service level agreement requirements for flows (e.g., flow-based or aggregated flows).

QoS service methodologies that may be made available for medical data transport include best effort (no QoS), integrated services (hard QoS, IntServ Architecture, see RFC 1633, RFC 2205, RFC 3175), and differentiated services (soft QoS, DiffServ Architecture, see RFC 2475, RFC 3270) methodologies. Another network technology that allows for QoS priority selection is referred to as MPLS (Multiprotocol Label Switching, see RFC 3468, RFC 3209). DiffServ, for example, can be used to provide low-latency, guaranteed service to critical network traffic, such as transport of high criticality PIMD data, while providing simple best-effort traffic guarantees to non-critical network traffic, such as low criticality PIMD data, PIMD-APM server traffic, or routine file transfers.

One approach to implementing selection and/or adjustment of network QoS attributes based on medical data criticality is to establish a mapping of QoS attributes needed to support the LCN network (e.g., a mapping of desired or required QoS attributes based on PIMD data criticality). This LCN QoS schema can be developed by the medical device manufacturer in cooperation with physicians and health care entities, for example. A schema of the public network QoS (e.g., the cellular network(s) and any other data network(s) that are part of the LCN 200) may be developed by the medical device manufacturer in cooperation with the cellular and other network operators, for example. A QoS mapping of LCN QoS-to-public network QoS (e.g., for data transfers from the PPC 14 to the APM server 16) and a mapping of public network QoS-to-LCN QoS (for data transfers from the APM server 16 to the PPC 14) may thus be developed using the LCN and public network QoS schemas.

In accordance with another approach, the LCN 200 may provide enhanced medical data transport using a Wireless Priority Service (WPS). WPS has been developed to provide priority for emergency calls made from cellular telephones. WPS is an easy-to-use, add-on feature subscribed on a per-cell phone basis, with no special phone hardware required. WPS is implemented as software enhancements to existing cellular networks, and is being deployed by cellular service providers in their coverage areas throughout the United States.

WPS provides priority for emergency calls through a combination of special cellular network features. WPS addresses congestion in the local radio access channel (or cell), which is often the reason that cellular calls cannot be made during heavy calling periods or when damage to network infrastructure occurs. WPS automatically provides priority access to local radio channels, placing WPS calls in queue for the next available channel if a channel is not immediately available. Originating Radio Channel Priority requires WPS feature activation on the calling cellular phone. WPS calls do not preempt calls in progress.

When a radio access channel becomes available and the call proceeds, WPS calls are assigned a unique call marking by the cellular network switching equipment. This marking triggers industry standard High Probability of Completion (HPC) features residing in most U.S. telecommunications networks as calls are routed from the originating cell to the called cellular or landline phone. These HPC features significantly increase the probability of call completion should the call encounter network congestion or blockage beyond the originating cell.

Access rights of a PPC 14 to connect to the Wireless Priority Service may be established by medical device manufactures and local and national governmental agencies. The connection attributes or rights by which the PPC 14 connects with, and communicates over, a WPS connection of the LCN 200 is preferably based on criticality level data received from the PIMD 13. For example, the PPC 14 may be authorized to establish a WPS connection for high criticality levels, while lower criticality levels may not qualify for a WPS connection.

As described above, commands may be sent from the APM server 16A to the PPC 14 using messaging services supported by the mobile network 20 infrastructure. One embodiment of the invention involves using Short Message Service (SMS) or "text messages" to direct commands to the PPC 14 for ultimate delivery to the PIMD 13. Verification techniques may be employed to ensure that an SMS message from an unauthorized source is not inadvertently addressed to the PPC 14 and perceived as a command. In one embodiment, a subset of the data in the SMS message may be used by the PPC 14 to verify that the SMS message originated from an authorized source (e.g., APM server 16A). One example involves the PPC 14 comparing the source address (e.g., MSISDN number) of the SMS message with a stored list of approved source addresses. In another exemplary embodiment a code may be inserted into the SMS message itself. For example, a standard SMS message supports 160 characters, and the first predetermined number of characters may represent a code used by the PPC 14 to verify that the sender is genuine. The code may be the concatenated PIMD/PC identifiers signed with the APM server's private key. The APM server's private key can be verified by both the PPC and the PIMD as they have the public key for the server in their set of certificates.

Figure 3:
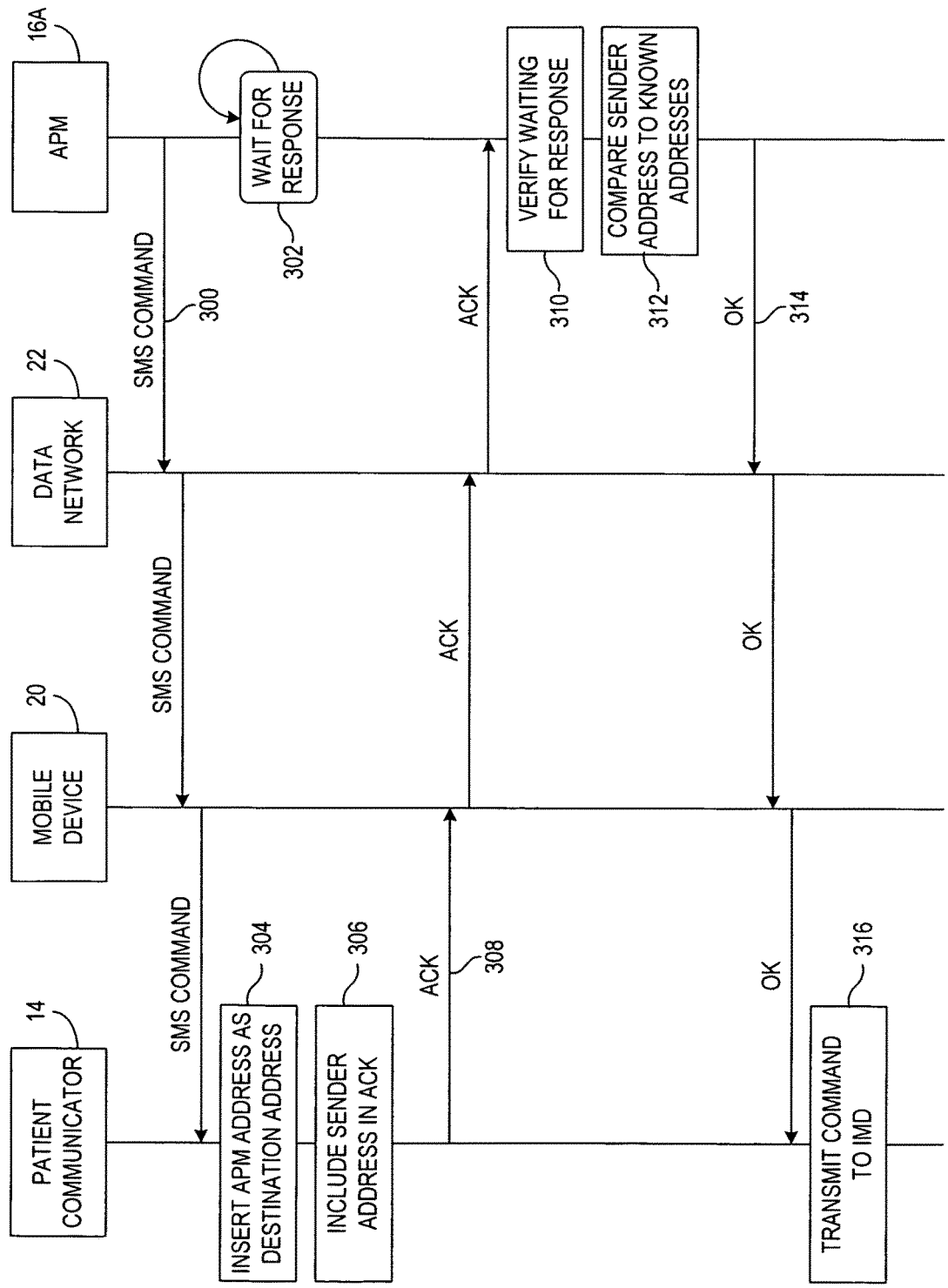
FIG. 3 is a message flow diagram illustrating one manner of using acknowledgment messages to verify the source of an SMS message communicated between a remote server and a portable patient communicator via a life critical network in accordance with embodiments of the present invention.

Message verification techniques utilizing handshaking may also be used. FIG. 3 is a message flow diagram illustrating one manner of using acknowledgment messages to verify the source of the SMS (or other) message. Such a handshaking embodiment enables the PPC 14 to verify that the command originated at an APM server 16A or other authorized source before forwarding the command to the PIMD 13. This may be beneficial, for example, where the PPC 14 is unaware of the APM server 16A source address. The PPC 14 may be generally unaware of APM addresses, or new APMs having new source addresses may be added to the system unbeknownst to the PPC 14.

Operationally, the APM server 16A may direct a command to the PPC 14 via an SMS-based command 300. If the APM server 16A was in fact the source of the SMS message, it enters a wait state 302 or otherwise notes that it has initiated the message. The command is forwarded through the data and mobile networks 22, 20, and arrives at the PPC 14. Rather than "reply" to the source address of the incoming SMS message, the PPC 14 inserts 304 a known APM address as the destination address. Thus, even if the SMS message originated at an unauthorized source, the resulting acknowledge message (ACK) 308 is directed to the APM server 16A. Additionally, the sender's address (i.e., the source address identified in the received SMS message) can be included 306 in the responsive ACK message, for reasons discussed more fully below.

When the ACK 308 arrives at the APM server 16A, it verifies 310 that it was in a wait state, waiting to receive an ACK message from the PPC 14. If it was not, it can be assumed that the SMS message received at the PPC 14 was not issued by the APM server 16A, and the APM server 16A can notify the PPC 14 as such. Further, the sender address provided by the PPC 14 in the ACK message can be compared 312 to a set of known APM addresses, if multiple APM and corresponding APM addresses exist. If the received sender address does not correspond to any known APM addresses, it again can be assumed that the original SMS message received at the PPC 14 was not initiated by the APM system. If the received sender address matches a known APM address, the APM sends an OK 314 or other confirmatory message to notify the PPC 14 that the original SMS message was indeed issued by the APM system. Upon receipt of the OK 314 message, the PPC 14 can transmit 316 the command embodied within the SMS message to the PIMD 13 or other medical device paired with the PPC 14. Additional or alternative processes for message verification that may be used are described in commonly owned U.S. Patent Publication No. 20070185547, which is incorporated by reference herein.

When using the SMS medium, the security keys and identifiers included in the text message need to be smaller than the character limit for SMS. In one approach, a key that the APM server recognizes may be embedded in the text message. A simple encryption approach may be used, which involves sending medical data without patient-identifying information, and including the medical device serial number or the SIM (Subscriber Identity Module) serial number.

Streaming data from the PIMD 13 or other medical device over the LCN 200 and to the APM server 16A via the PPC 14 may be enabled and disabled in a number of ways and in response to varying conditions, triggers or events. The manner and paths by which PIMD data is streamed over the LCN 200 may be based on events or patient conditions such as criticality of the data, distress of the patient, and whether or not an emergency call has been attempted via a 911 service, among others.

A PPC 14 may be programmed so that its behavior relative to the LCN 200 and/or the PIMD 13 is dynamically adjusted based on predetermined conditions. These conditions may be part of the PPC's communication link profile, as discussed hereinabove. For example, if the PPC 14 detects that it is out of range of the PIMD 13, the "status" of the PPC 14 on the LCN 200 may be changed (e.g., reduced). The status of the PPC 14 refers to the level of capabilities granted a particular PPC 14 when operating over the LCN 200. A PPC 14 that is out of range of its corresponding PIMD 13 may have a reduced ability to communicate with the APM server 16, such as by being denied access to certain functions (e.g., over-the-air PPC firmware upgrades, PIMD interrogation or programming commands) and data that are appropriate only when the PPC 14 is in range of its paired PIMD 13.

By way of further example, use of cellular phones and devices is often restricted in most areas of hospitals and health care clinics, but permitted in lobby areas. During a hospital or clinic visit, it may be desirable to establish communication between the PPC 14 and the LCN 200/APM server 16, particularly during extended visits. Assuming that the patient is restricted to his or her room, a caregiver may take the PPC 14 to the lobby or other permitted area and establish a connection with the LCN 200/APM server 16. Granting authorization to the caregiver may involve some form of authentication, such as thumbprint, voice, or PIN code authentication, for example. The PPC 14 may be configured with appropriate hardware and software to perform this "third party" authentication, which will vary depending on the manner of authentication (e.g., a thumbprint reader, voice-recognition circuitry).

The present "status" of a PPC 14 may not be apparent to the patient until a connection with the APM serve 16 is attempted, either automatically or by actuation of a manual sync button on the PPC 14 that initiates an upload/push data operation, for example. If the patient attempts to use the wrong PPC 14, an indication of the PPC's reduced status is preferably indicated in some visual, aural or tactile manner to the patient. Although basic data may be transferred out of the PPC having a reduced status, full uploading/functionality may only be granted to a properly paired PPC, although high priority/criticality data/events would likely be excepted.

Tiered functionality may be programmed into the PPC based on correct or incorrect pairing. There may be scenarios where incorrect pairing is detected, but the location of the PPC indicates that a PPC's status need only be minimally reduced (or not at all). Scenarios where incorrect pairing occurs, but where there is a high level of confidence that the PPC 14 is in the right location for the patient, include multiple PPC scenarios, the PPC in the office, home, clinic, physician's office or hospital, the PPC in a nursing home, and the PPC in a pharmacy (via the pharmacy's Wi-Fi that can be identified as such).

The effectiveness of the LCN 200 depends in large part on the reliability of the cellular network or networks that facilitate connectivity between PPCs 14 and the APM servers 16. Various techniques can be implemented to improve data transmission efficiency and reliability through the LCN 200. A forward error correction approach, for example, may be implemented by which data is re-sent multiple times from the PPC 14 (e.g., data redundancy).

An approach to determining appropriate connection attributes for a PPC 14 may involve determining latency of transmission between the PPC 14 and the APM server 16. One approach to determining this latency is to determine round trip time (RTT), such as by use of a ping service, which may be initiated by the PPC 14. In response to receiving a ping packet transmitted by the PPC 14, the APM server 15 sends back a response packet (i.e. performs a no-op). A ping operation does not involve performing packet processing, so the RTT measured by the PPC 14 is a relatively accurate measure of round trip latency. The PPC 14 may be programmed to perform a ping operation and consider RTT when determining appropriate connection attributes for connecting to the LCN 200.

Depending on the criticality of the data, the PPC 14 may be programmed to negotiate a higher output power from the cell tower(s) or an increase in the PPC's network interface transmission power on a temporary basis. In general, a conventional cellular phone is not permitted to adjust its network interface power output with respect to the particular cell towers over which it is presently communicating. Rather, network interface output power of cell phones communicating over particular cell towers is moderated by those cell towers. A cellular network operator may cooperate with the medical device manufacturer of the PPCs 14 to offer special services for patient subscribers that use the operator's cellular network to support the LCN 200.

These special services may include the PPC 14 negotiating a higher output power from cell tower(s) for transmitting critical data. Alternatively, or in addition, the cell tower(s) can raise its base power. These special services may include adjusting the QoS for transmitting critical data and/or change the carrier frequency to a frequency that minimizes interference with other connections. Unique information (codes or profile packets/bits) may be transmitted from the PPC 14 that indicates a request for special services is being made which is recognizable by the cellular network operator. Based on the data's criticality level, one or more connection attributes may be adjusted by the cellular network operator in response to the PPC's request.

Embodiments of the invention are directed to tiered approaches for communicating data over a life critical network. A tiered or prioritized approach to communicating medical data over a network is particularly beneficial in cases where non-ideal infrastructural conditions exist or arise, such as dead spots or undesirable tower interaction in a wireless communication system, and where patient condition can vary dynamically between normal and life-threatening. A tiered approach facilitates exploitation of different communication protocols and mediums for different clinical data, events, and/or priority.

According to some embodiments, the PPC 14 implements control logic to determine the proper communication protocol and medium for exchanging data with a remote server based on the purpose and priority/urgency of the data exchange and/or infrastructural status. The PPC 14 may, for example, have different physical channels of communications available to it, such as a telephone line, cellular, Wi-Fi, etc. Not all of these physical channels are always available, and they have different costs, performance characteristics, and levels of service. Cellular technology, for example, allows for a number of different mechanisms for data exchange, each with different levels of service, throughput, and purposes (e.g., raw data, SMS, email, and others).

The PPC 14 and remote APM server 16A have many different reasons to exchange data. Data transmission from/to the PPC 14 and APM server 16A occurs at different frequencies, some are physician or patient initiated, and some are medical device manufacturer initiated. These data have different priorities, including urgent, nominal, or low priority, or even optional. The PPC 14, according to some embodiments, may be configured to determine some or more of the degree of urgency, purpose of the data exchange, the cellular network's current capabilities, and the transport mechanisms available.

In accordance with an illustrative example of a tiered communications approach as between a PPC 14 and a remote APM server 16A, it is assumed that the highest degree of priority or urgency is associated with an emergency or time critical situation, such as when therapy delivery is ineffective or all therapies are exhausted. In such cases, the PPC 14 is preferably programmed to utilize all communications protocols and mediums available to it. Some of these channels may be reliable while others may be unreliable. Parallel messages over multiple channels (data channels, SMS, two cell towers, Wi-Fi to local network) are preferably transmitted by the PPC 14 in an attempt to reach the APM server 16A. The PPC 14 preferably sends the same urgent message on all the mediums.

According to one approach, the PPC 14 sets a unique identifier for the message to be delivered on all mediums. The same identifier is used on all of the messages triggered by the same event. The APM server 16A may receive one or more of the urgent messages through any of the channels. The APM server 16A utilizes the unique identifier and identifies that the messages are the same. The APM server 16A only acts on one of the messages-acting on more than one is redundant. A unique stamp may be used to verify this is the same message, albeit received from disparate mediums.

In response to receiving the message from the PPC 14, the APM server 16A preferably sends an acknowledgement back to the PPC 14. The acknowledgement includes the unique identifier. When the PPC 14 receives the acknowledgement, it discontinues transmitting the urgent message. If the PPC 14 does not receive an acknowledgement, it continues to retry/transmit the urgent message at some regular interval.

Continuing with this illustrative example, it is assumed that an alert based on patient data represents the second highest priority or urgency level. A typical "red" alert indicates that there is a problem with the medical device or patient's health condition that needs to be communicated to the APM server 16A (e.g., "Not in Monitor+Therapy Mode" alert condition). In response to an alert condition, the PPC 14 first attempts to use the configured cellular/mobile data network interface. Using a cellular/mobile medium, the clinician receives the alert sooner than when using a once-per-day scheduled check of the PPC 14 initiated by the APM server 16A. If the cellular/mobile medium or other data interface is not available, the PPC 14 attempts a more simpler form of data exchange, such as a store-and-forward exchange (e.g., SMS).

The third highest priority or urgency level according to this illustrative embodiment may be for problems with the PPC 14 where the patient is in an unmonitored state (i.e., unmonitored by the APM server 16A). A problem with the PPC 14 may be detected by the APM server 16A, such as by detecting non-receipt of PPC data for a predetermined period or failure to receive such data in accordance with a predetermined schedule. The APM server 16A may also detect an unmonitored patient state by pinging the patient's PPC 14 and failing to receive a response from the patient's PPC 14 within a predetermined period of time. The APM server 16A, in response to detecting loss of connectivity with the patient's PPC 14, may attempt to establish communication with the PPC 14 using all mediums and protocols available to it, preferably using a tiered approach. For example, the APM sever 16A may attempt to use a data network followed by use of SMS.

The PPC 14 may detect loss of APM server connectivity using strategies similar to those discussed above but initiated by the PPC 14, such as dictated by a prioritization scheme in accordance with a dynamic communication link mapping methodology of the present invention. If, after implementing a tiered strategy for attempting to connect with the APM server 16A, the PPC 14 determines that such attempts have been unsuccessful, the control logic of the PPC 14 may execute a procedure to draw patient awareness to the present problematic state of the PPC 14. The PPC 14 can, for example, flash an alert light or message on a display or broadcast an audible alert. Other approaches may be used, such as activating a vibrating element of the PPC 14 or other tactile transducer. These and other methods of attracting the patient's attention may be implemented, such as in a tiered approach based on factors such as power consumption, likelihood of success, or pre-determined preferences established by or for the patient. The patient, upon detecting an alert initiated by the PPC 14, may contact the physician or PPC manufacturer or service for assistance.

The fourth highest priority or urgency level according to this illustrative embodiment is for data exchanges to and from a physician or clinician. Data transfers to the physician is effected in a manner discussed previously with regard to implementing a tiered approach for transferring data from the PPC 14 to the APM server 16A over the LCN 200. For data transfers from the physician to the PPC 14, a store-and-forward medium or protocol is preferably used, since the PPC 14 may not be presently connected to the APM server 16A. According to one approach, a physician (or r technician) preferably defines an interrogation schedule, and the APM server 16A pushes the interrogation schedule to the PPC 14. This approach may be supplemented by scheduled (or commanded) PPC pulls from the APM server when the PPC 14 connects with the APM server 16A.

Clinicians may push data to the PPC 14 from the APM server 16A for a variety of reasons other than, or in addition to, performing PIMD or PPC interrogations. For example, physician directed data may be pushed to the PPC 14 to prompt the patient to take some action, such as to take drugs (e.g., maintain prescribed medication regimen, titrate diuretics, activate or adjust drug delivery device), take some type of measurement (e.g., weight, oxygen saturation, blood pressure, heart rate), or interact with a sensor (e.g., blood pressure cuff, weight scale, glucose sensor), among other actions. The clinician may analyze certain data and effect some form of communication to the PPC 14 via the APM server 16A.

The fifth highest priority or urgency level according to this illustrative embodiment is for notifying the patient that a data transmission failed after repeated attempts. This message class includes messages for prompting the patient to contact the medical device company if the PPC 14 is unable to communicate properly. A sixth highest priority or urgency level is for performing routine interrogation of the PIMD 13.

The seventh highest priority or urgency level according to this illustrative embodiment is for evaluating status of the PPC 14. This message class consists of very low priority information that can be lost or not collected. It consists of diagnostic information not critical to the patient, physician, or the system operation. Accordingly, a low cost transport mechanism (e.g., SMS) is preferably selected. The transmission of low priority content may be delayed for lower cost periods of the day/night.

The manner in which a multiplicity of PPCs 14 connect with, and communicate over, the LCN 200 may be controlled to reduce overall network usage. For example, the quantity and type of content of the data transmitted over the LCN 200 (uni- or bi-directional) may be adjusted (increased or decreased) by the APM system operator as needed or desired. Data content and transmission attributes may be modified on-the-fly for one or a multiplicity of PPCs 14, which may affect the PPC(s) 14 future behavior by causing it/them to not send as much data or to send more data, depending the need. The APM system operator may, for example, control all PPCs 14 in group-wise fashion, such as by reducing or disabling data content transmission from the PPCs 14 or by commanding all PPCs 14 to transmit full data content with diagnostics, including communicator and SIM identification data, for example.

The manner in which data is to be exchanged between the PPC 14 and APM server 16A may be impacted at least in part by the cellular infrastructure. For example, a message or settings may be sent from the APM server 16A to all or appropriate cell towers that will pass the message or settings on to one or more of the PPCs 14. The message or settings may be delivered to the PPC(s) 14 in a variety of ways, such as part of a normal tower-communicator cellular exchange, a queued transmission at off-peak hours, or as part of a PPC 14 being powered-up and setting up the cellular connection.

LCN Connection Strategies

The efficacy of a life critical network depends in large part on the capability of the LCN to facilitate transport of critical medical data (e.g., CRM device data) over a public cellular network infrastructure in a secured and time-efficient manner. A variety of methodologies may be employed to maintain and enhance LCN efficacy, such as those discussed hereinabove with regard to a dynamic communication link mapping methodology of the present invention. For example, the integrity of the communication link between the PIMD 13 and PPC 14 may be enhanced by performing block transfers of PIMD (e.g., IPG) data snapshots into a buffer for transfer to the PPC 14. This approach may advantageously avoid dropouts between the PIMD 13 and PPC 14. As was discussed previously, PIMD data transferred to the PPC 14 may be transmitted over the LCN 200 in a number of ways, including a session based connection or an ACK-based connection. Suitable transport approaches include automatic retry query (ARQ), TCP, and UDP streaming, among others.

Another approach involves transmitting an urgent message or important/critical data to multiple cell towers, such as two towers. The message/data can first be transmitted to the cell tower that provides the best signal quality followed by transmissions of the same message/data to the tower(s) with lower signal quality. Variations of this approach are discussed hereinabove.

In cases where a preferred LCN connection is not available or becomes unusable, alternative connections may be sought in accordance with a predetermined priority scheme. For example, should a preferred connection such as a high QoS cellular connection become unavailable, a PPC 14 may attempt to connect to the LCN 200 using a data channel (e.g., Ethernet connection), MMS, SMS, Wi-Fi, or low-speed modem over a voice channel (to operate as a modem to transmit data), for example. If a patient has no cell coverage, intermittent coverage, or periodic (e.g., day/night) coverage, a predetermined priority scheme may include switching to a Wi-Fi network as backup. The Wi-Fi is preferably preconfigured to provide efficient connectivity between the PPC 14 and the LCN 200. Another fallback is to attempt a connection using any network that can be found by the PPC 14.

When out in public, several opportunities for connecting to the APM server 16A may be exploited. In one approach, a public kiosk or Wi-Fi access point (e.g., municipal, within a store or coffee house, at a pharmacy) may be used. A tiered connection and data transport strategy may be implemented in accordance with the type of connection made.

For example, a greater range of PPC functionality may be granted if the PPC 14 connects with the APM server 16A via a pharmacy or hospital's wireless access point, relative to a generic public access point. Several network service discovery mechanisms may be used by the PPC 14 to facilitate discovery of available network services, including ultra low-power mechanisms (e.g., via Bluetooth). Another approach involves hopping onto another person's cell phone who is in proximity with the patient's PPC 14. Yet another approach involves an ISM to ISM scheme, which can be a relatively long range mechanism (e.g., 200 meters) that provides complete control of a radio. This approach would allow the PPC 14 to connect (i.e., bootstrap) to another PPC 14 or cell phone via ISM radio, and then using the cell phone for establishing a network connection.

According to another approach that involves a docking station or hub for the PPC 14, a message or indicator may be communicated to the patient by the hub or PPC 14 to dock the PPC 14 to the hub. Assuming the hub has an alternative medium to connect to the LCN 200, such as POTS connection, this alternative medium can be used to connect the PPC 14 to the LCN 200.

Another approach involves the PPC 14 indicating to the patient to move to another area where coverage is available. The PPC 14 may indicate to the patient that a message needs to be transmitted and the patient should try to go to a known good cellular coverage area or dock their device.

In cases where PPC data is collected at a scheduled time, such as during the night), but there is no coverage when patient is at rest, a number of actions may be performed. A store-and-forward procedure may be implemented when the connection becomes available. Another action may involve a mechanism to notify the patient, especially is the case of an emergency (e.g., red alert) condition. If the data is not received by the APM server 16A or the PPC 14 does not get a signal for a predetermined period of time, the patient is preferably notified (e.g., a phone call to the patient's home, an email or SMS message to the patient's cell phone).

Some classes of devices, as controlled by their SIM, may have higher priority for using the cellular infrastructure, such as police, fire, and emergency medical personnel (e.g., higher priority via a Wireless Priority Service connection). During normal operation with no emergency data, the PPC 14 preferably utilizes normal SIM settings and receives the commonly available cellular service. If the PPC 14 has emergency data to be delivered, the PPC 14 preferably registers with the emergency-class SIM to utilize the special-availability class of service. It is important to change the emergency priority designation based upon status to avoid always using emergency channel.

If the cellular network is full or otherwise inaccessible, the PPC 14 may be programmed to re-attempt a connection at appropriate intervals, which would preferably involve attempts to connect via alternative mediums. Should the PPC 14 ultimately fail to connect to the LCN 200, a message or indictor is preferably presented on the user interface of the PPC 14 (or broadcast via an audible message or tactile output) prompting the patient to contact his or her physician or medical device manufacturer.

International travel by a patient can present a number of challenges when attempting to connect to the LCN 200 via the PPC 14. A dynamic communication link mapping methodology of the present invention may be employed in the context of international movement of the PPC 14. For example, when traveling in an airplane or on a cruise ship, the PPC 14 is preferably programmed with a profile that instructs the PPC 14 to connect to the LCN 200 via an airborne or shipboard communications network. For example, the PPC 14 is preferably configured to access an airliner's cellular access point via a wireless protocol, such as onboard Wi-Fi device (e.g., AirCell 802.11 a/b/g wireless access point or an 802.11 n wireless access point). A typical airborne cellular network deployment includes three towers mounted on the exterior of the plane, which beam to ground stations in the United States. A similar approach is employed in Europe and elsewhere. Some airlines provide Ethernet and USB ports in each seat which can be used to provide LCN connectivity. When cruising, the patient may connect with the LCN 200 via a global maritime cellular operator that is accessible throughout the cruise ship. The shipborne radio networks, typically GSM or CDMA, are generally linked to public networks via satellite.

The PPC 14 may provide the option to operate in "flight mode," in which the transceiver used to connect to a wireless network is turned off. The wireless transceiver that communicates with the PIMD may remain on or may be switched to a short range power setting (or may be turned off as well). The PIMD transceiver of the PPC 14 may incorporate a wake-up detection circuit that "listens" for an emergency wake-up signal from the PIMD. This emergency signal may be a low-power RF signal, an acoustic signal, or other signal that does not (or only minimally) interferes with onboard communications systems.

The PPC 14 may be set to "flight mode" by actuation of an appropriate button on the PPC 14 (or by voice command activation). A flashing light or other indicator is preferably generated to indicate to the patient that the PPC 14 is in "flight mode." After the flight, the flashing light or indicator prompts the patient to switch off the "flight mode." Various automatic techniques may be employed to ensure that the PPC 14 does not remain indefinitely in "flight mode" should the patient forget to switch this mode to off. One approach involves using a timer, which starts when "flight mode" is selected, to turn off "flight mode" upon expiration. The timer may be set to a duration that guarantees that the flight will have concluded, such as 24 hours, for example.

In the case of a PPC 14 communicating with LCN 200 via an EDGE network, the PPC 14 can have from 1 connection up to 5 connections. The number of connections controls the data rate. When the EDGE network is busy, the number of PPC connections is reduced (e.g., from 4 down to 1). The PPC 14 can detect how many connections are available to it, and modify its behavior accordingly. The PPC 14 utilizes the EDGE and cell tower information to determine how much bandwidth might be available, and to determine if the medium is appropriate for the message's priority/urgency. This information can be included in the APM system's dashboard diagnostics, which is discussed below.

For example, the PPC 14 may detect availability of a large number of connections, which allows the PPC 14 to stream data, such a real-time EGM data, to the APM server 16A. When a reduced number of connections is detected, the PPC 14 adjusts its data output rate and/or content to allow for data transfers at the reduced data rate. The PPC 14 preferably requests more bandwidth based upon urgency. The PPC 14, based on the message priority/urgency, preferably requests the cell tower for more EDGE channel connections. This request feature may be one of the "special services" accorded a PPC 14 as discussed previously. These and other connection features may be subject to prioritization and selection in accordance with a dynamic communication link mapping methodology of the present invention.

Dashboard Diagnostics/Interfaces

Figure 5A:
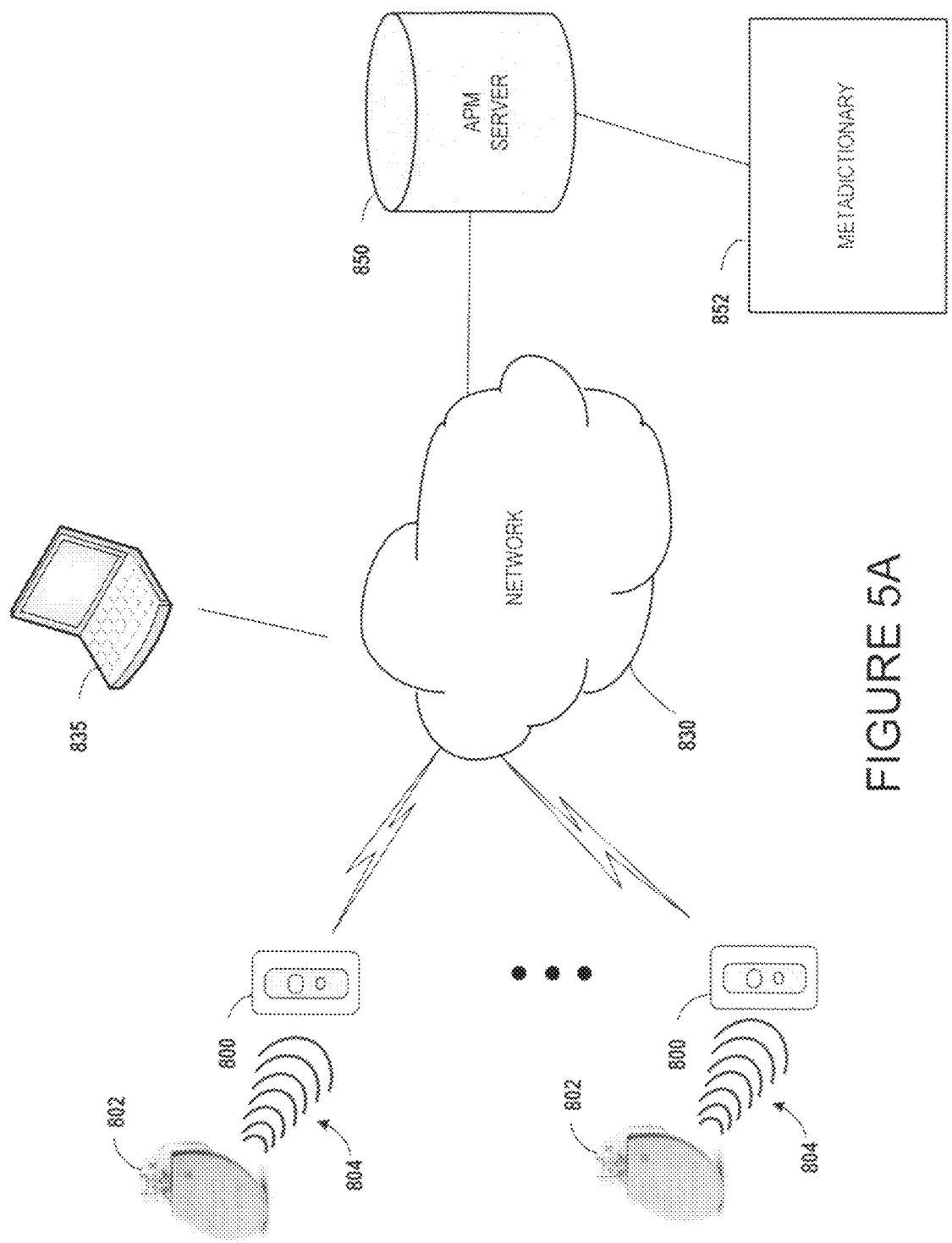
FIG. 5A shows an illustration of a multiplicity of PPCs communicatively coupled to an APM server via a network in accordance with embodiments of the present invention.
Figure 5B:
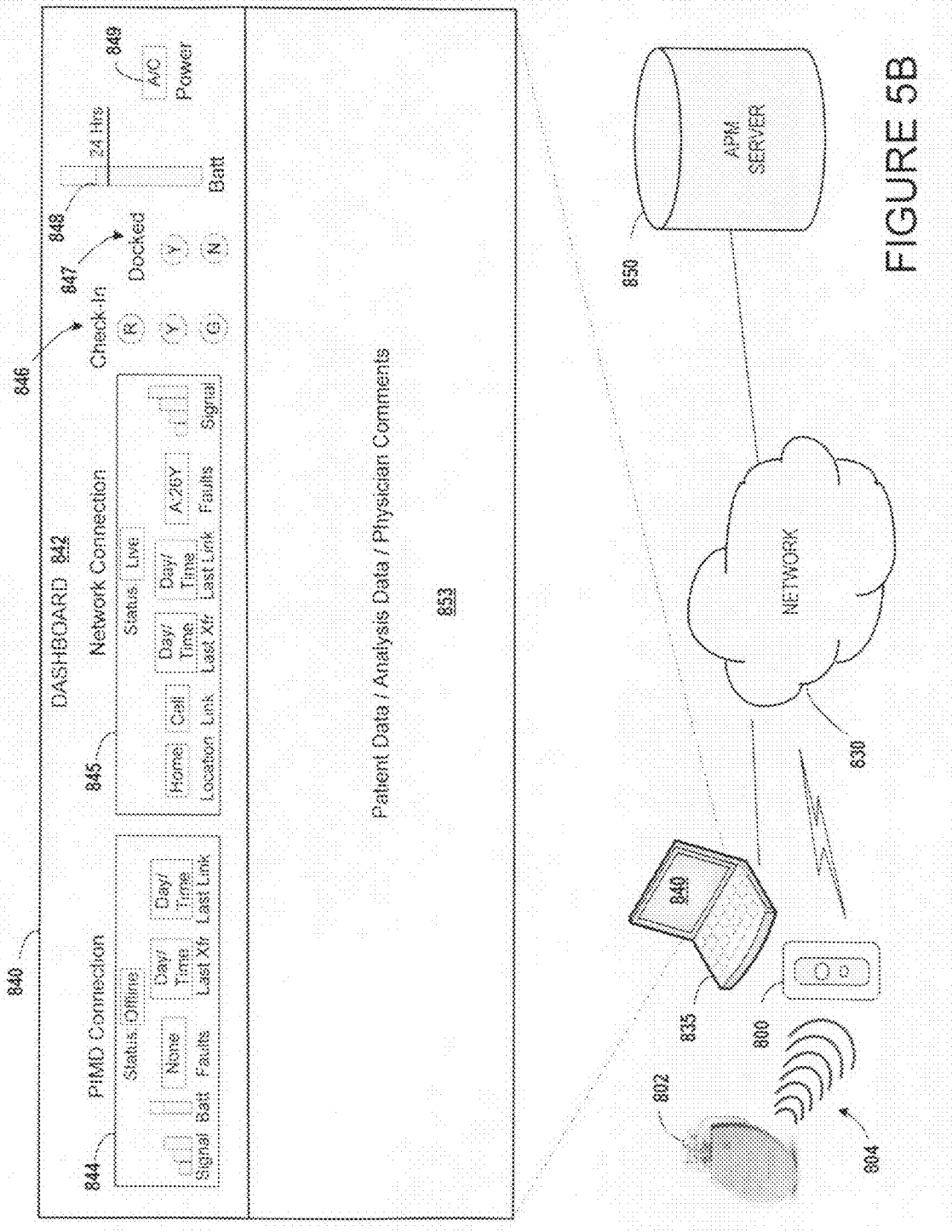
FIG. 5B is an illustration of dashboard diagnostics accessible to local and remote users in accordance with embodiments of the present invention.

The physician or other authorized person may interact with the APM server to access a variety of information concerning a particular patient, the patient's medical device, and/or the PPC. FIGS. 5A and 5B, for example, show a user access device, such as a laptop or PPC 835, that provides authorized access to an APM server 850 via a network 830 (e.g., LCN). The laptop 835 may reside at the physician's office, home or other location (e.g., vacation hotel room). A dashboard diagnostic can be executed on the laptop 835 that, in general, shows information about the status of the PPC 800 and the patient's medical device (e.g., implanted CRM device or other PIMD). The dashboard diagnostic, analogous to an automobile's dashboard that has a variety of gauges and indicators, provides useful diagnostic information about the "health" of the PPC's connection with a communication medium (e.g., cellular network) and with the PIMD 802 or other medical device or sensor with which the PPC 800 communicates.

The dashboard diagnostic shown in FIG. 5B may be used to assess the efficacy of the dynamic communication link mapping methodology of the present invention implemented by each PPC 800. Modification to communication link profiles for each PPC 800 may be made by the physician or other authorized person. The software that implements the dynamic communication link mapping function of a PPC 800 may be modified remotely in order to change the manner in which communication link profiles are generated and executed.

The dashboard or other APM server-based application may be implemented to provide support for near real-time functions, such as PIMD 802 and/or PPC 800 interrogation, EGM and/or other sensor data streaming, over-the-air reconfiguring, software updating (e.g., PIMD firmware updates) and programming (e.g., modifying device parameters or initiating physician commanded functions). Application level packets may be transmitted to request information, and data mining may be performed on the PIMD 802 or PPC 800 by the physician or authorized user. For example, a dashboard application may provide for remote initiation of clinician commanded atrial shock therapy. By way of further example, a dashboard application may allow an authorized user to command the PPC 800 to effect a scan of the PPC's local environment for RF interference. Data acquired from this scan can be shown on an "interference" indicator of the dashboard.

A procedure may be established by which certain information is acquired or exchanged with a PPC 800 that connects with the APM server 850. In general, it is preferably that the PPC 800 communicate with the APM server 850 via a cellular network connection, by which the PPC 800 will interact with the cellular network and exchange information packets with the APM server 850. The PPC 800 is preferably programmed to periodically check-in with the cellular network and with the APM server 850. The PPC 800 may check-in several or many times per day with the cellular network and generally checks-in only once or twice per day (under normal conditions) with the APM server 850.

During a cellular network check-in by the PPC 800, the PPC 800 obtains network/connectivity information such as signal strength, signal band/protocol, or other cellular network information/statistics. During an APM server check-in by the PPC 800, the PPC 800 exchanges patient PIMD/sensor data and further shares a sub-set of that network/connectivity information about its connectivity with the APM server 850, primarily if the PPC 800 has a good connection (e.g., signal strength, quality of service). Selected types of PIMD and network connectivity information may be presented on the dashboard 842.

Various types of diagnostic information acquired by the PPC 800 are preferably made available to the physician or authorized user via a dashboard display 842, which may be presented in a region of the display 840 of a laptop 835 as shown in FIG. 5B. In addition to dashboard information, various types of patient information received from the APM server 850 may be displayed in a patient data portion 853 of the display 840. As with the patient related data, the dashboard data is preferably pulled from the APM server 850 by way of a secured network connection to the laptop or personal computer.

As can be seen in the dashboard 842 in FIG. 5B, a dashboard diagnostic operating on a physician or other authorized user's laptop or personal computer 835 is configured to primarily show connectivity and status information about the PPC 800 and PIMD 802. The layout of the dashboard 842 shown in the embodiment of FIG. 5B includes a PIMD Connection window 844, a Network Connection window 845, a Check-In indicator 846, a Docking Status indicator 847, a Battery Status indicator 848, and a Power Status indicator 849. It is understood that the type and number of data windows and indicators shown in FIG. 5B are for illustrative purposes, and that other of different informational content and manners of displaying same are contemplated.

The Network Connection window 845 provides various information regarding the connection between the PPC 800 and the network 830. The Network Connection Window 845 indicates the present connection state between the PPC 800 and the network 830 (e.g., "live" or "offline"). Such information includes whether or not the patient's PPC 800 is presently connected to the network 830 and by what means (e.g., cellular, landline, satellite, etc.). As shown, the dashboard 842 shows that the PPC 800 is presently connected to the network 830 (i.e., Status: "Live") and that the present connection is via a cellular connection (i.e., Link: "Cell"). It is noted that additional details concerning the "Link" may be displayed, such as by clicking on the "Link" label/button. The strength of the connection between the PPC 800 and the network 830 is shown, such as by use of commonly used signal strength bars. Any faults that have occurred can be viewed in a Fault window.

Other information shown in the Network Connection window 845 includes the day/time of the last or previous contact between the PPC 800 and the network 830/APM server 850, and the last day/time data was transferred between the PPC 800 and the APM server 850. If the physician wishes to see details about the last transfer of information or last connection, additional information may be presented by clicking on the "Last Xfr" label/button or "Last Link" label/button. Still other information includes the location status of the PPC 800, such as whether the PPC 800 is presently stationary (e.g., at the patient's office or home) or mobile. The Location indicator of the Network Connection window 845 shows that the PPC 800 is presently at the patient's home.

A PIMD Connection window 844 of the dashboard 842 provides various information regarding the connection between the PPC 800 and the PIMD 802. The PIMD Connection window 845 indicates the present connection state between the PPC 800 and the PIMD 802 (e.g., "live" or "offline). As shown, the dashboard 842 shows that the PPC 800 is presently not communicating with the PIMD 802 (i.e., Status: "Offline"). The strength of the connection between the PPC 800 and the PIMD network 830 (present strength if connected or of last connection) is shown, such as by use of commonly used signal strength bars.

Other information shown in the PIMD Connection window 844 includes the day/time of the last or previous contact between the PPC 800 and the PIMD 802, and the last day/time data was transferred between the PPC 800 and the PIMD 802. If the physician wishes to see details about the last transfer of information or last connection, additional information may be presented by clicking on the "Last Xfr" label/button or "Last Link" label/button in PIMD Connection window 844. Further information includes the status of the PIMD battery and the fault and/or alert status of the PIMD 802. If the physician wishes to see details about the PIMD faults or alerts, additional information may be presented by clicking on the "Faults" label/button.

The dashboard 842 may include other informational indicators, such as a Check-In indicator 846. The Check-In indicator 846 provides information based on the PPC's most recent connectivity information upload. In the illustrative example shown in FIG. 5B, the Check-In indicator 846 includes a multi-state indicator comprising three colored indicators; red (i.e., circled "R"), yellow (i.e., circled "Y"), and green (i.e., circled "G"). When the physician clicks on a patient's detail page, such as that shown presented in display 840, the physician can see the state of the "red-yellow-green" indicator 846.

If the PPC 800 has not checked-in with the APM server 850 within some time period, the Check-In indicator 846 will show "red." If the PPC 800 has checked-in with only a low/moderate indication of signal strength, the Check-In indicator 846 will show "yellow." If the PPC 800 has checked-in regularly (e.g., 2 or more times within a specified time period) with good signal strength, the Check-In indicator 846 will show "green."

Based on a "green" indication, the APM server web page can allow a physician to initiate an "active connection" with the PPC 800. It is desirable (or may be mandatory) that an active connection be established when both the PPC 800 and the PIMD 802 are not mobile, which may be determined based on the stability of signal strengths or other means. When a non-mobile active connection of sufficient strength is established, the APM server's user interface can allow the physician to initiate an active session. An active connection can allow for a variety of operations, such as real-time streaming of EGMs, physician-initiated interrogation, sending a message to the patient, and remote programming, among others. The APM server's web site can also allow some actions to be performed, even if there can not be an active connection. For example, various types of messages can be transmitted to the PPC 800 or queued to transmit to the PPC 800 when a cellular connection is established.

The PPC 800 may incorporate a display that includes some or all of the indicators provided in the dashboard 842, although various embodiments of the PPC 800 may have a limited user interface, such as in the case of a reduced feature-set PPC 800. For example, the display of the PPC 800 may display an indication to the patient about signal strength (e.g., signal strength bars). It might only display the exception (e.g., yellow or red LED in cases where there is either unstable or no connection). An indicator of the PPC 800 may offer some indication to the patient that a physician/clinical user of the APM server's web site has established an "active connection" with the PPC 800. An alert status indicator (e.g., red LED) may be programmable by the physician/clinical user and activated via the APM server's web site to alert the patient of a problem, thus prompting the patient to contact the physician or APM service representative.

In the Network Connection window 845, an indication of the present location of the PPC 800, in the case of a live connection, or the most recent location, in the case of an offline status indication, is provided to the physician or authorized user. This location information may be used for a variety of purposes, including estimating the stability of the connection if an important data transfer operation is to be conducted (e.g., a PIMD or communicator firmware update), and changing the connection attributes, data access rights, and/or functionality of the PPC 800 depending on location (e.g., greater rights/access granted if at home versus overseas), among others. It is noted that, if the connection status indicator in the Network Connection window 845 indicates that the PPC 800 is "Offline," the most recent dashboard information is presented. The manner in which the location of the PPC 800, including the present geographical location of the PPC 800 if not at the patient's home, may be determined is discussed hereinbelow.

The dashboard 842 will indicate if the PPC 800 is mobile and if it is at its "home" location. As previously mentioned, this can be important for determining if the patient is likely at their place of residence (or other known location such as the patient's office) and if the quality of the cellular connection is likely to be stable. The PPC 800 has a setup procedure, performed once during setup, that will ask the user "are you currently in your home location?" and allow the user to respond with Yes/No. This location can be determined by cell system features. This location can also be identified by the set of cell towers and relative signal strength from each. The PPC 800 stores this "home profile" in internal memory so that it can be tracked later. The Network Connection window 845 of the dashboard 842 will indicate "Not at Home" when the set of cell towers/signal strength does not match the home profile.

A number of indicators tracked by the PPC 800 can be used to determine if the PPC 800 is "mobile" or stationary. For example, a PPC 800 that is switching to multiple different cell towers within a predetermined time period (e.g., the last 10 minutes) is considered mobile. A PPC 800 that has large variations in signal strength with the same cell tower within a predetermined time period (e.g., the last 10 minutes) is considered mobile. Various known cellular-based locating techniques (e.g., triangulation) may be used to determine the present location of the PPC 800. In some embodiments, a GPS receiver may be provided on the PPC 800 or be communicatively coupled (wirelessly or wired) to the PPC 800. For example, a Bluetooth enabled GPS receiver implemented in a portable housing or a GPS receiver integrated into automobile electronics may be paired with the PPC 800 and provide high precision location information to the PPC 800. This location information may be transmitted to the APM server 850 and made available to the physician. An indication of the present location of the PPC 800 is preferably presented on the dashboard 842.

The dashboard 842 is shown to include a docking status indicator 847, a battery indicator 848, and a power status indicator 849. The docking status indicator 847 indicates whether or not the PPC 800 is presently docked with its corresponding base station or hub (e.g., "Y"=Yes if docked to its home hub or "N"=No if not docked to its home hub). A PPC 800 will generally have a corresponding "home" hub that resides at the patient's home, but may also have additional hubs, such as a hub that resides at the patient's office. A portable or travel hub may also be used by the patient when traveling, which may incorporate additional features and functionality, such as a power source converter for connecting with international power sources and a GPS receiver that provides the present location of the travel hub (and, therefore, provides a good estimate of the patient's location).

A PPC 800 is considered at its "home location" and not mobile when it is physically connected to its home hub (or other known "stationary" hub). The power status indicator 849 of the dashboard 842 will indicate if the PPC 800 is currently powered by the hub's battery source or an AC power adapter. The power status indicator 849 allows the physician to know in advance if there is an external source of power for the PPC 800, so that power will not run out during a live communication session. The battery indicator 848 of the dashboard 842 indicates the relative battery energy level of the PPC 800. The battery indicator 848 allows the physician to know if there is enough internal battery power, so that power will not run out during a live communication session. The battery indicator 848 may also include an indicator to show whether the internal battery power of the PPC 800 is sufficient to provide 24 hours of PPC operation. This information may also be provided on the patient's home hub display so that the patient/physician can be assured that a full day's charge is available.

The information provided on the dashboard 842 allows the physician to assess how the patient is using the PPC 800, such as whether the PPC 800 is in communication range, being properly charged, turned on, etc. Over time, the set of status data from the PPC 800 accumulates in the APM server 850. This allows for a report or user interface to show the patient, clinician, or medical device sales representative how effective the patient's use of the PPC 800 has been. Various metrics may be computed, trended, and displayed, such as the percentage of time the PPC 800 contacts the PIMD 802. This provides an indication of how many times PIMD contact was attempted and the number or percentage of successful contacts.

Other useful metrics include an indication of the PPC's average battery power (e.g., the PPC's charge history), whether the patient is keeping the PPC 800 properly charged, how many times the battery has been completely exhausted, and how long the PPC 800 was completely off or inaccessible. The degree of mobility may be a useful metric that indicates whether, and to what extend, the PPC 800 is moving or not. This provides an indication of whether patient is actually taking the PPC 800 with them during their normal activities. This can provide an indication of patient health and quality of life. For example, a mobility metric can show if the patient is active. Metrics can be generated that can be used to assess patient compliance and to implement compliance training. Various reports, statistics, and user interfaces can be used to identify to the patient if they are not keeping the battery charged or not carrying the PPC 800 with them, and encourage the patient to take corrective actions. Patient compliance information can also be generated and presented that reinforces and encourages proper use of the PPC 800 by the patient.

It is contemplated that other dashboards can be implemented that provide useful data for particularized users. For example, a dashboard may be implemented that is oriented towards the clinician/physician. A separate dashboard may be implemented that is oriented towards more network diagnostic. Other dashboards may be implemented that are oriented towards customer service centers for purposes of enhancing troubleshooting efforts by technicians and clinicians.

Moreover, diagnostics other than those discussed above can be shown on a dashboard 842. Such diagnostics include the following: frame error rate of the cellular network connection, frame error rate of the implanted device connection; state of the PPC/PIMD connection (e.g., not-connected, attempting implant connection/wake-up, connected, failed/not-connected); current number of attempts to contact/wakeup the PIMD; last time the PPC had a user interaction (e.g., button pushed, placed on or removed from the docking station); transfer rate metrics (e.g., minimum bps, maximum bps, average bps) for the most recent data transfer; and timestamped connectivity link change history (e.g., GSM→WiFi→GSM) since the PPC connected to the network. Other diagnostics and metrics are contemplated. Dashboard information may be updated at a relatively slow rate, such as once per hour (or faster or slower as desired) Dashboard information may also be updated upon command. Dashboard information may be updated in response to a connection being established between a PPC and the APM server 850.

Updating the firmware of the PPC 800 may be implemented using the dashboard diagnostic or other facility of the APM server 850. The PPC 800 may be viewed as having different sets of firmware. A first set of PPC firmware may be termed medical firmware, a second set of PPC firmware may be termed user interface firmware, and a third set of PPC firmware may be termed cellular radio firmware. These sets of firmware operate substantially independently yet cooperatively to seamlessly effect communications between a governmentally regulated "medical device" (e.g., an implanted CRM device, which is a classified by the FDA as a Class III medical device) and a public communications infrastructure (e.g., cellular network and the Internet). The procedures and requirements for updating different sets of PPC firmware are quite different.

The cellular radio firmware controls the interactions and communications to and from the PPC 800 and the cellular network. This firmware must be independently versioned, tested, and controlled in conjunction with the network providers. The cellular radio firmware is typically upgraded without the need for patient interaction, and can be actioned for upgrade by the cellular network provider or through the APM server 850.

The user interface firmware controls the visual and/or audio content of the PPC 800. The user interface firmware also contains the audio recordings for any sounds generated by the PPC 800. This firmware is updated preferably over-the-air, without involvement from the user. It is controlled by the APM server 850.

The medical firmware controls the activities schedule of the PPC 800, communications between the PPC 800 and the PIMD 802 and other sensors, and data transfers to and from the APM server 850. The medical firmware, for example, ensures that all communications between the PPC 800 and the PIMD 802 conforms to predetermined medical device guidelines, which may include regulatory guidelines that conform to security, encryption, and privacy (e.g., HIPAA) requirements promulgated by a regulatory body, such as the U.S. Food and Drug Administration. The medical firmware also ensures that all communications between the PPC 800 and the network 830 and APM server 850 conform to such regulatory guidelines or requirements. This firmware is updated preferably over-the-air, without involvement from the user.

Over-the-air programming (OTA) is also referred to as over-the-air service provisioning (OTASP), over-the-air provisioning (OTAP) or over-the-air parameter administration (OTAPA), or firmware over-the-air (FOTA), each of which defines methods of distributing new software/firmware updates to cellular phones or provisioning handsets with the necessary settings with which to access services such as WAP or MMS. OTA via SMS, for example, can be implemented to optimize the configuration data updates in SIM cards and handsets, and enable the distribution of new software/firmware updates to mobile phones or provisioning handsets. OTA messaging provides for remote control of mobile phones for service and subscription activation, personalization and programming of a new service for network operators, for example.

In general, the APM server 850 is able to communicate to the cellular network provider and/or queue a message that is general to all PPCs 800. The message is preferably pushed from the APM server 850/network 830 to the PPCs 800 over the least expensive medium and during off-peak hours. An "upgrade available" broadcast message preferably causes the PPCs 800 to initiate communications to the APM server 850 during an off-peak hour, and possibly at a randomized interval to avoid server/network overload, to commence with the upgrade download. The PPCs 800 may use the hub communication medium to contact the server and download the upgrade.

The PPC 800 preferably includes software and hardware that support OTA upgrading. New software or firmware may be transferred from the cellular network provider (or the APM server 850) to the PPC 800, installed, and put into use. It may be necessary to turn the PPC 800 off and back on for the new programming to take effect, which can be programmed to occur automatically at a time when PPC services are not required (e.g., patient is sleeping with no anomalous physiologic conditions detected).

An OTA software or firmware upgrade session can be initiated automatically at an appropriate time or in response to a patient's input. For example, the cellular network provider or APM server 850 can send an SMS message to the PPC 800 requesting the patient to enable the OTA software/firmware upgrade, such as by actuating an update button on the PPC 800. In response, the PPC 800 dials a service number to receive a software/firmware update. It is understood that other modes of performing software/firmware upgrades for the PPC 800 may be used, such as by establishing a wired connection with a server of the cellular network provider or the APM server 850. It is further understood that all or selected groups of PPCs 800 can be upgraded concurrently, such as by the cellular network provider or the APM server 850 broadcasting an SMS message indicating that an upgrade is needed or by performing the upgrade automatically at an appropriate time.

According to some embodiments, firmware upgrades are performed by the cellular network provider pushing the firmware updates to one or more PPCs 800. The updates are tracked on a per-radio basis, such as by use of SIM identification. Firmware updates for each of a PPC's cellular radio firmware, user interface firmware, and medical firmware is tracked and made accessible on the dashboard 842. Notification of a firmware update is generated by the cellular network provider and received by the APM server 850. The update receipt is preferably pulled in by the APM server 850. A check is made to determine if all designated PPCs 800 were successfully upgraded. For PPCs 800 that either did not receive the update (e.g., PPC 800 out of range, poor connection, or turned off) or failed to successfully implement the update (e.g., update was interrupted), the updating procedure is repeated. As was mentioned previously, the updates can be coordinated and delivered by the cellular network provider, the APM server 850 or both.

Generally, the cellular network operator is able to determine which PPCs 800 have what versions of firmware. Reports are typically available to determine which PPCs 800 have older firmware revisions that still need to be updated. These PPCs 800 can be re-targeted for a firmware update. Patients who have these PPCs 800 can be contacted by a customer support representative.

When the PPC 800 is connected to the network 830 and signal strengths and time of day/patient condition are appropriate, a firmware upgrade package is delivered to the PPC 800. The signal strength and battery need to be consistent for a complete transmission. The appropriate time of day can be determined according to network availability and data transfer fees. Night-time/low utilization periods should be preferred. As an alternative implementation for firmware updates, all firmware updates may be sent to the cellular network provider. The cellular network provider preferably uses over-the-air transmission for installing the updates, and the cellular network identifies the PPCs 800 that need the upgrade.

As was previously discussed, the status of each set of PPC firmware is preferably made available on the dashboard 842. Firmware status and updates are preferably tracked on the basis of individual PPC radio, typically by way of SIM data. It may be desirable to provide two or more dashboards, each tailored for a particular user. For example, a physician dashboard may include higher level/summarized information relating to the patient or a group/population of patients, the connected state of the PPC(s) 800, availability of active-connection(s), and patient compliance. In general, the physician does not need all of the detailed connectivity information that is available. A customer service dashboard may include full details, including actual signal strengths, diagnostic information, etc. The customer service dashboard may also provide information about groups or populations of patients and/or users. For example, data about what fraction of patients/users are currently connected, recently connected, out of range, etc., may be accessed via the customer service dashboard, which can provide customer service personnel with valuable information about problem areas that can be further investigated in greater detail.

A PIMD programmer dashboard may be implemented that provides information of particular use to physicians that are accustomed to using a traditional implantable medical device programmer. In general, most of the information that is of interest about a PPC 800 also applies to a PIMD programmer that is connected and on a cellular network. For example, information and trending data on the connectivity status of PIMD programmer, such as signal strengths and percentage of time connected, can be obtained and presented on the programmer dashboard. Information regarding the last check-in by the PIMD programmer, including data, time, and interrogation information, is preferably transferred to the APM server 850 from the PIMD programmer and presented on the PIMD programmer dashboard. The location where a particular programmer is and/or where a given interrogation occurred can be determined and tracked. For example, a programmer is generally an expensive piece of equipment, and it is important to have programmer information for equipment tracking, determining equipment location and availability, and determining equipment servicing needs.

During use, the PIMD programmer can store data in its internal memory for later upload to the APM server 50. The programmer can indicate that it has data ready for upload/streaming and, when connected to the network 830, the programmer can upload the data to the APM server 850. Data associated with implanting a PIMD, for example, can be stored in the programmer's memory for real-time or later transfer to the APM server 850. By way of example, during a PIMD or other medical device implant procedure, a number of records are written, logged, typed, and printed. All or selected records associated with the implant may be communicated from the programmer to the APM server 850. This implant data may be accessed and evaluated by physicians, clinics and hospital personnel and data systems, and medical device manufacturer representatives, for example.

The PIMD programmer can be used to facilitate an active session with the APM server 850 and the PIMD 802, in a manner like the PPC 800. Features such as real-time EGM streaming, for example, are made available. The software and firmware installed on each programmer must generally be tracked by the medical device manufacture to meet tracking requirements. The current version of programmer software, firmware, and other configuration and diagnostic information about the programmer is preferably uploaded to the APM server 850 and made available on the PIMD programmer dashboard.

PPC with Reduced Feature Set

FIG. 4 shows a PPC 800 paired with a PIMD 802 and communicatively coupled thereto via a communications link 804. The PPC 800 may be implemented to provide a wide spectrum of capabilities and functionality. Within this spectrum, the PPC 800 may be configured to provide a variety of features or a limited number of features. In some implementations, for example, the PPC 800 may be configured to have a reduced number of features and capabilities (e.g., a reduced feature set PPC). A PPC 800 configured to have a reduced set of features advantageously reduces the complexity and cost of the device, and enhances acceptance of the device by less sophisticated users. A PPC 800 having a reduced set of features also provides for lower power consumption, such as by minimizing or eliminating a display or other user interface components. The PPC 800 may also be implemented to incorporate a variety of features and capabilities that provide for a wide range of functionality, as will be discussed below with reference to other embodiments.

FIG. 4 illustrates a PPC 800 having a reduced feature set and a relatively small form factor. For example, the PPC 800 shown in FIG. 4 may weigh less than about 6 ounces, and be small enough to fit easily in a purse or pocket. The PPC 800 has a simple user interface (U/I), which is shown to include a single button 801, a small LCD 806 that can provide basic status information (e.g., date, time, signal strength, and battery status), and an LED 808. The LED 808 may indicate ON status of the PPC 800 or other operational status indication. In one implementation, illumination of the LED 808 (or illumination of a green color for a multi-color LED 808, for example) may indicate that the PPC's battery is sufficiently charged to provide at least 24 hours (or other duration) of continuous service. The LED 808 may be controlled to implement a flashing scheme, which may include different colors, that communicates information to the patient. For example, a green ON color may indicate acknowledgement that interaction with the user was successful (e.g., a quick flash green light).

The button 801 may provide basic functionality, such as for initiating patient-interrogated transmissions and pairing/re-pairing procedures. The button 801 may also be actuated by the patient for indicating a distress condition of the patient, to which an emergency service may respond (e.g., 911 alert/call). In this regard, the PPC 800 may be configured to include a GPS transponder or transceiver, or provide location information via other approaches used for locating cellular phone users, which may be used to locate the PPC 800 and, therefore, the patient in an emergency situation. In addition to GPS or other location information, the PPC 800 may communicate patient information obtained from the PIMD 802, which can provide important information about the condition of the patient (e.g., the patient's vital signs obtained remotely by the emergency response service/technician, in addition to location information).

The PPC 800 may have a reduced feature set that excludes a keypad or other more sophisticated user input device, and may also exclude voice channel components associated with conventional cellular phones, for example. The PPC 800, in this configuration, preferably utilizes data or signaling channels of the cellular infrastructure to facilitate communications with remote services and systems.

In some configurations, the button 801 may be a multi-functional button (e.g., contact sensitive switch, multi-state switch or rocker switch). Button activation for controlling PPC functions may include one or more of a quick click, a double click, and a long hold. A button clicking scheme may be developed to perform a variety of operations, including initiating a PIMD 802 interrogation when the patient feels poorly, calling the APM server, and initiating delivery of a pre-configured SMS message to pre-determined parties (e.g., physician, neighbors, friends, children, relatives, emergency response service) to alert the recipient that the patient is in distress or need of attention.

If the PPC 800 detects a condition necessitating a shock and the shock is delivered, the PPC 800 may be programmed to automatically upload data to the APM server, which updates the APM server web site. Detection of the event, remedial action taken by the PPC/PIMD, and initiation of the automatic upload process should be communicated to patient, such as by a flashing LED sequence, so that the patient knows the event has been addressed and recorded. In cases where the APM server needs the patient to perform a function using the PPC 800, the APM server may initiate a phone call to the patient, and request that the patient activate an appropriate button click.

The PPC 800 may incorporate a speaker (preferably without a microphone in the case of a reduced feature set PPC 800, but a microphone can be included on a more robust PPC configuration). An audible feedback mechanism may be implemented as another means of communicating with the patient. The audible output from the speaker is preferably tonal, but voice output can also be employed. A "quiet mode" can be activated, such as by a 5 second button hold, to disable the speaker and, if desired, transition to a vibration/silent mode, if the PPC 800 is equipped with a vibrator device. The PPC 800 may be programmed to produce tones that can be used to transfer data via a TTM scheme, which can be a backup way of communicating to the APM server if cellular network service is unavailable. The speaker may produce a beeper sequence that can be used as a locator (via a button on the PPC's docking hub).

Configurable PPC

A PPC implemented in accordance with embodiments of the present invention may be dynamically configurable via interaction with an APM server and/or a PIMD. This capability of dynamically altering the configuration of a PPC serves to enhance cooperative operation between the PPC, PIMD, and APM system.

FIG. 5A shows an illustration of a multiplicity of PPCs 800 communicatively coupled to an APM server 850 via a network 830. According to the embodiment shown in FIG. 5A, the APM server 850 is coupled to a metadictionary 852. The metadictionary 852 stores information concerning the various types of PIMDs that are supported by the APM server 850. For example, the metadictionary 852 may store detailed information about the serial number, make, model, software/hardware, features, device type or family, etc. about each PIMD that is supported by the APM server 850. The metadictionary data, in short, identifies the capabilities of each PIMD of the system. This information has a number of uses, such as facilitating dynamic configuring of the PPCs 800.

According to one approach, a PPC 800 is paired with its corresponding PIMD 802, such as the paired devices shown in FIG. 4. The PPC 800 preferably receives identification information from the PIMD 802 that uniquely identifies the PIMD 802, such as the model and serial number (e.g., concatenated or combined) of the PIMD 802. The PPC 800 may then communicate this identification information to the APM server 850, which accesses the information for the particularly PIMD 802 stored in the metadictionary 852. Using this information, the APM server 850 may send data to the PPC 800 that configures the PPC 800 to cooperatively operate with the PIMD 802 in accordance with the metadictionary data. In this manner, an "off-the-shelf" PPC can be dynamically configured for use with a particular PPC during a pairing operation via the APM server 850.

For example, the metadictionary data for a particular PIMD 802 may include power capacity and consumption data for the PIMD 802. In response to this data, the PPC 800 may adjust the manner in which it effects communications with the PIMD 802, such as by increasing or decreasing the frequency of non-life critical data from the PPC 800 to the PIMD 802 for transfer to the APM server 850. Various data compression schemes may be used to reduce the volume of data transferred between the PIMD 802 and the PPC 800. In one approach, a number of data compression schemes are available for effecting data transfer between the PIMD 802 and the PPC 800. Metadictionary data may be communicated from the APM server 850 to the PIMD 802 for purposes of substituting or modifying the data compression scheme used by the PIMD 802 and/or PIMD 802, such as for power conservation purposes or for enhancing compatibility with the particular networking protocol.

By way of further example, metadictionary data may be transferred from the APM server 850 to the PPC 800 that modifies a data interrogation routine of the PPC 800, thereby altering the type (and format, if appropriate) of data to be acquired from the PIMD 802 by the PPC 800. This may be particularly useful when conducting research or developing clinical trial protocols. The type of data to be acquired from the PIMD 802 of a particular patient may change as the patient's status (e.g., heart failure status or tachyarrhythmia status) changes over time. The volume of data acquired from the PIMD 802 and/or timing of data transfers may be modified using the PPC 800 in response to metadictionary data received from the APM server 850.

The PPC 800 may also receive a decoder ring associated with its paired PIMD 802 from the metadictionary 852 via the APM server 850. A decoder ring is associated with the particular decoding scheme or logic used by a type or family of PIMDs. Every PIMD has a unique decoding scheme that is identified by the decoder ring associated with the particular PIMD. The decoder ring for a particular PIMD 802 may be transferred from the APM server 850 to the PPC 800 that is paired with the particular PIMD 802. For example, the decoder ring for a particular PIMD 802 may be stored in a SIM card of the PPC 800. Transferring the decoder ring to the PPC 800 at the time of pairing with its associated PIMD 802 advantageously allows a "generic" PPC 800 to be used for effecting communications between a wide variety of PIMDs and the APM server 850.

Firmware of the PPC 800 may be updated by the APM server 850. For example, the metadictionary 852 may identify a number of PPCs 800 that require a particular change in firmware. Version updates and patches may be distributed by the APM server 850 to appropriate PPCs 800 identified by the metadictionary data. By way of further example, communications firmware updates may be distributed to appropriate PPCs 800 to update the PPCs 800 capability to communicate over one or more cellular networks as such networks evolve over time.

In some configurations, the PPCs 800 may incorporate a multi-band radio, such as a quad-band radio. The PPCs 800 may also include multiple short-range radios, such as ISM and SRD radios). The PPCs 800 may switch to different radios depending on the geographical location of the PPCs 800 and the available cellular service (e.g., when traveling from the US to Europe). The PIMD 802 may also change radios, such as in accordance with radio changes made by the PPCs 802 (e.g., ISM to SRD). The PPCs 800 may also include an inductive coil that can be used to establish an auxiliary or backup link between the PPCs 800 and the PIMD 802. In this regard, the PPCs 800 may be used in the similar manner as a conventional wand.

According to one implementation, PPCs 800 may incorporate a software defined radio (SDR) device or module (permanent or replaceable) that can be configured to dynamically define and redefine the communications capabilities of the PPCs 800. An SDR device is a radio communications device that can be programmed to tune to any frequency band and receive any modulation across a large frequency spectrum by means of programmable hardware which is controlled by software.

According to one implementation, the hardware of an SDR incorporated in the PPC 800 may include a superheterodyne RF front end that converts RF signals from and to analog IF signals, and an analog-to-digital converter and digital-to-analog converters which are used to convert a digitized IF signal from and to analog form, respectively. An SDR performs signal processing using a generally purpose CPU or a reconfigurable piece of digital electronics. Incorporating an SDR in the PPC 800 advantageously provides for a radio that can receive and transmit a new form of radio protocol simply by running new software that can be distributed to the PPC 800 from the APM server 850. An SDR may be configured to operate with different modalities, including short range modalities (e.g., Bluetooth, Zigbee, FM) and long range modalities (e.g., RF telemetry utilizing MICS, ISM or other appropriate radio bands). A more advanced SDR may support multiple communications modalities as selected by the PPC 800 or APM 850. These various modalities typically differ in terms of power consumption and transmission range, and may be programmed, enabled, and/or selected based on these and other considerations.

PPC and APM System

Figure 6:
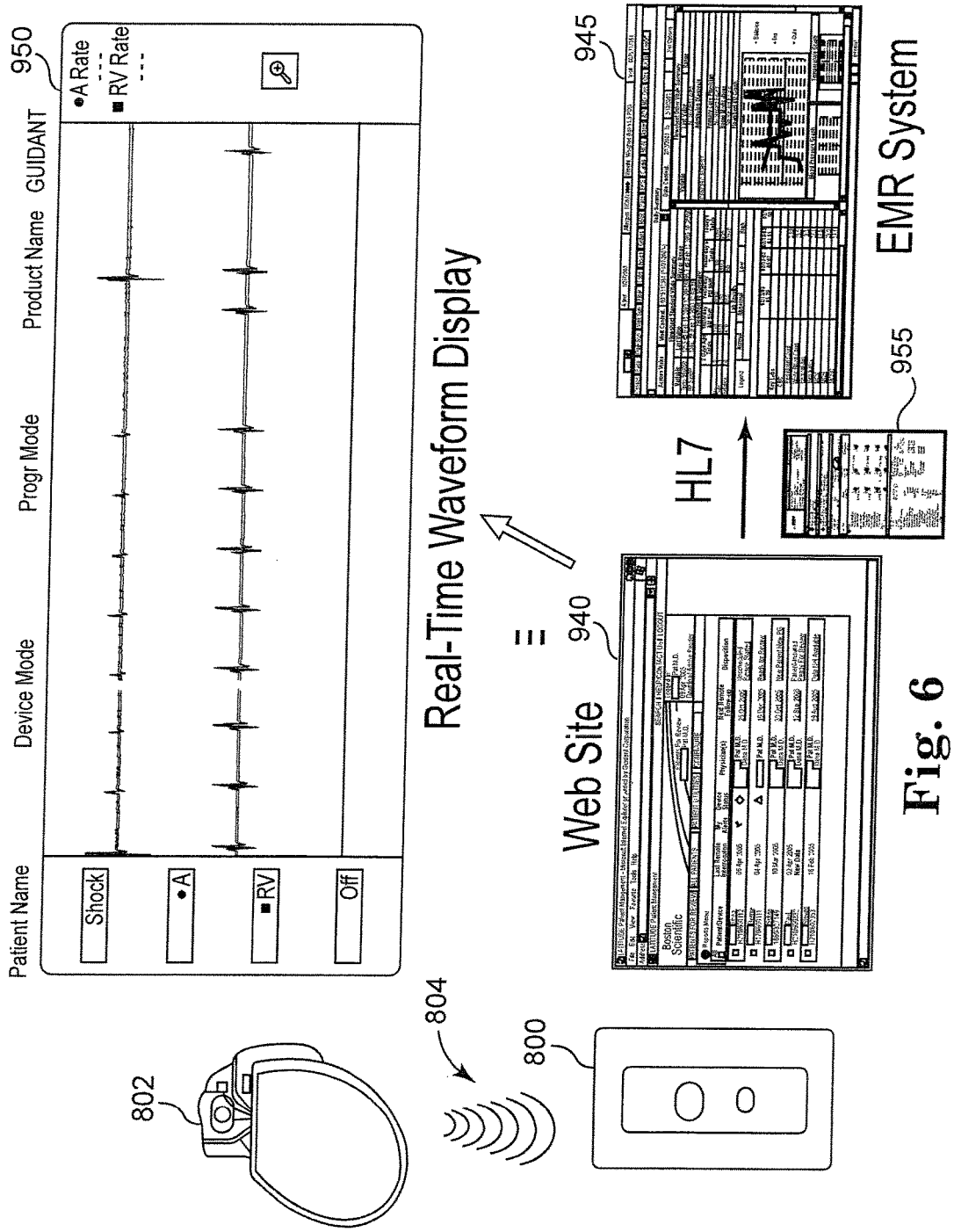
FIG. 6 illustrates various types of PIMD data that can be transferred from a PIMD to a PPC, from the PPC to an APM server, and from the APM server to the clinician or other user in accordance with embodiments of the present invention.

FIG. 6 illustrates various types of PIMD data that can be transferred from a PIMD 802 to a PPC 800, from the PPC 800 to an APM server 850, and from the APM server 850 to the clinician or other user. As is depicted in FIG. 6, various physiological data acquired by the PIMD 802 are transferred to the PPC 800. This data may be transferred by the PIMD 802 to the APM server 850 in real-time mode or batch mode. For example, occurrence of a predetermined event may trigger a data transfer operation from the PIMD 802 to the PPC 800. Based on the criticality of the event, the event data may be temporarily stored in the PPC 800 for later transmission to the APM server 850, in the case of less critical events. In the case of critical events, immediate connectivity may be made between the PPC 800 and the APM server 850, and PIMD data may be communicated to the APM server 850 in real-time (e.g., real-time streaming of PIMD data from the PIMD 802 to the APM server 850 via the PPC 800). It is understood that the term "real-time" connotes a manner of communicating data as fast as is practicable from a transmission source to a receiving device given real-world (i.e., non-ideal) technological practicalities, such as connection and transfer delays, among others.

In accordance with embodiments of the present invention, PIMD interrogation, programming, data transfer operations (e.g., incremental data transfers), and query/response protocol operations need not be subject to a predefined schedule (e.g., between nighttime hours of 1-3 AM), but may be event based. Events detected by the PIMD 802 or actions initiated by the patient (e.g., pushing a button on the PPC 800) may trigger cooperative operation between the PIMD 802 and PPC 800 or between the PIMD 802, PPC 800, and the APM server 850. Certain events may trigger real-time connectivity between the PPC 800 and the APM server 850, while others may trigger store-and-forward data transfer operations. It is noted that it may be desirable to limit patient interaction with the PIMD 802 in non-critical situations, such as for conserving battery power.

Cooperative operation between the PIMD 802, PPC 800, and the APM server 850 provides for a number of useful real-time capabilities. For example, real-time monitoring of patients by remotely located clinicians may be realized, which may include real-time waveform display, real-time physiological monitoring for remote triage, real-time physiological monitoring and display at a remote clinician location, and real-time leadless ECG waveform viewing. Real-time clinical alerts for high risk patients may be generated at a remote location in response to predetermined patient events. Patient data may be streamed to the APM web site and displayed within a browser plug-in, which may include smoothed anti-aliased display of physiological waveforms at 24 frames per second or higher. In this regard, cooperative operation between the PIMD 802, PPC 800, and the APM server 850 may facilitate implementation of an "always on" or at least an "always available" life critical network when the PPC 800 establishes a network connection.

FIG. 6 shows data transferred from a PIMD 802 and PPC 800 to a website 940 supported by an APM server 850. Data acquired from the PIMD 802 may be organized in the manner shown in FIG. 6. Data acquired from the PIMD 802 and stored in the APM server 850 may be transferred to, and incorporated within, an electronic medical records system 945, additional details of which are disclosed in commonly owned U.S. Patent Publication No. 20070226013, which is incorporated herein by reference.

FIG. 6 also shows real-time PIMD 802 data displayed graphically. In this illustrative depiction, real-time EGM data for multiple channels (RV, atrial, and shock channels) is displayed. Atrial and ventricular rates, along with other data, may also be displayed. Date regarding the patient, device mode, programmer mode, and the PIMD 802 may be displayed. Detailed data 955 concerning the PIMD 802 may be displayed in real-time and/or output in report form.

PPC Communications Interfaces

The PPC 800 preferably incorporates a built-in transceiver that may be configured to establish bi-directional communication with a network utilizing various known communication protocols, such as those used in cellular networks. The PPC 800 also incorporates a short range transceiver for establishing a local communication link 804 between the PPC 800 and PIMD 802, and, in some embodiments, between the PPC 800 and one or more sensors disposed on the PPC 800 (or other patient sensors in proximity to the PPC 800). The local communication link 804 may be established in accordance with a variety of known protocols, such as MICS, ISM, or other radio frequency (RF) protocols, and those that confirm to a Bluetooth standard, IEEE 802 standards (e.g., IEEE 802.11), a ZigBee or similar specification, such as those based on the IEEE 802.15.4 standard, or other public or proprietary wireless protocol.

The PPC 800 may incorporate a communications port 814 that may be configured to receive a connector for a hardwire communication link. In such a configuration, a conductor (electrical or optical) may be connected between the hardwire connector or communication port 814 of the PPC 800 and an appropriate connector of a patient-external system, such as a laptop. The hardwire connection port 814 of the PPC 800, and any necessary interface circuitry, may be configured to communicate information in accordance with a variety of protocols, such as FireWire (IEEE 1394), USB, or other communications protocol (e.g., Ethernet). It is understood that various hardwire connection protocols allow for the transmission of power in addition to data signals (e.g., USB), and that such connections may be used to recharge an internal or backup battery source 812 of the PPC 800.

Using the description provided herein, embodiments of the invention may be implemented as a machine, process, or article of manufacture by using standard programming and/or engineering techniques to produce programming software, firmware, hardware or any combination thereof. Any resulting program(s), having computer-readable program code, may be embodied on one or more computer-usable media such as resident memory devices, smart cards or other removable memory devices, or transmitting devices, thereby making a computer program product or article of manufacture according to the invention. As such, the terms "article of manufacture," "computer program product," "computer-readable media" and other similar terms as used herein are intended to encompass a computer program that exists permanently or temporarily on any computer-usable medium or in any transmitting medium which transmits such a program.

As indicated above, memory/storage devices include, but are not limited to, disks, optical disks, removable memory devices such as smart cards, SIMs, WIMs, semiconductor memories such as RAM, ROM, PROMS, etc. Transmitting mediums include, but are not limited to, transmissions via wireless/radio wave communication networks, the Internet, intranets, telephone/modem-based network communication, hard-wired/cabled communication network, satellite communication, and other stationary or mobile network systems/communication links.

From the description provided herein, those skilled in the art are readily able to combine software created as described with appropriate general purpose or special purpose computer hardware to create a mobile system and/or device and/or subcomponents embodying aspects of the invention, and to create a mobile system and/or device and/or subcomponents for carrying out the methods of the invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of transporting medical information across a network configured to service a plurality of geographical locations, comprising:
   querying the network by a processor of a portable source medical device movable relative to the plurality of geographical locations;
   determining, by the processor, communication links of the network presently available to effect communications between the source medical device and a target component when the source medical device is at each of the geographical locations;
   generating, by the processor, each of a plurality of profiles, wherein each profile comprises information about each of the available communication links and attributes associated with each of the available communication links for each of the geographical locations;
   prioritizing, by the processor, the communication links;
   storing all of the plurality of profiles in the source medical device;
   accessing, by the processor, when the source medical device is at a particular geographical location of the plurality of geographical locations, a particular profile from the plurality of profiles stored in the source medical device that is associated with the particular geographical location;
   selecting, by the processor, a communication link associated with the particular profile based on the prioritization of the communication links;
   establishing a network connection between the source medical device and the target component using the selected communication link associated with the particular profile;
   receiving medical information, by the processor, from one or more medical devices; and
   transferring medical information between the source medical device and the target component via the selected communication link associated with the particular profile.

2. The method of claim 1, wherein the prioritization of the communication links is based at least in part on one or more factors concerning the communication link, the one or more factors comprising bandwidth, integrity, and security.

3. The method of claim 1, wherein the prioritization of the communication links is based at least in part on one or more factors concerning the communication link, the one or more factors comprising quality of service and level of guaranteed delivery.

4. The method of claim 1, wherein the prioritization of the communication links is based at least in part on one or more factors concerning the communication link, the one or more factors comprising cost, profile of a user of the source medical device, and particulars of a service agreement that defines financial and usage terms as between the user of the source medical device and a central authority of the network.

5. The method of claim 1, wherein the prioritization of the communication links is based at least in part on one or more factors concerning the communication link, the one or more factors comprising priority or urgency of the medical information.

6. The method of claim 1, wherein the prioritization of the communication links is based at least in part on type of source medical device, the type of source medical device comprising at least an implantable cardiac rhythm management device, a physiologic sensor, and a patient sensor.

7. The method of claim 1, comprising selectively enabling and disabling capabilities of one or both of the communication link and target component services based on one of both of a profile of a user of the source medical device and particulars of a service agreement that defines financial and usage terms as between the user of the source medical device and a central authority of the network.

8. The method of claim 1, wherein the target component comprises a central authority of the network, and the central authority is configured to establish a communication path via nodes of the network having attributes indicated by the particular profile.

9. The method of claim 1, wherein the profile is generated by the source medical device.

10. The method of claim 1, comprising determining the geographical location of the source medical device at least in part using a network implemented locating mechanism.

11. The method of claim 1, comprising determining the geographical location of the source medical device using a mechanism other than a network implemented locating mechanism.

12. The method of claim 1, wherein the target component comprises a remote patient monitoring system.

13. A system for transporting medical information across a network configured to service a plurality of geographical locations, comprising:
   a source medical device configured for portability relative to the plurality of geographical locations, the source medical device comprising or coupled to a mapping agent and a profile library, the mapping agent comprising:
      a processor configured to execute program instructions for querying the network and determining communication links of the network presently available to effect communications between the source medical device and a target component when the source medical device is at each of the geographical locations;
      the processor configured to execute program instructions for designating one or more of the geographic locations as a regular destination;
      the processor configured to execute program instructions for generating a profile comprising information about each of the available communication links and attributes associated with each of the available communication links for each regular destination, to store each of the profiles in the profile library, and to prioritize the communication links;
      the processor configured to execute program instructions for accessing, when the source medical device is at a particular regular destination of the plurality of geographical locations, a particular profile stored in the source medical device that is associated with the particular regular destination, select a communication link associated with the particular profile based on the prioritization of the communication links, establish a network connection between the source medical device and the target component using the selected communication link associated with the particular profile, and transfer medical information between the source medical device and the target component via the selected communication link associated with the particular profile.

14. The system of claim 13, wherein the processor is configured to prioritize the communication links based at least in part on one or more factors concerning the communication link, the one or more factors comprising bandwidth, integrity, and security.

15. The system of claim 13, wherein the processor is configured to prioritize the communication links based at least in part on one or more factors concerning the communication link, the one or more factors comprising quality of service and level of guaranteed delivery.

16. The system of claim 13, wherein the processor is configured to prioritize the communication links based at least in part on one or more factors concerning the communication link, the one or more factors comprising cost, profile of a user of the source medical device, and particulars of a service agreement that defines financial and usage terms as between the user of the source medical device and a central authority of the network.

17. The system of claim 13, wherein the processor is configured to prioritize the communication links based at least in part on one or more factors concerning the communication link, the one or more factors comprising priority or urgency of the medical information.

18. The system of claim 13, wherein the processor is configured to prioritize the communication links based at least in part on type of source medical device, the type of source medical device comprising at least an implantable cardiac rhythm management device, a physiologic sensor, and a patient sensor.

19. The system of claim 13, wherein a central authority of the network is configured to selectively enable and disable capabilities of one or both of the communication link and target component services based on one of both of a profile of a user of the source medical device and particulars of a service agreement that defines financial and usage terms as between the user of the source medical device and a central authority of the network.

20. The system of claim 13, wherein the target component comprises a central authority of the network, and the central authority is configured to establish a communication path via nodes of the network having attributes indicated by the particular profile.

21. The system of claim 13, wherein the profile is generated by the source medical device.

22. The system of claim 13, wherein a locating mechanism of the network is configured to determine the geographical location of the source medical device.

23. The system of claim 13, wherein a location sensor integral or coupled to the source medical device is configured to determine the geographical location of the source medical device.

24. The system of claim 13, wherein the target component comprises a remote patient monitoring system.

25. A system for transporting medical information across a network configured to service a plurality of geographical locations, comprising:
a portable source medical device configured to receive medical information from one or more medical devices of a patient, wherein the portable source medical device is movable relative to the plurality of geographical locations and configured to query the network;
means for determining communication links of the network presently available to effect communications between the source medical device and a target component when the source medical device is at each of the geographical locations;
means for generating a profile comprising information about each of the available communication links and attributes associated with each of the available communication links for each of the geographical locations;
means for prioritizing the communication links;
memory configured to store all of the profiles in the source medical device;
means for accessing, when the source medical device is at a particular geographical location of the plurality of geographical locations, a particular profile stored in the source medical device that is associated with the particular geographical location;
means for selecting a communication link associated with the particular profile based on the prioritization of the communication links;
means for establishing a network connection between the source medical device and the target component using the selected communication link associated with the particular profile; and
means for transferring medical information between the source medical device and the target component via the selected communication link associated with the particular profile.

\* \* \* \* \*